(12) United States Patent
Meganck et al.

(10) Patent No.: US 10,497,154 B2
(45) Date of Patent: Dec. 3, 2019

(54) SYSTEMS AND METHODS FOR AUTOMATED SINOGRAM COMPLETION, COMBINATION, AND COMPLETION BY COMBINATION

(71) Applicants: PerkinElmer Health Sciences, Inc., Waltham, MA (US); iTomography Corp., Houston, TX (US); University of Central Florida Research Foundation, Inc., Orlando, FL (US)

(72) Inventors: Jeff Meganck, Grafton, MA (US); Michael Frenkel, Barker, TX (US); Alexander Katsevich, Oviedo, FL (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 126 days.

(21) Appl. No.: 15/614,299

(22) Filed: Jun. 5, 2017

(65) Prior Publication Data
US 2017/0365075 A1    Dec. 21, 2017

Related U.S. Application Data

(60) Provisional application No. 62/346,090, filed on Jun. 6, 2016.

(51) Int. Cl.
*G06K 9/00* (2006.01)
*G06T 11/00* (2006.01)
(Continued)

(52) U.S. Cl.
CPC .......... *G06T 11/006* (2013.01); *A61B 6/5211* (2013.01); *G06T 7/0012* (2013.01);
(Continued)

(58) Field of Classification Search
None
See application file for complete search history.

(56) References Cited

U.S. PATENT DOCUMENTS

| 6,915,005 B1 | 7/2005 | Ruchala et al. | |
| 2008/0253636 A1* | 10/2008 | Deller | A61B 5/113 |
| | | | 382/131 |
| 2011/0142316 A1* | 6/2011 | Wang | G06T 11/006 |
| | | | 382/131 |

FOREIGN PATENT DOCUMENTS

EP    2 383 702 A1    11/2011

OTHER PUBLICATIONS

Wiguna ("Interpolation Method in Simple Computed Tomography Scanner", in Proceedings of SPIE—The International Society for Optical Engineering • Mar. 2015, pp. 1-5). (Year: 2015).*

(Continued)

*Primary Examiner* — Wei Wen Yang
(74) *Attorney, Agent, or Firm* — Banner & Witcoff, Ltd.

(57) ABSTRACT

Described herein are systems and methods for automated completion, combination, and completion by combination of sinograms. In certain embodiments, sinogram completion is based on a photographic (e.g. spectral or optical) acquisition and a CT acquisition (e.g., micro CT). In other embodiments, sinogram completion is based on two CT acquisitions. The sinogram to be completed may be truncated due to a detector crop (e.g., a center-based crop or an offset based crop). The sinogram to be completed may be truncated due to a subvolume crop (e.g., based on low resolution image projected onto sinogram).

27 Claims, 25 Drawing Sheets

(51) Int. Cl.
*A61B 6/00* (2006.01)
*G06T 7/00* (2017.01)
*A61B 6/03* (2006.01)

(52) U.S. Cl.
CPC ............ *G06T 11/005* (2013.01); *A61B 6/032* (2013.01); *A61B 6/481* (2013.01); *G06T 2207/10081* (2013.01); *G06T 2207/10116* (2013.01); *G06T 2211/432* (2013.01)

(56) References Cited

OTHER PUBLICATIONS

Gert Van Gompel ("Towards accurate image reconstruction from truncated X-ray CT projections", 2009, pp. 1-172) (Year: 2009).*
International Search Report, PCT/US2017/035986, 4 pages, dated Aug. 23, 2017.
Ketcham, Richard, X-ray computed Tomography (CT), Geochemical Instrumentation and Analysis, Last Modified: Nov. 10, 2016, [retrieved Mar. 28, 2017: http://serc.carleton.edu/research_education/geochemsheets/techniques/CT.html].
Maaß, C. et al., Simple ROI cone-beam computed tomography, Nuclear Science Symposium Conference Record, 2010 IEEE, pp. 3161-3168 (2010).
Written Opinion, PCT/US2017/035986, 8 pages, dated Aug. 23, 2017.

* cited by examiner

SYSTEMS AND METHODS FOR AUTOMATED SINOGRAM COMPLETION, COMBINATION, AND COMPLETION BY COMBINATION

RELATED APPLICATIONS

This application claims priority to and the benefit of U.S. Provisional Patent Application No. 62/346,090 entitled "Systems and Methods for Automated Sinogram Completion, Combination, and Completion by Combination" and filed on Jun. 6, 2016, the contents of which is hereby incorporated by reference in its entirety.

TECHNICAL FIELD

This invention relates generally to methods and systems of biological imaging (e.g. clinical and/or research) and image analysis. More particularly, in certain embodiments, the invention relates to systems and methods for automated completion, combination, and completion by combination of sinograms.

BACKGROUND

There is a wide array of technologies directed to in vivo and ex vivo imaging of mammals—for example, optical (e.g. bioluminescence and/or fluorescence), X-ray computed tomography, and multimodal imaging technologies. In vivo imaging of small mammals and ex vivo imaging of samples from small mammals is performed by a large community of investigators in various fields, e.g., oncology, infectious disease, and drug discovery.

Micro computed tomography (hereafter, "microCT") imaging, is an x-ray-based technology that can image tissues, organs, and non-organic structures with an extremely high resolution. MicroCT has evolved quickly, requiring low dose scanning and fast imaging protocols to facilitate multi-modal applications and enable longitudinal experimental models. Similarly, nano-computed tomography (nanoCT) systems designed for high-resolution imaging of ex vivo samples are also now used. Multi-modal imaging involves the fusion of images obtained in different ways, for example, by combining fluorescence molecular tomography (FMT), PET, MRI, CT, and/or SPECT imaging data.

Multimodal imaging allows improved visualization of disease biology, e.g., for use in drug development and diagnostics. By utilizing in vivo bioluminescent and fluorescent agents and/or radioactive probes, researchers can measure depth, volume, concentration, and metabolic activity, facilitating medical research. Coregistration allows researchers to overlay images from multiple imaging modalities, providing more comprehensive insight into the molecular and anatomical features of a model subject. For example, optical imaging data can be used to identify and quantify tumor burden at the molecular level and, when integrated with microCT, provides a quantitative 3D view of anatomical and functional readouts.

Various systems have been developed that allow accurate multimodal imaging. For example, various IVIS® in vivo imaging systems, manufactured by PerkinElmer headquartered in Waltham, Mass., feature a stable revolving animal platform (horizontal gantry motion with flat panel detector) for acquisition of 3D data, facilitating low-dose imaging and automated optical and micro-CT integration. Such systems provide 3D tomography for bioluminescent and fluorescent reporters, enhanced spectral unmixing for multispectral imaging, Cerenkov imaging for optical radiotracer imaging, and dynamic enhanced imaging for real time distribution studies of fluorochromes and/or PET tracers, e.g., for pharmacokinetic/pharmacodynamics PK/PD modeling.

Conventional computed tomography (CT) imaging systems may require higher-than-desirable radiation doses to obtain satisfactory reconstructed images and may pose challenging memory management problems. CT image reconstruction from multiple projections is computationally intensive. CT image reconstruction generally involves obtaining a sinogram, which is a multi-dimensional array of data containing projections from a scanned object (e.g., projections recorded for a plurality of angles during multi-angle scanning of an object).

Artifacts arise when imaging objects that are too large to fit into the physical beam of a given system, or when the object is too large for a given reconstruction field of view (FOV) due to memory or data storage limitations. Furthermore, it is often desirable to reduce radiation dose by only exposing a particular area of interest. However, such situations result in sinogram data truncation which must be "filled in" to permit reconstruction. No adequate solutions have been proposed for automated sinogram completion in a multi-modality approach.

Thus, there is a need for systems and methods for automated completion of a truncated sinogram to permit satisfactory image reconstruction and coregistration/combination with optical images.

SUMMARY OF THE INVENTION

Presented herein are systems and methods for automated completion, combination, and completion by combination of sinograms. In certain embodiments, sinogram completion is based on a photographic (e.g. spectral or optical) acquisition and a CT acquisition (e.g., micro CT). In other embodiments, sinogram completion is based on two CT acquisitions. The sinogram to be completed may be truncated due to a detector crop (e.g., a center-based crop or an offset based crop). The sinogram to be completed may be truncated due to a subvolume crop (e.g., based on low resolution image projected onto sinogram).

In one aspect, the invention is directed to a method for automated sinogram completion (e.g., where the sinogram to be completed is truncated due to a detector crop), the method comprising the steps of: (a) accessing (e.g., and/or acquiring), by a processor of a computing device, a downsampled sinogram (e.g., wherein each of a plurality of projections of the downsampled sinogram represents signals acquired across a first region of a detector and has a first resolution; e.g., $S_{4\times4}$, from full panel bin 4 images) comprising data recorded by a detector during multi-angle scanning (e.g., a CT scan; e.g., a first scan) of a subject; (b) accessing (e.g., and/or acquiring), by the processor, a truncated sinogram comprising data recorded by the detector during multi-angle scanning (e.g., a CT scan; e.g., a second scan; e.g., the first scan) of the subject (e.g., $S_{1\times1,trunc}$); (c) interpolating, by the processor, each projection of the downsampled sinogram based on a resolution of the truncated sinogram, thereby obtaining a plurality of interpolated projections (e.g., interpolating each projection of $S_{4\times4}$ with bin 1 to obtain $S_{4\times4\_to\_1\times1}$); (d) determining, by the processor, a plurality of combined projections using projections of the truncated sinogram and the interpolated projections [e.g., by replacing empty columns from the truncated images with interpolated data (e.g., replacing empty columns in $S_{1\times1,trunc}$ with interpolated data from $S_{4\times4\_to\_1\times1}$) to obtain combined projections (e.g., projections of a combined sinogram, $S_{combined}$)]; and (e) creating, by the processor, a 3D image of the subject (e.g., via tomographic reconstruction) using the combined projections.

In certain embodiments, each projection of the downsampled sinogram represents signals recorded across a first region of a detector (e.g., recorded for a given angle of a multi-angle scan of the subject) and has a first resolution [e.g., each data element of the projection is associated with N pixels of a specific location on the detector and stores a value representing signal(s) detected from the N pixels with which it is associated (e.g., N is an integer greater than or equal to 1)], and each projection of the truncated sinogram represents signals from recorded across a second region of the detector (e.g., recorded for a given angle of a multi-angle scan of the subject) and has a second resolution [e.g., each data element of the projection is associated with M pixels of a specific location on the detector and stores a value representing signal(s) detected from the M pixels with which it is associated (e.g., M is an integer greater than or equal to 1)], wherein the second region is a sub-region of the first region and the second resolution is higher than the first resolution (e.g., M<N).

In certain embodiments, each projection of the downsampled sinogram is interpolated based on a resolution of the truncated sinogram to convert the resolution of each projection of the downsampled sinogram to the resolution of the truncated sinogram (e.g., to convert the resolution of each projection of the downsampled sinogram from the first resolution to the second resolution).

In certain embodiments, determining each combined projection of the plurality of combined projections comprises: storing, in data elements of the combined projection that are associated with locations of the detector that are within a first region of the detector but outside of a second region of the detector, values from corresponding data elements (e.g., that are associated with a same location on the detector) of a corresponding interpolated projection (e.g., associated with a same angle), wherein each projection of the downsampled sinogram stores data representing signals from a first region and each projection of the truncated sinogram stores data representing signals from the second region; and storing, in data elements of the combined projection that are associated with locations of the detector within the second region, values from corresponding data elements (e.g., that are associated with a same location on the detector) of a corresponding projection (e.g., associated with a same angle) of the truncated sinogram.

In certain embodiments, the 3D image of the subject is obtained via tomographic reconstruction wherein each projection of a plurality of projections is processed individually such that, for each projection, a reconstruction sub-step is performed that (i) operates on the given projection (e.g., back-projects the projection, e.g., filters the projection then back-projects the filtered projection), and (ii) updates values of a stored 3D dataset by combining the result of (i) with the stored 3D dataset, wherein the 3D dataset is the 3D image of the subject following the processing of the plurality of projections.

In certain embodiments, the method comprises performing steps (c) through (e) such that it is only necessary to store one combined projection in memory (e.g., random access memory (RAM)) at a time (e.g., by, for each angle of a plurality of angles, processing projections associated with the angle such that only one combined projection needs to be determined and stored in memory).

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the method comprises acquiring, via a first multi-angle scan of the subject, a plurality of downsampled projections to obtain the downsampled sinogram; and acquiring, via a second multi-angle scan of the subject, a plurality of truncated projections to obtain the truncated sinogram.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, the method comprises, for each of a plurality of angles of a multi-angle scan of the subject (e.g., a multi-angle CT scan): acquiring a corresponding initial projection that stores data representing signals from a first region of the detector (e.g., the full detector area); downsampling, by the processor, the acquired projection to a reduced resolution, thereby obtaining a downsampled projection having a resolution that is lower than that of the initial projection (e.g., such that the downsampled projection takes up less memory than the initial projection); storing, by the processor, the downsampled projection as a projection of the downsampled sinogram; cropping, by the processor, the initial projection to obtain a truncated projection that stores data representing signals from a region of the detector that is a subregion of the first region smaller than the first region [e.g., by removing data elements associated with locations of the detector outside the subregion; e.g., by setting values of data elements associated with locations of the detector outside of the subregion to a constant value (e.g., 0; e.g., a 'null'); e.g., such that the truncated projection takes up less memory than the initial projection]; and storing the truncated projection as a projection of the truncated sinogram.

In certain embodiments, the processor comprises one or more processing units of a first type (e.g., central processing units (CPUs)) and one or more processing units of a second type (e.g., graphics processing units (GPUs)). In certain embodiments, steps (a) and (b) are performed by one or more processing units of the first type (e.g., central processing units (CPUs)) and steps (c) through (e) are performed by one or more processing units of the second type (e.g., graphics processing units (GPUs)).

In certain embodiments, the second region of the detector is predefined (e.g., via a configuration in a CT scanner used to obtain a multi-angle scan of the object).

In certain embodiments, the method comprises: identifying, by the processor (e.g., automatically; e.g., via a user interaction), within an image of the subject (e.g., a previously obtained image; e.g., an optical image; e.g., a fluorescence image, a bioluminescence image, or other light based image; e.g., a low resolution image of the subject obtained (e.g., via tomographic reconstruction) using the downsampled sinogram) a region of interest (ROI); and determining, by the processor, the second region of the detector based on the identified ROI (e.g., such that the field of view of the second region corresponds to the ROI).

In another aspect, the invention is directed to a method for automated sinogram completion (e.g., where the sinogram to be completed is truncated due to a detector crop), the method comprising the steps of: (a) accessing (e.g., and/or acquiring), by a processor of a computing device, a downsampled sinogram (e.g., $S_{4\times 4}$, from full panel bin 4 projections) for a subject, wherein the downsampled sinogram comprises a plurality of downsampled projections, wherein: each downsampled projection is associated with a specific angle of a multi-angle scan of the subject, each downsampled projection stores data representing signals from a first region of a detector recorded for the specific angle with which the downsampled projection is associated, and each downsampled projection has a first resolution [e.g., each data element of the projection is associated with N pixels of a specific location on the detector and stores a value representing signal(s) detected from the N pixels with which it is associated (e.g., N is an integer greater than or equal to 1)]; (b) accessing (e.g. and/or acquiring), by the processor a truncated sinogram for the subject, wherein the truncated sinogram comprises a plurality of truncated projections, wherein: each truncated projection is associated with a specific angle of a multi-angle scan of the subject, each truncated projection stores data representing signals from a second region of a detector recorded for the specific angle with which the truncated projection is associated, wherein the second region is a sub-region of the first region, and each truncated projection has a second resolution [e.g., each data element of the projection is associated with M pixels of a specific location on the detector and stores a value representing signal(s) detected from the M pixels with which it is associated (e.g., M is an integer greater than or equal to 1)], wherein the second resolution is higher than the first resolution (e.g., M<N); (c) initializing a 3D dataset (e.g., setting all elements of the 3D dataset to 0), and, for each angle with which a downsampled projection is associated: (i) interpolating, by the processor, the downsampled projection to convert its resolution from the first resolution to the second resolution, thereby obtaining an interpolated projection; (ii) obtaining, by the processor, a combined projection using data from the interpolated projection and data from a corresponding truncated projection that is associated with the respective angle by: storing, in data elements associated with locations of the detector within the second region, values from corresponding data elements (e.g., that are associated with a same location on the detector) of the corresponding truncated projection (e.g., associated with a same angle) of the truncated sinogram; and storing, in data elements associated with locations of the detector outside of the second region but within the first region, values from corresponding data elements (e.g., that are associated with a same location on the detector) of the interpolated projection (e.g., associated with a same angle); (iii) determining, by the processor, a back-projection of the combined projection, (e.g., filtering the combined projection then back-projecting the filtered combined projection); and (iv) updating, by the processor, the 3D dataset by combining the back-projection of the combined projection with the 3D dataset (e.g., summing data representing the determined back-projection with the 3D dataset), such that once all angles are processed, the 3D dataset represents a 3D image of the subject.

In certain embodiments, the method comprises performing step (c) such that it is only necessary to store one combined projection in memory (e.g., random access memory (RAM)) at a time (e.g., by, for each angle of a plurality of angles, processing projections associated with the angle such that only one combined projection needs to be determined and stored in memory).

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the method comprises: acquiring, via a first multi-angle scan of the subject, a plurality of downsampled projections to obtain the downsampled sinogram; and acquiring, via a second multi-angle scan of the subject, a plurality of truncated projections to obtain the truncated sinogram.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, the method comprises, for each of a plurality of angles of a multi-angle scan of the subject (e.g., a multi-angle CT scan): acquiring a corresponding initial projection that stores data representing signals from a first region of the detector (e.g., the full detector area); downsampling, by the processor, the acquired projection to a reduced resolution, thereby obtaining a downsampled projection having a resolution that is lower than that of the initial projection (e.g., such that the downsampled projection takes up less memory than the initial projection); storing, by the processor, the downsampled projection as a projection of the downsampled sinogram; cropping, by the processor, the initial projection to obtain a truncated projection that stores data representing signals from a region of the detector that is a subregion of the first region smaller than the first region [e.g., by removing data elements associated with locations of the detector outside the subregion; e.g., by setting values of data elements associated with locations of the detector outside of the subregion to a constant value (e.g., 0; e.g., a 'null'); e.g., such that the truncated projection takes up less memory than the initial projection]; and storing the truncated projection as a projection of the truncated sinogram.

In certain embodiments, the processor comprises one or more processing units of a first type (e.g., central processing units (CPUs)) and one or more processing units of a second type (e.g., graphics processing units (GPUs)). In certain embodiments, steps (a) and (b) are performed by one or more processing units of the first type (e.g., central processing units (CPUs)) and step (c) is performed by one or more processing units of the second type (e.g., graphics processing units (GPUs)).

In certain embodiments, the second region of the detector is predefined (e.g., via a configuration in a CT scanner used to obtain a multi-angle scan of the object).

In certain embodiments, the method comprises: identifying, by the processor (e.g., automatically; e.g., via a user interaction), within an image of the subject (e.g., a previously obtained image; e.g., an optical image; e.g., a fluorescence image, a bioluminescence image, or other light based image; e.g., a low resolution image of the subject obtained (e.g., via tomographic reconstruction) using the downsampled sinogram) a region of interest (ROI); and determining, by the processor, the second region of the detector based on the identified ROI (e.g., such that the field of view of the second region corresponds to the ROI).

In another aspect, the invention is directed to a method of automated sinogram completion (e.g. where the sinogram to be completed is truncated due to a subvolume crop), the method comprising the steps of: (a) accessing (e.g., and/or acquiring), by a processor of a computing device, a downsampled sinogram (e.g., a low-resolution global sinogram; e.g., $S_{4\times4}$ from full panel bin 4 projections) comprising data recorded during multi-angle scanning of a subject; (b) accessing (e.g., and/or acquiring), by the processor, projections (e.g. bin 1 projections) comprising data recorded during multi-angle scanning of the subject, and storing data from the projections corresponding to (e.g., limited to) an angle dependent projected region of interest (ROI) of the subject, wherein, for a given angle associated with a given projection, the projected region of interest for the given angle corresponds to a specific region of a detector that maps to a fixed ROI within the subject (e.g., for a given angle, the projected ROI is the projection of the fixed ROI within the subject onto the detector area for that angle), thereby obtaining a truncated sinogram (e.g., a high-resolution local sinogram; e.g., $S_{1\times1,RoiProj}$ from bin 1 projections); (c) interpolating, by the processor, each projection of the downsampled sinogram using a resolution of the truncated sinogram, thereby obtaining a plurality of interpolated projections (e.g., interpolating each projection of the downsampled sinogram with bin 1 to obtain $S_{4\times4\_to\_1\times1}$); (d) determining, by the processor, a plurality of combined projections using projections of the truncated sinogram [e.g., replacing empty columns (e.g. that correspond to projections of regions of the object outside the region of interest) in the truncated sinogram with the interpolated data (e.g. data from $S_{4\times4\_to\_1\times1}$)] to obtain combined projections (e.g., projections of a combined sinogram); and (e) creating, by the processor, a 3D image of the subject (e.g. via tomographic reconstruction) using the combined projections.

In certain embodiments, each projection of the downsampled sinogram has a first resolution [e.g., each data element of the projection is associated with N pixels of a specific location on the detector and stores a value representing signal(s) detected from the N pixels with which it is associated (e.g., N is an integer greater than or equal to 1)], and each projection of the truncated sinogram represents signal recorded across the projected region of interest for the angle with which the projection is associated and has a second resolution [e.g., each data element of the projection is associated with M pixels of a specific location on the detector and stores a value representing signal(s) detected from the M pixels with which it is associated (e.g., M is an integer greater than or equal to 1)], wherein the second resolution is higher than the first resolution (e.g., M<N).

In certain embodiments, each projection of the downsampled sinogram is interpolated based on a resolution of the truncated sinogram to convert the resolution of each projection of the downsampled sinogram to the resolution of the truncated sinogram (e.g., to convert the resolution of each projection of the downsampled sinogram from the first resolution to the second resolution).

In certain embodiments, determining each combined projection of the plurality of combined projections comprises: storing, in data elements of the combined projection that are correspond to locations of the detector outside of the projected region of interest for the angle with which the combined projection is associated, values from corresponding data elements (e.g., that are associated with a same location on the detector) of a corresponding interpolated projection (e.g., associated with a same angle); and storing, in data elements of the combined projection that correspond to locations of the detector within the projected region of interest for the angle with which the combined projection is associated, values from corresponding data elements (e.g., that are associated with a same location on the detector) of a corresponding projection (e.g., associated with a same angle) of the truncated sinogram.

In certain embodiments, the 3D image of the subject is obtained via tomographic reconstruction wherein each projection of a plurality of projections is processed individually such that, for each projection, a reconstruction sub-step is performed that (i) operates on the given projection (e.g., back-projects the projection, e.g., filters the projection then back-projects the filtered projection), and (ii) updates values of a stored 3D dataset by combining the result of (i) with the stored 3D dataset, wherein the 3D dataset is the 3D image of the subject following the processing of the plurality of projections.

In certain embodiments, the method comprises performing steps (c) through (e) such that it is only necessary to store one combined projection in memory (e.g., random access memory (RAM)) at a time (e.g., by, for each angle of a plurality of angles, processing projections associated with the angle such that only one combined projection needs to be determined and stored in memory).

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the method comprises: acquiring, via a first multi-angle scan of the subject, a plurality of downsampled projections to obtain the downsampled sinogram; and acquiring, via a second multi-angle scan of the subject, a plurality of truncated projections to obtain the truncated sinogram.

In certain embodiments, acquiring, via the second multi-angle, a plurality of truncated projections comprises using a variable collimator to selectively illuminate the fixed ROI within the subject.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, the method comprises, for each of a plurality of angles of a multi-angle scan of the subject (e.g., a multi-angle CT scan): acquiring a corresponding initial projection that stores data representing signals from a the full detector area; downsampling, by the processor, the acquired projection to a reduced resolution, thereby obtaining a downsampled projection having a resolution that is lower than that of the initial projection (e.g., such that the downsampled projection takes up less memory than the initial projection); storing, by the processor, the downsampled projection as a projection of the downsampled sinogram; cropping, by the processor, the initial projection to obtain a truncated projection that stores data representing signals from a region of the detector that corresponds to the projected region of interest [e.g., by removing data elements associated with locations of the detector that correspond to locations outside the projected region of interest; e.g., by setting values of data elements associated with locations of the detector corresponding to locations outside of the projected region of interest to a constant value (e.g., 0; e.g., a 'null'); e.g., such that the truncated projection takes up less memory than the initial projection]; and storing the truncated projection as a projection of the truncated sinogram.

In certain embodiments, the processor comprises one or more processing units of a first type (e.g., central processing units (CPUs)) and one or more processing units of a second type (e.g., graphics processing units (GPUs)). In certain embodiments, steps (a) and (b) are performed by one or more processing units of the first type (e.g., central processing units (CPUs)) and steps (c) through (e) are performed by one or more processing units of the second type (e.g., graphics processing units (GPUs)).

In certain embodiments, the ROI is predefined (e.g., via a configuration in a CT scanner used to obtain a multi-angle scan of the object).

In certain embodiments, the method comprises: identifying, by the processor (e.g., automatically; e.g., via a user interaction), within an image of the subject (e.g., a previously obtained image; e.g., an optical image; e.g., a fluorescence image, a bioluminescence image, or other light based image; e.g., a low resolution image of the subject obtained (e.g., via tomographic reconstruction) using the downsampled sinogram) the region of interest (ROI).

In another aspect, the invention is directed to a method for automated sinogram completion and reconstruction (e.g., where the sinogram to be completed is truncated due to a subvolume crop), the method comprising the steps of: accessing (e.g., and/or acquiring), by a processor of a computing device, a downsampled sinogram (e.g., $S_{4\times4}$, from full panel bin 4 images); identifying, by the processor (e.g., automatically; e.g., via a user interaction), a region of interest (ROI) for a CT field of view on a low resolution CT image (e.g., wherein the low res CT image is obtained by reconstructing the downsampled sinogram, e.g., via filtered back projection (FBP) reconstruction); accessing (e.g., and/or acquiring), by the processor, truncated projections (e.g., bin 1 projections) and identifying (e.g., only saving relevant data to disk) data corresponding to an angle dependent projected region of interest (ROI) of the subject, wherein, for a given angle associated with a given projection, the projected region of interest for the given angle corresponds to a specific region of a detector that maps to the ROI (e.g., for a given angle, the projected ROI is the projection of the ROI onto the detector area for that angle) (e.g., to determine a truncated sinogram (e.g., $S_{1\times1,RoiPro}$); reconstructing, by the processor, the truncated sinogram (e.g., $S_{1\times1,RoiPro}$) to obtain a reconstructed subvolume, automatically cropping, by the processor, a portion of the reconstructed subvolume for use as an initial guess (e.g., $I_{guess}$) in a subsequent iterative reconstruction; cropping, by the processor, the low resolution CT image down to the identified ROI subvolume; interpolating, by the processor, the identified ROI subvolume to obtain an interpolated subvolume (e.g., $I_{ref}$); providing, by the processor, a model correlating image grayscale values to sinogram values (e.g., a Lambert-Beer model); and iteratively reconstructing, by the processor, the subvolume using the initial guess (e.g., $I_{guess}$), the interpolated subvolume (e.g., $I_{ref}$), and the model to obtain reconstructed image (e.g., $I_{image}$).

In certain embodiments, each projection of the downsampled sinogram has a first resolution [e.g., each data element of the projection is associated with N pixels of a specific location on the detector and stores a value representing signal(s) detected from the N pixels with which it is associated (e.g., N is an integer greater than or equal to 1)], and each projection of the truncated sinogram represents signal recorded across the projected region of interest for the angle with which the projection is associated and has a second resolution [e.g., each data element of the projection is associated with M pixels of a specific location on the detector and stores a value representing signal(s) detected from the M pixels with which it is associated (e.g., M is an integer greater than or equal to 1)], wherein the second resolution is higher than the first resolution (e.g., <1V).

In certain embodiments, each projection of the downsampled sinogram is interpolated based on a resolution of the truncated sinogram to convert the resolution of each projection of the downsampled sinogram to the resolution of the truncated sinogram (e.g., to convert the resolution of each projection of the downsampled sinogram from the first resolution to the second resolution).

In certain embodiments, determining each combined projection of the plurality of combined projections comprises: storing, in data elements of the combined projection that are correspond to locations of the detector outside of the projected region of interest for the angle with which the combined projection is associated, values from corresponding data elements (e.g., that are associated with a same location on the detector) of a corresponding interpolated projection (e.g., associated with a same angle); and storing, in data elements of the combined projection that correspond to locations of the detector within the projected region of interest for the angle with which the combined projection is associated, values from corresponding data elements (e.g., that are associated with a same location on the detector) of a corresponding projection (e.g., associated with a same angle) of the truncated sinogram.

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the method comprises: acquiring, via a first multi-angle scan of the subject, a plurality of downsampled projections to obtain the downsampled sinogram; and acquiring, via a second multi-angle scan of the subject, a plurality of truncated projections to obtain the truncated sinogram. In certain embodiments, acquiring, via the second multi-angle, a plurality of truncated projections comprises using a variable collimator to selectively illuminate the fixed ROI within the subject.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, the method comprises, for each of a plurality of angles of a multi-angle scan of the subject (e.g., a multi-angle CT scan): acquiring a corresponding initial projection that stores data representing signals from a the full detector area; downsampling, by the processor, the acquired projection to a reduced resolution, thereby obtaining a downsampled projection having a resolution that is lower than that of the initial projection (e.g., such that the downsampled projection takes up less memory than the initial projection); storing, by the processor, the downsampled projection as a projection of the downsampled sinogram; cropping, by the processor, the initial projection to obtain a truncated projection that stores data representing signals from a region of the detector that corresponds to the projected region of interest [e.g., by removing data elements associated with locations of the detector that correspond to locations outside the projected region of interest; e.g., by setting values of data elements associated with locations of the detector corresponding to locations outside of the projected region of interest to a constant value (e.g., 0; e.g., a 'null'); e.g., such that the truncated projection takes up less memory than the initial projection]; and storing the truncated projection as a projection of the truncated sinogram.

In certain embodiments, the processor comprises one or more processing units of a first type (e.g., central processing units (CPUs)) and one or more processing units of a second type (e.g., graphics processing units (GPUs)).

In another aspect, the invention is directed to a system for automated sinogram completion (e.g., where the sinogram to be completed is truncated due to a detector crop), the system comprising: a processor; and a memory having instructions stored thereon, wherein the instructions, when executed by the processor, cause the processor to: (a) accessing (e.g., and/or acquire) a downsampled sinogram (e.g., wherein each of a plurality of projections of the downsampled sinogram represents signals acquired across a first region of a detector and has a first resolution; e.g., $S_{4\times4}$, from full panel bin 4 images) comprising data recorded by a detector during multi-angle scanning (e.g., a CT scan; e.g., a first scan) of a subject; (b) access (e.g., and/or acquire) a truncated sinogram comprising data recorded by the detector during multi-angle scanning (e.g., a CT scan; e.g., a second scan; e.g., the first scan) of the subject (e.g., $S_{1\times1,trunc}$); (c) interpolate each projection of the downsampled sinogram based on a resolution of the truncated sinogram, thereby obtaining a plurality of interpolated projections (e.g., interpolating each projection of $S_{4\times4}$ with bin 1 to obtain $S_{4\times4\_to\_1\times1}$); (d) determine a plurality of combined projections using projections of the truncated sinogram and the interpolated projections [e.g., by replacing empty columns from the truncated images with interpolated data (e.g., replacing empty columns in $S_{1\times1,trunc}$ with interpolated data from $S_{4\times4\_to\_1\times1}$) to obtain combined projections (e.g., projections of a combined sinogram, $S_{combined}$)]; and (e) create a 3D image of the subject (e.g., via tomographic reconstruction) using the combined projections.

In certain embodiments, each projection of the downsampled sinogram represents signals recorded across a first region of a detector (e.g., recorded for a given angle of a multi-angle scan of the subject) and has a first resolution [e.g., each data element of the projection is associated with N pixels of a specific location on the detector and stores a value representing signal(s) detected from the N pixels with which it is associated (e.g., N is an integer greater than or equal to 1)], and each projection of the truncated sinogram represents signals from recorded across a second region of the detector (e.g., recorded for a given angle of a multi-angle scan of the subject) and has a second resolution [e.g., each data element of the projection is associated with M pixels of a specific location on the detector and stores a value representing signal(s) detected from the M pixels with which it is associated (e.g., M is an integer greater than or equal to 1)], wherein the second region is a sub-region of the first region and the second resolution is higher than the first resolution (e.g., M<N).

In certain embodiments, each projection of the downsampled sinogram is interpolated based on a resolution of the truncated sinogram to convert the resolution of each projection of the downsampled sinogram to the resolution of the truncated sinogram (e.g., to convert the resolution of each projection of the downsampled sinogram from the first resolution to the second resolution).

In certain embodiments, the instructions cause the processor to determine each combined projection of the plurality of combined projections by: storing, in data elements of the combined projection that are associated with locations of the detector that are within a first region of the detector but outside of a second region of the detector, values from corresponding data elements (e.g., that are associated with a same location on the detector) of a corresponding interpolated projection (e.g., associated with a same angle), wherein each projection of the downsampled sinogram stores data representing signals from a first region and each projection of the truncated sinogram stores data representing signals from the second region; and storing, in data elements of the combined projection that are associated with locations of the detector within the second region, values from corresponding data elements (e.g., that are associated with a same location on the detector) of a corresponding projection (e.g., associated with a same angle) of the truncated sinogram.

In certain embodiments, the 3D image of the subject is obtained via tomographic reconstruction wherein the instructions cause the processor to process each projection of a plurality of projections individually such that, for each projection, a reconstruction sub-step is performed that (i) operates on the given projection (e.g., back-projects the projection, e.g., filters the projection then back-projects the filtered projection), and (ii) updates values of a stored 3D dataset by combining the result of (i) with the stored 3D dataset, wherein the 3D dataset is the 3D image of the subject following the processing of the plurality of projections.

In certain embodiments, the instructions cause the processor to perform steps (c) through (e) such that it is only necessary to store one combined projection in memory (e.g., random access memory (RAM)) at a time (e.g., by, for each angle of a plurality of angles, processing projections associated with the angle such that only one combined projection needs to be determined and stored in memory).

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the instructions cause the processor to: acquire, via a first multi-angle scan of the subject, a plurality of downsampled projections to obtain the downsampled sinogram; and acquire, via a second multi-angle scan of the subject, a plurality of truncated projections to obtain the truncated sinogram.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, for each of a plurality of angles of a multi-angle scan of the subject (e.g., a multi-angle CT scan), the instructions cause the processor to: acquire a corresponding initial projection that stores data representing signals from a first region of the detector (e.g., the full detector area); downsample the acquired projection to a reduced resolution, thereby obtaining a downsampled projection having a resolution that is lower than that of the initial projection (e.g., such that the downsampled projection takes up less memory than the initial projection); store the downsampled projection as a projection of the downsampled sinogram; crop the initial projection to obtain a truncated projection that stores data representing signals from a region of the detector that is a subregion of the first region smaller than the first region [e.g., by removing data elements associated with locations of the detector outside the subregion; e.g., by setting values of data elements associated with locations of the detector outside of the subregion to a constant value (e.g., 0; e.g., a 'null'); e.g., such that the truncated projection takes up less memory than the initial projection]; and store the truncated projection as a projection of the truncated sinogram.

In certain embodiments, the processor comprises one or more processing units of a first type (e.g., central processing units (CPUs)) and one or more processing units of a second type (e.g., graphics processing units (GPUs)).

In certain embodiments, steps (a) and (b) are performed by one or more processing units of the first type (e.g., central processing units (CPUs)) and steps (c) through (e) are performed by one or more processing units of the second type (e.g., graphics processing units (GPUs)).

In certain embodiments, the second region of the detector is predefined (e.g., via a configuration in a CT scanner used to obtain a multi-angle scan of the object).

In certain embodiments, the instructions cause the processor to: identify (e.g., automatically; e.g., via a user interaction), within an image of the subject (e.g., a previously obtained image; e.g., an optical image; e.g., a fluorescence image, a bioluminescence image, or other light based image; e.g., a low resolution image of the subject obtained (e.g., via tomographic reconstruction) using the downsampled sinogram) a region of interest (ROI); and determine the second region of the detector based on the identified ROI (e.g., such that the field of view of the second region corresponds to the ROI).

In certain embodiments, the system further comprises a CT scanner (e.g., a microCT scanner) (e.g., comprising an X-ray source and an X-ray detector) for acquiring the projections of a subject. In certain embodiments, the CT scanner comprises a rotating gantry or a rotating turntable (e.g., for stable, revolving horizontal motion). In certain embodiments, the system further comprises an operating console.

In certain embodiments, the system further comprises an optical image acquisition subsystem (e.g., comprising an optical detector for obtaining a photograph, e.g., a fluorescence and/or bioluminescence image of the subject). In certain embodiments, the system further comprises a nuclear imaging (e.g. PET, e.g. SPECT) imaging system.

In certain embodiments, the optical image acquisition subsystem further comprises an excitation light source (e.g., for exciting a fluorophore in the subject being imaged to produce fluorescence that is detected by the optical detector).

In another aspect, the invention is directed to a system for automated sinogram completion (e.g., where the sinogram to be completed is truncated due to a detector crop), the system comprising: a processor; and a memory having instructions stored thereon, wherein the instructions, when executed by the processor, cause the processor to: (a) access (e.g., and/or acquire) a downsampled sinogram (e.g., $S_{4 \times 4}$, from full panel bin 4 projections) for a subject, wherein the downsampled sinogram comprises a plurality of downsampled projections, wherein: each downsampled projection is associated with a specific angle of a multi-angle scan of the subject, each downsampled projection stores data representing signals from a first region of a detector recorded for the specific angle with which the downsampled projection is associated, and each downsampled projection has a first resolution [e.g., each data element of the projection is associated with N pixels of a specific location on the detector and stores a value representing signal(s) detected from the N pixels with which it is associated (e.g., N is an integer greater than or equal to 1)]; (b) access (e.g. and/or acquire) a truncated sinogram for the subject, wherein the truncated sinogram comprises a plurality of truncated projections, wherein: each truncated projection is associated with a specific angle of a multi-angle scan of the subject, each truncated projection stores data representing signals from a second region of a detector recorded for the specific angle with which the truncated projection is associated, wherein the second region is a sub-region of the first region, and each truncated projection has a second resolution [e.g., each data element of the projection is associated with M pixels of a specific location on the detector and stores a value representing signal(s) detected from the M pixels with which it is associated (e.g., M is an integer greater than or equal to 1)], wherein the second resolution is higher than the first resolution (e.g., M<N); (c) initialize a 3D dataset (e.g., setting all elements of the 3D dataset to 0), and, for each angle with which a downsampled projection is associated: (i) interpolate the downsampled projection to convert its resolution from the first resolution to the second resolution, thereby obtaining an interpolated projection; (ii) obtain a combined projection using data from the interpolated projection and data from a corresponding truncated projection that is associated with the respective angle by: storing, in data elements associated with locations of the detector within the second region, values from corresponding data elements (e.g., that are associated with a same location on the detector) of the corresponding truncated projection (e.g., associated with a same angle) of the truncated sinogram; and storing, in data elements associated with locations of the detector outside of the second region but within the first region, values from corresponding data elements (e.g., that are associated with a same location on the detector) of the interpolated projection (e.g., associated with a same angle); (iii) determine a back-projection of the combined projection, (e.g., filtering the combined projection then back-projecting the filtered combined projection); and (iv) update the 3D dataset by combining the back-projection of the combined projection with the 3D dataset (e.g., summing data representing the determined back-projection with the 3D dataset), such that once all angles are processed, the 3D dataset represents a 3D image of the subject.

In certain embodiments, the instructions cause the processor to perform step (c) such that it is only necessary to store one combined projection in memory (e.g., random access memory (RAM)) at a time (e.g., by, for each angle of a plurality of angles, processing projections associated with the angle such that only one combined projection needs to be determined and stored in memory).

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the instructions cause the processor to: acquire, via a first multi-angle scan of the subject, a plurality of downsampled projections to obtain the downsampled sinogram; and acquire, via a second multi-angle scan of the subject, a plurality of truncated projections to obtain the truncated sinogram.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, for each of a plurality of angles of a multi-angle scan of the subject (e.g., a multi-angle CT scan), the instructions cause the processor to: acquire a corresponding initial projection that stores data representing signals from a first region of the detector (e.g., the full detector area); downsample, the acquired projection to a reduced resolution, thereby obtaining a downsampled projection having a resolution that is lower than that of the initial projection (e.g., such that the downsampled projection takes up less memory than the initial projection); store the downsampled projection as a projection of the downsampled sinogram; crop the initial projection to obtain a truncated projection that stores data representing signals from a region of the detector that is a subregion of the first region smaller than the first region [e.g., by removing data elements associated with locations of the detector outside the subregion; e.g., by setting values of data elements associated with locations of the detector outside of the subregion to a constant value (e.g., 0; e.g., a 'null'); e.g., such that the truncated projection takes up less memory than the initial projection]; and store the truncated projection as a projection of the truncated sinogram.

In certain embodiments, the processor comprises one or more processing units of a first type (e.g., central processing units (CPUs)) and one or more processing units of a second type (e.g., graphics processing units (GPUs)).

In certain embodiments, steps (a) and (b) are performed by one or more processing units of the first type (e.g., central processing units (CPUs)) and step (c) is performed by one or more processing units of the second type (e.g., graphics processing units (GPUs)).

In certain embodiments, the second region of the detector is predefined (e.g., via a configuration in a CT scanner used to obtain a multi-angle scan of the object).

In certain embodiments, the instructions cause the processor to: identify (e.g., automatically; e.g., via a user interaction), within an image of the subject (e.g., a previously obtained image; e.g., an optical image; e.g., a fluorescence image, a bioluminescence image, or other light based image; e.g., a low resolution image of the subject obtained (e.g., via tomographic reconstruction) using the downsampled sinogram) a region of interest (ROI); and determine the second region of the detector based on the identified ROI (e.g., such that the field of view of the second region corresponds to the ROI).

In certain embodiments, the system further comprises a CT scanner (e.g., a microCT scanner) (e.g., comprising an X-ray source and an X-ray detector) for acquiring the projections of a subject. In certain embodiments, the CT scanner comprises a rotating gantry or a rotating turntable (e.g., for stable, revolving horizontal motion). In certain embodiments, the system further comprises an operating console.

In certain embodiments, the system further comprises an optical image acquisition subsystem (e.g., comprising an optical detector for obtaining a photograph, e.g., a fluorescence and/or bioluminescence image of the subject). In certain embodiments, the system further comprises a nuclear imaging (e.g. PET, e.g. SPECT) imaging system.

In certain embodiments, the optical image acquisition subsystem further comprises an excitation light source (e.g., for exciting a fluorophore in the subject being imaged to produce fluorescence that is detected by the optical detector).

In another aspect, the invention is directed to a system for automated sinogram completion (e.g. where the sinogram to be completed is truncated due to a subvolume crop), the system comprising: a processor; and a memory having instructions stored thereon, wherein the instructions, when executed by the processor, cause the processor to: (a) access (e.g., and/or acquire) a downsampled sinogram (e.g., a low-resolution global sinogram; e.g., $S_{4\times4}$ from full panel bin 4 projections) comprising data recorded during multi-angle scanning of a subject; (b) access (e.g., and/or acquire) projections (e.g. bin 1 projections) comprising data recorded during multi-angle scanning of the subject, and storing data from the projections corresponding to (e.g., limited to) an angle dependent projected region of interest (ROI) of the subject, wherein, for a given angle associated with a given projection, the projected region of interest for the given angle corresponds to a specific region of a detector that maps to a fixed ROI within the subject (e.g., for a given angle, the projected ROI is the projection of the fixed ROI within the subject onto the detector area for that angle), thereby obtaining a truncated sinogram (e.g., a high-resolution local sinogram; e.g., $S_{1\times1,RoiPro}$ from bin 1 projections); (c) interpolate each projection of the downsampled sinogram using a resolution of the truncated sinogram, thereby obtaining a plurality of interpolated projections (e.g., interpolating each projection of the downsampled sinogram with bin 1 to obtain $S_{4\times4\_to\_1\times1}$); (d) determine a plurality of combined projections using projections of the truncated sinogram [e.g., replacing empty columns (e.g. that correspond to projections of regions of the object outside the region of interest) in the truncated sinogram with the interpolated data (e.g. data from $S_{4\times4\_to\_1\times1}$)] to obtain combined projections (e.g., projections of a combined sinogram); and (e) create a 3D image of the subject (e.g. via tomographic reconstruction) using the combined projections.

In certain embodiments, each projection of the downsampled sinogram has a first resolution [e.g., each data element of the projection is associated with N pixels of a specific location on the detector and stores a value representing signal(s) detected from the N pixels with which it is associated (e.g., N is an integer greater than or equal to 1)], and each projection of the truncated sinogram represents signal recorded across the projected region of interest for the angle with which the projection is associated and has a second resolution [e.g., each data element of the projection is associated with M pixels of a specific location on the detector and stores a value representing signal(s) detected from the M pixels with which it is associated (e.g., M is an integer greater than or equal to 1)], wherein the second resolution is higher than the first resolution (e.g., M<N).

In certain embodiments, each projection of the downsampled sinogram is interpolated based on a resolution of the truncated sinogram to convert the resolution of each projection of the downsampled sinogram to the resolution of the truncated sinogram (e.g., to convert the resolution of each projection of the downsampled sinogram from the first resolution to the second resolution).

In certain embodiments, the instructions cause the processor to determine each combined projection of the plurality of combined projections by: storing, in data elements of the combined projection that are correspond to locations of the detector outside of the projected region of interest for the angle with which the combined projection is associated, values from corresponding data elements (e.g., that are associated with a same location on the detector) of a corresponding interpolated projection (e.g., associated with a same angle); and storing, in data elements of the combined projection that correspond to locations of the detector within the projected region of interest for the angle with which the combined projection is associated, values from corresponding data elements (e.g., that are associated with a same location on the detector) of a corresponding projection (e.g., associated with a same angle) of the truncated sinogram.

In certain embodiments, the 3D image of the subject is obtained via tomographic reconstruction wherein each projection of a plurality of projections is processed individually such that, for each projection, a reconstruction sub-step is performed that (i) operates on the given projection (e.g., back-projects the projection, e.g., filters the projection then back-projects the filtered projection), and (ii) updates values of a stored 3D dataset by combining the result of (i) with the stored 3D dataset, wherein the 3D dataset is the 3D image of the subject following the processing of the plurality of projections.

In certain embodiments, the instructions cause the processor to perform steps (c) through (e) such that it is only necessary to store one combined projection in memory (e.g., random access memory (RAM)) at a time (e.g., by, for each angle of a plurality of angles, processing projections associated with the angle such that only one combined projection needs to be determined and stored in memory).

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the instructions cause the processor to: acquire, via a first multi-angle scan of the subject, a plurality of downsampled projections to obtain the downsampled sinogram; and acquire, via a second multi-angle scan of the subject, a plurality of truncated projections to obtain the truncated sinogram.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, for each of a plurality of angles of a multi-angle scan of the subject (e.g., a multi-angle CT scan), the instructions cause the processor to: acquire a corresponding initial projection that stores data representing signals from a the full detector area; downsample the acquired projection to a reduced resolution, thereby obtaining a downsampled projection having a resolution that is lower than that of the initial projection (e.g., such that the downsampled projection takes up less memory than the initial projection); store the downsampled projection as a projection of the downsampled sinogram; crop the initial projection to obtain a truncated projection that stores data representing signals from a region of the detector that corresponds to the projected region of interest [e.g., by removing data elements associated with locations of the detector that correspond to locations outside the projected region of interest; e.g., by setting values of data elements associated with locations of the detector corresponding to locations outside of the projected region of interest to a constant value (e.g., 0; e.g., a 'null'); e.g., such that the truncated projection takes up less memory than the initial projection]; and store the truncated projection as a projection of the truncated sinogram.

In certain embodiments, the processor comprises one or more processing units of a first type (e.g., central processing units (CPUs)) and one or more processing units of a second type (e.g., graphics processing units (GPUs)).

In certain embodiments, steps (a) and (b) are performed by one or more processing units of the first type (e.g., central processing units (CPUs)) and steps (c) through (e) are performed by one or more processing units of the second type (e.g., graphics processing units (GPUs)).

In certain embodiments, the ROI is predefined (e.g., via a configuration in a CT scanner used to obtain a multi-angle scan of the object).

In certain embodiments, the instructions cause the processor to: identify (e.g., automatically; e.g., via a user interaction), within an image of the subject (e.g., a previously obtained image; e.g., an optical image; e.g., a fluorescence image, a bioluminescence image, or other light based image; e.g., a low resolution image of the subject obtained (e.g., via tomographic reconstruction) using the downsampled sinogram), the region of interest (ROI).

In certain embodiments, the system further comprises a CT scanner (e.g., a microCT scanner) (e.g., comprising an X-ray source and an X-ray detector) for acquiring the projections of a subject. In certain embodiments, the CT scanner comprises a rotating gantry or a rotating turntable (e.g., for stable, revolving horizontal motion). In certain embodiments, the system further comprises an operating console.

In certain embodiments, the system further comprises an optical image acquisition subsystem (e.g., comprising an optical detector for obtaining a photograph, e.g., a fluorescence and/or bioluminescence image of the subject). In certain embodiments, the system further comprises a nuclear imaging (e.g. PET, e.g. SPECT) imaging system.

In certain embodiments, the optical image acquisition subsystem further comprises an excitation light source (e.g., for exciting a fluorophore in the subject being imaged to produce fluorescence that is detected by the optical detector).

In certain embodiments, the CT scanner comprises an X-ray source, and X-ray detector, and an adjustable collimator positioned in between the X-ray source and X-ray detector (e.g., immediately following the X-ray source; e.g., in between the X-ray source and a subject to be scanned), wherein: the adjustable collimator comprises: a first set of adjustable shutters (e.g., two vertically oriented shutters; e.g., that are substantially opaque to X-ray radiation) whose position(s) are movable along a first axis, such that a variable portion of a beam of X-ray radiation passing from the X-ray source to the X-ray detector is cropped along the first axis (e.g., along an x-axis); and a second set of adjustable shutters (e.g., two horizontally oriented shutters; e.g., that are substantially opaque to X-ray radiation) whose position(s) are movable along a second axis, such that a variable portion of the X-ray beam is cropped along the second axis (e.g., along a y-axis; e.g., wherein the second axis is orthogonal to the first axis), and the adjustable collimator is operable to move as a function of angle during multi-angle scanning of a subject (e.g., the adjustable collimator is mounted on an adjustable mount that slides as a function of angle during multi-angle scanning)(e.g., such that a constant sub-region of a subject is transilluminated with X-ray radiation during multi-angle scanning).

In another aspect, the invention is directed to a system for automated sinogram completion and reconstruction (e.g., where the sinogram to be completed is truncated due to a subvolume crop), the system comprising: a processor; and a memory having instructions stored thereon, wherein the instructions, when executed by the processor, cause the processor to: access (e.g., and/or acquire) a downsampled sinogram (e.g., $S_{4\times4}$, from full panel bin 4 images); identify (e.g., automatically; e.g., via a user interaction), a region of interest (ROI) for a CT field of view on a low resolution CT image (e.g., wherein the low res CT image is obtained by reconstructing the downsampled sinogram, e.g., via filtered back projection (FBP) reconstruction); access (e.g., and/or acquire) truncated projections (e.g., bin 1 projections) and identify (e.g., only saving relevant data to disk) data corresponding to an angle dependent projected region of interest (ROI) of the subject, wherein, for a given angle associated with a given projection, the projected region of interest for the given angle corresponds to a specific region of a detector that maps to the ROI (e.g., for a given angle, the projected ROI is the projection of the ROI onto the detector area for that angle) (e.g., to determine a truncated sinogram (e.g., $S_{1\times1,RoiPro}$); reconstruct the truncated sinogram (e.g., $S_{1\times1,RoiPro}$) to obtain a reconstructed subvolume, automatically crop a portion of the reconstructed subvolume for use as an initial guess (e.g., $I_{guess}$) in a subsequent iterative reconstruction; crop the low resolution CT image down to the identified ROI subvolume; interpolate the identified ROI subvolume to obtain an interpolated subvolume (e.g., $I_{ref}$); provide a model correlating image grayscale values to sinogram values (e.g., a Lambert-Beer model); and iteratively reconstruct the subvolume using the initial guess (e.g., $I_{guess}$), the interpolated subvolume (e.g., $I_{ref}$), and the model to obtain reconstructed image (e.g., $I_{image}$).

In certain embodiments, each projection of the downsampled sinogram has a first resolution [e.g., each data element of the projection is associated with N pixels of a specific location on the detector and stores a value representing signal(s) detected from the N pixels with which it is associated (e.g., N is an integer greater than or equal to 1)], and each projection of the truncated sinogram represents signal recorded across the projected region of interest for the angle with which the projection is associated and has a second resolution [e.g., each data element of the projection is associated with M pixels of a specific location on the detector and stores a value representing signal(s) detected from the M pixels with which it is associated (e.g., M is an integer greater than or equal to 1)], wherein the second resolution is higher than the first resolution (e.g., M<N).

In certain embodiments, each projection of the downsampled sinogram is interpolated based on a resolution of the truncated sinogram to convert the resolution of each projection of the downsampled sinogram to the resolution of the truncated sinogram (e.g., to convert the resolution of each projection of the downsampled sinogram from the first resolution to the second resolution).

In certain embodiments, the instructions cause the processor to determine each combined projection of the plurality of combined projections by: storing, in data elements of the combined projection that are correspond to locations of the detector outside of the projected region of interest for the angle with which the combined projection is associated, values from corresponding data elements (e.g., that are associated with a same location on the detector) of a corresponding interpolated projection (e.g., associated with a same angle); and storing, in data elements of the combined projection that correspond to locations of the detector within the projected region of interest for the angle with which the combined projection is associated, values from corresponding data elements (e.g., that are associated with a same location on the detector) of a corresponding projection (e.g., associated with a same angle) of the truncated sinogram.

In certain embodiments, the downsampled sinogram comprises a plurality of downsampled projections acquired (e.g., previously) using a first multi-angle scan of the subject and the truncated sinogram comprises a plurality of truncated projections acquired (e.g., previously) using a second multi-angle scan of the subject.

In certain embodiments, the instructions cause the processor to: acquire, via a first multi-angle scan of the subject, a plurality of downsampled projections to obtain the downsampled sinogram; and acquire, via a second multi-angle scan of the subject, a plurality of truncated projections to obtain the truncated sinogram.

In certain embodiments, both the downsampled sinogram and the truncated sinogram are obtained using a single (e.g., high resolution) multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

In certain embodiments, for each of a plurality of angles of a multi-angle scan of the subject (e.g., a multi-angle CT scan), the instructions cause the processor to: acquire a corresponding initial projection that stores data representing signals from a the full detector area; downsample the acquired projection to a reduced resolution, thereby obtaining a downsampled projection having a resolution that is lower than that of the initial projection (e.g., such that the downsampled projection takes up less memory than the initial projection); store the downsampled projection as a projection of the downsampled sinogram; crop the initial projection to obtain a truncated projection that stores data representing signals from a region of the detector that corresponds to the projected region of interest [e.g., by removing data elements associated with locations of the detector that correspond to locations outside the projected region of interest; e.g., by setting values of data elements associated with locations of the detector corresponding to locations outside of the projected region of interest to a constant value (e.g., 0; e.g., a 'null'); e.g., such that the truncated projection takes up less memory than the initial projection]; and store the truncated projection as a projection of the truncated sinogram.

In certain embodiments, the processor comprises one or more processing units of a first type (e.g., central processing units (CPUs)) and one or more processing units of a second type (e.g., graphics processing units (GPUs)).

In certain embodiments, the system further comprises a CT scanner (e.g., a microCT scanner) (e.g., comprising an X-ray source and an X-ray detector) for acquiring the projections of a subject. In certain embodiments, the CT scanner comprises a rotating gantry or a rotating turntable (e.g., for stable, revolving horizontal motion). In certain embodiments, the system further comprises an operating console.

In certain embodiments, the system further comprises an optical image acquisition subsystem (e.g., comprising an optical detector for obtaining a photograph, e.g., a fluorescence and/or bioluminescence image of the subject). In certain embodiments, the system further comprises a nuclear imaging (e.g. PET, e.g. SPECT) imaging system.

In certain embodiments, the optical image acquisition subsystem further comprises an excitation light source (e.g., for exciting a fluorophore in the subject being imaged to produce fluorescence that is detected by the optical detector).

In certain embodiments, the CT scanner comprises an X-ray source, and X-ray detector, and an adjustable collimator positioned in between the X-ray source and X-ray detector (e.g., immediately following the X-ray source; e.g., in between the X-ray source and a subject to be scanned), wherein: the adjustable collimator comprises: a first set of adjustable shutters (e.g., two vertically oriented shutters; e.g., that are substantially opaque to X-ray radiation) whose position(s) are movable along a first axis, such that a variable portion of a beam of X-ray radiation passing from the X-ray source to the X-ray detector is cropped along the first axis (e.g., along an x-axis); and a second set of adjustable shutters (e.g., two horizontally oriented shutters; e.g., that are substantially opaque to X-ray radiation) whose position(s) are movable along a second axis, such that a variable portion of the X-ray beam is cropped along the second axis (e.g., along a y-axis; e.g., wherein the second axis is orthogonal to the first axis), and the adjustable collimator is operable to move as a function of angle during multi-angle scanning of a subject (e.g., the adjustable collimator is mounted on an adjustable mount that slides as a function of angle during multi-angle scanning)(e.g., such that a constant sub-region of a subject is transilluminated with X-ray radiation during multi-angle scanning).

In another aspect, the invention is directed to a method for automated sinogram completion (e.g., where the sinogram to be completed is truncated due to a detector crop), the method comprising the steps of: identifying (e.g., automatically identifying), by a processor of a computing device, a region of interest (ROI) on a photograph to determine a maximum object size $d_{max}$; optionally, identifying (e.g., automatically identifying), by the processor, a region of interest for a CT field of view on a photograph (e.g., the same photograph as the previous step), $d_{FOV}$ (alternatively, $d_{FOV}$ may be pre-defined in CT configuration); accessing (e.g., and/or acquiring) truncated projections using the ROI (e.g., to determine $S_{1\times1,trunc}$); determining, by the processor, limiting columns, $LIM_{object}$, for a sinogram by projection of $d_{max}$ into x-ray detector space; replacing, by the processor, empty columns from the truncated projections (e.g., empty columns in $S_{1\times1,trunc}$) by extrapolating to limiting edges $LIM_{object}$ to obtain a completed sinogram $S_{padded}$; and creating, by the processor, a 3D image of the a subject (e.g., via tomographic reconstruction) using projections of the completed sinogram.

In another aspect, the invention is directed to a method for automated sinogram completion (e.g., where the sinogram to be completed is truncated due to a detector crop), the method comprising the steps of: accessing (e.g., and/or acquiring), by a processor of a computing device, a downsampled sinogram (e.g., $S_{4\times4}$, from full panel bin 4 images); optionally, identifying (e.g., automatically identifying), by the processor, a region of interest (ROI) for a CT field of view on a photograph (e.g., alternatively, ROI could be pre-defined in CT configuration) (e.g., by identifying an initial 2D ROI is within the photograph in two dimensional Cartesian coordinates and mapping the initial 2D ROI into a three dimensional CT space using a transformation matrix, thereby identifying the ROI for the CT field of view); accessing (e.g., and/or acquiring), by the processor, trun-cated projections using the ROI (e.g., to determine $S_{1\times1,trunc}$); interpolating, by the processor, the downsampled sinogram using the truncated projections (e.g., interpolate each projection in $S_{4\times4}$ with bin 1 to obtain $S_{4\times4\_to\_1\times1}$); replacing, by the processor, data in truncated rows from the truncated projections with summed data outside of truncation limits from the interpolated data (e.g., replacing data in truncated rows of $S_{1\times1,trunc}$ with summed data outside of truncation limits for $S_{4\times4\_to\_1\times1}$) to obtain a summed sinogram (e.g., $S_{sum,trunc}$); and obtaining, by the processor, a 3D image of the subject (e.g., via tomographic reconstruction) using projections of the summed sinogram.

In another aspect, the invention is directed to a method for applying post processing corrections to a sinogram truncated due to a detector crop, the method comprising the steps of: accessing (e.g., and/or acquiring), by a processor of a computing device, a truncated sinogram $S_{trunc}$ (e.g., a truncated bin 1 sinogram); reconstructing, by the processor, the truncated sinogram to obtain $I_{trunc}$; creating, by the processor, a summed truncated sinogram and reconstructing the summed truncated sinogram to obtain $I_{tsum,trunc}$; and combining, by the processor, $I_{trunc}$ with $I_{tsum,trunc}$ (e.g., determine a pixel by pixel mean).

In another aspect, the invention is directed to a method for automated sinogram completion (e.g., where the sinogram to be completed is truncated due to a subvolume crop), the method comprising the steps of: identifying (e.g., automatically identifying), by a processor of a computing device, a maximum object size $d_{max}$ from a photograph; identifying (e.g., automatically identifying), by the processor, a region of interest (ROI) for a CT field of view on a photograph (e.g., the same photograph as the previous step) (e.g., wherein the region of interest is a small portion of the photograph (e.g., <30% of the area $d_{max}\times d_{max}$)) (e.g., by identifying an initial 2D ROI is within the photograph in two dimensional Cartesian coordinates and mapping the initial 2D ROI into a three dimensional CT space using a transformation matrix, thereby identifying the ROI for the CT field of view); accessing (e.g, and/or acquiring), by the processor truncated projections (e.g., bin 1 projections) and identifying (e.g., only saving relevant data to disk) data from the projected ROI to determine $S_{1\times1,RoiPro}$; determining, by the processor, limiting columns, $LIM_{object}$, for a sinogram by projection of $d_{max}$ into x-ray detector space; replacing, by the processor, empty columns from the truncated images (empty columns in $S_{1\times1,RoiPro}$) by extending edges to limiting edges $LIM_{object}$ (e.g., via extrapolation) to obtain a completed sinogram $S_{padded}$; and creating, by the processor, a 3D image of the subject (e.g., via tomographic reconstruction) using projections of the completed sinogram.

In another aspect, the invention is directed to a system for automated sinogram completion (e.g., where the sinogram to be completed is truncated due to a detector crop), the system comprising: a processor; and a memory having instructions stored thereon, wherein the instructions, when executed by the processor, cause the processor to: identify (e.g., automatically identifying) a region of interest (ROI) on a photograph to determine a maximum object size $d_{max}$; optionally, identify (e.g., automatically identify) a region of interest for a CT field of view on a photograph (e.g., the same photograph as the previous step), $d_{FOV}$ (alternatively, $d_{FOV}$ may be pre-defined in CT configuration); access (e.g., and/or acquire) truncated projections using the ROI (e.g., to determine $S_{1\times1,trunc}$); determine limiting columns, $LIM_{object}$, for a sinogram by projection of $d_{max}$ into x-ray detector space; replace empty columns from the truncated projections (e.g., empty columns in $S_{1\times1,trunc}$) by extrapolating to limiting edges $LIM_{object}$ to obtain a completed sinogram $S_{padded}$; and create a 3D image of the a subject (e.g., via tomographic reconstruction) using projections of the completed sinogram.

In another aspect, the invention is directed to a system for automated sinogram completion (e.g., where the sinogram to be completed is truncated due to a detector crop), the system comprising: a processor; and a memory having instructions stored thereon, wherein the instructions, when executed by the processor, cause the processor to: access (e.g., and/or acquire) a downsampled sinogram (e.g., $S_{4\times 4}$, from full panel bin 4 images); optionally, identify (e.g., automatically identify) a region of interest (ROI) for a CT field of view on a photograph (e.g., alternatively, ROI could be pre-defined in CT configuration) (e.g., by identifying an initial 2D ROI is within the photograph in two dimensional Cartesian coordinates and mapping the initial 2D ROI into a three dimensional CT space using a transformation matrix, thereby identifying the ROI for the CT field of view); access (e.g., and/or acquire) truncated projections using the ROI (e.g., to determine $S_{1\times 1, trunc}$); interpolate the downsampled sinogram using the truncated projections (e.g., interpolate each projection in $S_{4\times 4}$ with bin 1 to obtain $S_{4\times 4\_to\_1\times 1}$); replace data in truncated rows from the truncated projections with summed data outside of truncation limits from the interpolated data (e.g., replacing data in truncated rows of $S_{1\times 1, trunc}$ with summed data outside of truncation limits for $S_{4\times 4\_to\_1\times 1}$) to obtain a summed sinogram (e.g., $S_{sum, trunc}$); and obtain a 3D image of the subject (e.g., via tomographic reconstruction) using projections of the summed sinogram.

In another aspect, the invention is directed to a system for applying post processing corrections to a sinogram truncated due to a detector crop, the system comprising: a processor; and a memory having instructions stored thereon, wherein the instructions, when executed by the processor, cause the processor to: access (e.g., and/or acquire) a truncated sinogram $S_{trunc}$ (e.g., a truncated bin 1 sinogram); reconstruct the truncated sinogram to obtain $I_{trunc}$; create a summed truncated sinogram and reconstructing the summed truncated sinogram to obtain $I_{tsum,trunc}$; and combine $I_{trunc}$ with $I_{tsum,trunc}$ (e.g., determine a pixel by pixel mean).

In another aspect, the invention is directed to a system for automated sinogram completion (e.g., where the sinogram to be completed is truncated due to a subvolume crop), the system comprising: a processor; and a memory having instructions stored thereon, wherein the instructions, when executed by the processor, cause the processor to: identify (e.g., automatically identify) a maximum object size $d_{max}$ from a photograph; identify (e.g., automatically identify) a region of interest (ROI) for a CT field of view on a photograph (e.g., the same photograph as the previous step) (e.g., wherein the region of interest is a small portion of the photograph (e.g., <30% of the area $d_{max}\times d_{max}$)) (e.g., by identifying an initial 2D ROI is within the photograph in two dimensional Cartesian coordinates and mapping the initial 2D ROI into a three dimensional CT space using a transformation matrix, thereby identifying the ROI for the CT field of view); access (e.g, and/or acquire) truncated projections (e.g., bin 1 projections) and identifying (e.g., only saving relevant data to disk) data from the projected ROI to determine $S_{1\times 1, RoiPro}$; determine limiting columns, $LIM_{object}$, for a sinogram by projection of $d_{max}$ into x-ray detector space; replace empty columns from the truncated images (empty columns in $S_{1\times 1, RoiPro}$) by extending edges to limiting edges $LIM_{object}$ (e.g., via extrapolation) to obtain a completed sinogram $S_{padded}$; and create a 3D image of the subject (e.g., via tomographic reconstruction) using projections of the completed sinogram.

Embodiments described with respect to one aspect of the invention may be, applied to another aspect of the invention (e.g., features of embodiments described with respect to one independent claim are contemplated to be applicable to other embodiments of other independent claims).

DESCRIPTION OF THE DRAWINGS

The foregoing and other objects, aspects, features, and advantages of the invention will become more apparent and may be better understood by referring to the following description taken in conjunction with the accompanying drawings, in which:

FIG. 2 depicts a first truncated sinogram where the crop (centered or offset) was applied at the detector, as well as a second truncated sinogram where the crop was a subvolume crop based on a low resolution image;

DETAILED DESCRIPTION

Figure 1:
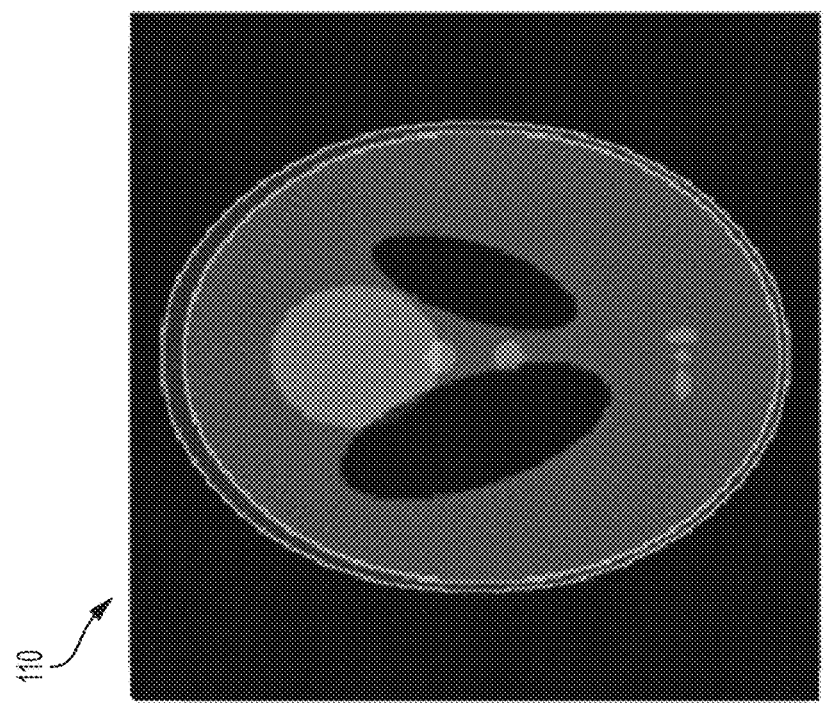
FIG. 1 is a depiction of projection data and a sinogram from a CT scan of a subject for a normal reference case where the entire object is within the field of view of a detector used to acquire projections during multi-angle scanning, according to an illustrative embodiment.
Figure 1:
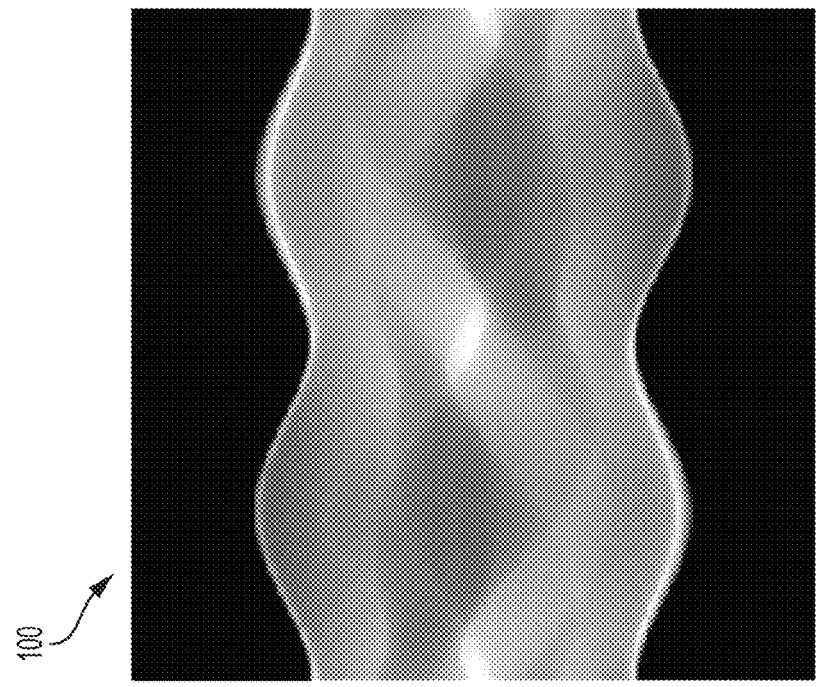

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers and sub-headers are provided for the convenience of the reader and are not intended to be limiting with respect to the claimed subject matter.

As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation.

As used herein, the term "subject" includes humans and mammals (e.g., mice, rats, pigs, cats, dogs, and horses).

The systems and methods described herein are directed to automated completion of sinograms for obtaining representations of regions of subjects. As used herein, the term "object" refers to a region of a subject.

A sinogram is a representation of projection data that is recorded by detecting transmitted X-ray radiation that passes in a substantially straight path through the sample at a plurality of angles. In certain embodiments, at a given angle, X-ray radiation transmitted through the sample is detected with a detector comprising a plurality of pixels. At a given angle, the intensity of the detected radiation varies across the detector area. The signal detected is a function of the intensity of the transmitted radiation that is detected (e.g. is substantially proportional to the intensity of the detected radiation). The raw data recorded at a given angle is referred to as a projection, and contains a series of values, each of which represents a detected signal at a given location on the detector (e.g., by a different detector pixel). By varying the angle of transmission images, a plurality of projections are recorded, each at a different angle. The particular angle at which a projection is recorded is identified by a value termed the angular parameter, $\phi$. The set of raw data comprising the plurality of projections, each of which is associated with a different angular parameter, is a sinogram.

In certain embodiments, each data element of a projection corresponds to a particular location on the detector, and stores a value that represents a detected signal at the particular location with which the data element is associated. As used herein, the term "resolution", with reference to a "projection" refers to a spatial density of the locations to which data elements of the projection correspond. In certain embodiments, the resolution of a projection is based on a number of detector pixels to which each data element of the projection corresponds. For example, in certain embodiments, each data element of a projection corresponds to a distinct detector pixel and stores a value that represents signal that is detected by that detector pixel, such that there is a one-to-one mapping between detector pixels and data elements of the projection.

In certain embodiments, lower resolution projections are obtained, such that each data element of a projection corresponds to a set (e.g., a unique set) of a plurality of detector pixels. For example, data from multiple adjacent pixels of a detector may be binned together when a projection is acquired or stored, such that each data element of the projection corresponds to a set (e.g., a unique set) of one or more detector pixels. When a data element corresponds to a single pixel, it may store a value representing a signal detected by that pixel. When a data element corresponds to multiple pixels (e.g., two pixels, four pixels, sixteen pixels), it may store a value that represents an average signal detected by those pixels. For example, in certain embodiments a 2D planar array detector is used to record projections, and square arrays of adjacent pixels are binned together such that each data element of a projection corresponds to distinct square array of adjacent pixels, such as a two-by-two array (e.g., comprising four pixels), a four-by-four array (e.g., comprising sixteen pixels), and the like. As used herein, the term "bin" with reference to an integer number, as in "bin N", where N is an integer, is used to refer to the length (in number of pixels) of a side of a square array of pixels to which data elements of a given projection correspond. For example, a bin 4 projection refers to a projection for which each data element of the projection corresponds to a four by four square array of pixels. The term "bin 1" refers a projection in which each data element corresponds to an individual detector pixel.

In certain embodiments, other groupings of detector pixels are possible. For example, rectangular groupings may be used.

In certain embodiments, projections are directly acquired from a scanning device (e.g., a CT scanner) at a given resolution. For example, an X-ray detector may perform averaging of pixels and output bin N projections as described above directly. In certain embodiments, once acquired from an X-ray detector, projections are downsampled to reduce their resolution. For example, a bin 1 projection may be acquired, and downsampled by a processor (e.g., a central processing unit (CPU)) by averaging values stored four-by-four arrays of adjacent data elements in order to obtain a bin 4 projection.

In certain embodiments, projections are recorded using a linear array detector that comprises a single row of pixels, such that each projection can be represented as a 1D data array. In this case, each element of the array corresponds to a particular pixel, or a particular distance along the linear detector (e.g., a distance along a projection direction). In certain embodiments, projections are recorded using a two-dimensional planar array detector, such that each projection can be represented as a 2D dataset, with each dimension of the dataset corresponding to a dimension of the detector (e.g., a first dimension corresponding to a distance along an x-axis of the detector and a second dimension corresponding to a distance along a y-axis of the detector; e.g., a first dimension corresponding to a column number of an array of pixels of the detector and a second dimension corresponding to a row number of an array of pixels of the detector). In certain embodiments, it is not necessary for the dimensionality of a projection dataset to correspond directly to the dimensionality of the detector, so long as the correspondence between data elements of the projection and locations of the detector (e.g., pixels of the detector) is identifiable. For example, projections recorded using a 2D planar array detector may be represented as 1D datasets, with each data element of the projections corresponding to a particular set of one or more detector pixels.

A sinogram contains a plurality of projections, each projection associated with a specific angle of a multi-angle scan (e.g., a CT scan) of a subject. In certain embodiments, each projection of a given sinogram has the same resolution. Accordingly, as used herein, the term "resolution" when used in reference to a sinogram refers to the resolution of each projection of the sinogram. In certain embodiments, a sinogram is represented as a dataset with one dimension corresponding to the angular parameter, and one or more additional dimensions representing dimensions of projections that the sinogram contains, such that the sinogram can be viewed as a stack of projections. For example, in certain embodiments, a sinogram is represented as 3D array of data (e.g., a data cube), with two dimensions corresponding to x- and y-directions on a 2D X-ray detector, and a third dimension representing the angular parameter, $\phi$. For example, in certain embodiments, a sinogram can be represented as a 2D array of data, with a first dimension indexing a particular pixel on the X-ray detector, and a second dimension representing the angular parameter, $\phi$.

In certain embodiments, once projection data is recorded in the form of a sinogram, the sinogram data is used to obtain a reconstruction of a cross section of the object using tomographic reconstruction techniques, such as filtered back projection (FBP).

FIG. 1 shows an example of a sinogram 100 and a reconstruction of a cross section of an object 110 obtained using the sinogram 100.

The quality (e.g. accuracy) of the reconstruction that is obtained for a given object is dependent on the ability to obtain and process—that is, perform tomographic reconstruction on—a sinogram that contains an adequate number of projections and range of data sampled across the detector. For example, in certain embodiments, accurate reconstruction depends on the ability to record data over a detector field of view that encompasses the full object that is being imaged.

In many practical cases, however, adequate sampling of an object is not possible. For example, the ability to obtain and store a full sinogram is limited due to software and/or computational limitations, such as memory limitations, data storage limitations, and the like. This is especially problematic for reconstruction of a large object, over a large field of view, and/or at high resolution.

Figure 17:
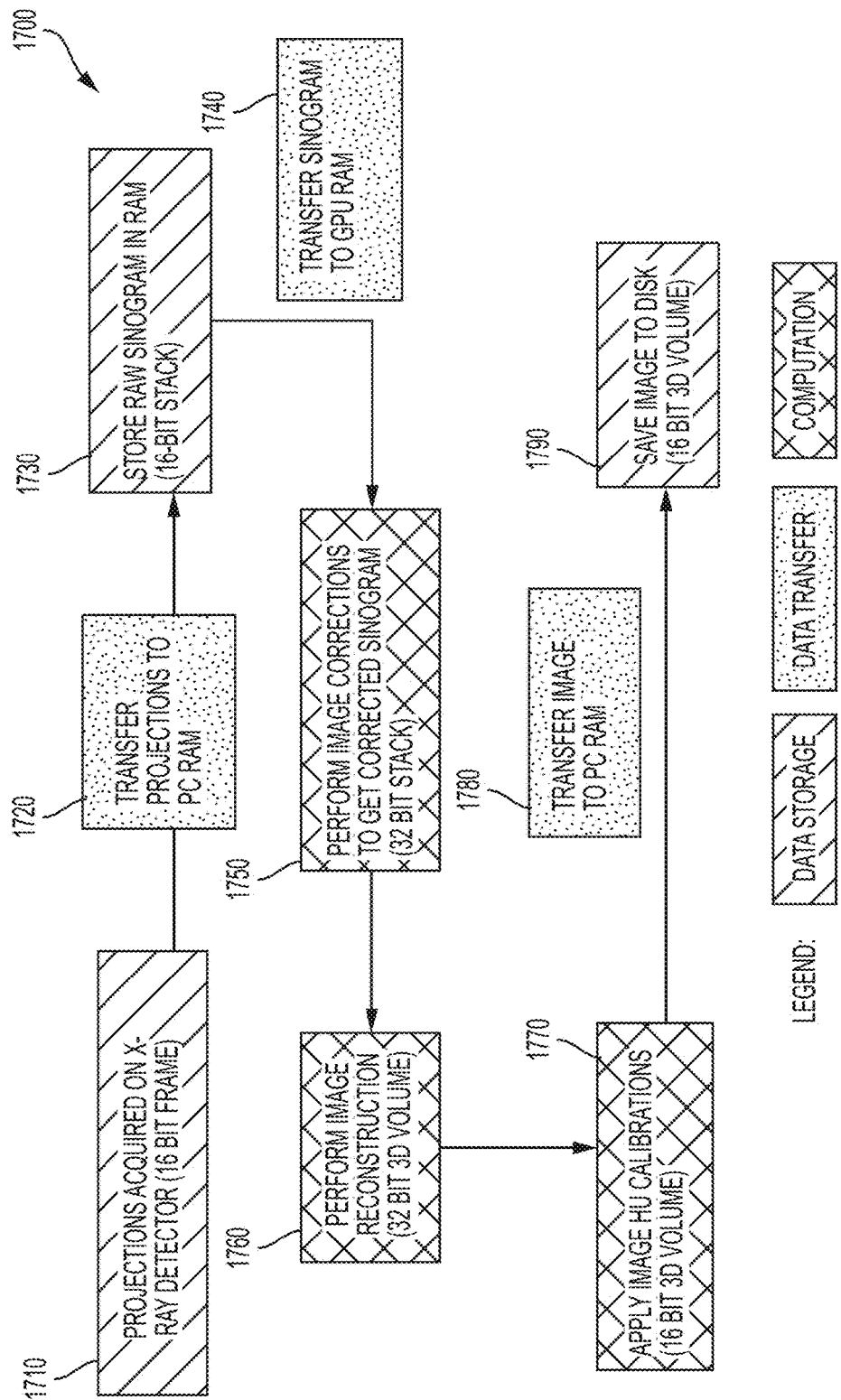
FIG. 17 is a block flow diagram of a process for acquiring a sinogram and performing reconstruction to obtain an image of a scanned object, according to an illustrative embodiment.

For example, turning, to FIG. 17, in certain embodiments, various steps used in obtaining an image of a subject by processing a sinogram including acquiring, accessing, and subsequent processing steps (e.g., by performing tomographic reconstruction) involve storage of sinogram data in memory of multiple different processing units, and transfer of sinogram data between different processing units. For example, FIG. 17 shows a block flow diagram of an example process 1700 for performing tomographic reconstruction using projections of a sinogram in order to obtain a 3D image of a subject with two different types of processing units—a central processing unit (CPU) of a PC and a graphics processing unit (GPU). In a first step 1710 in the process, projections are acquired with an X-ray detector via multi-angle scanning of a subject. As projections are acquired, they are transferred (1720) to random access memory (RAM) of a personal computer (PC) (e.g., RAM connected to a central processing unit (CPU) of a PC). Projections acquired via the multi-angle scan are stored in PC RAM to obtain a sinogram comprising the plurality of projections acquired for the angles of the multi-angle scan. In certain embodiments, subsequent processing of projections is performed by a GPU, and, in a next step 1740, the sinogram comprising the plurality of projections is transferred to GPU RAM.

In certain embodiments, raw data stored in acquired projections is represented using a first format that is converted to a different, second format prior to performing tomographic reconstruction. Accordingly, in certain embodiments, in a next step 1750 data conversion (e.g., raw data corrections) is applied to convert the data from the first format to the second format. For example, in certain embodiments, values stored in data elements of raw, initially acquired projections are represented in a 16-bit format and converted to a 32-bit format (e.g., 32-bit floating point) via the data conversion step 1750. In certain embodiments, the data conversion step 1750 is performed by GPU, following transfer of the sinogram to GPU RAM. In certain embodiments, the data conversion step 1750 is performed by the PC (e.g., by a PC CPU), prior to transfer of the sinogram to the GPU.

In certain embodiments, tomographic reconstruction is performed (1760) using the converted sinogram (e.g., 32-bit format) to obtain a 3D image of the subject. In certain embodiments, the 3D image obtained via tomographic reconstruction is represented in the second format (e.g., as 32-bit data, e.g., as 32-bit floating point data). In certain embodiments, values (e.g., intensities) of the obtained 3D image represent values of a linear attenuation coefficient of the subject being image (e.g., spatial variation in intensity of the 3D image represents spatial variation in linear attenuation coefficient through the subject). In certain embodiments, in a next step 1770 values of the 3D image are converted to Hounsfield Units. In certain embodiments, the 3D image is also converted from the second data format to the first data format. In certain embodiments, in a next step 1780, the 3D image is transferred from the GPU (e.g., from GPU RAM) to the PC RAM and stored (e.g., stored in disk memory)

In certain embodiments, the size of a sinogram in terms of the amount of memory it occupies (e.g., in megabytes, e.g., in gigabytes) depends on a variety of factors, such as a number of pixels of a detector used to acquire projections of the sinogram and the data format used to represent values of the sinogram.

Figure 18B:
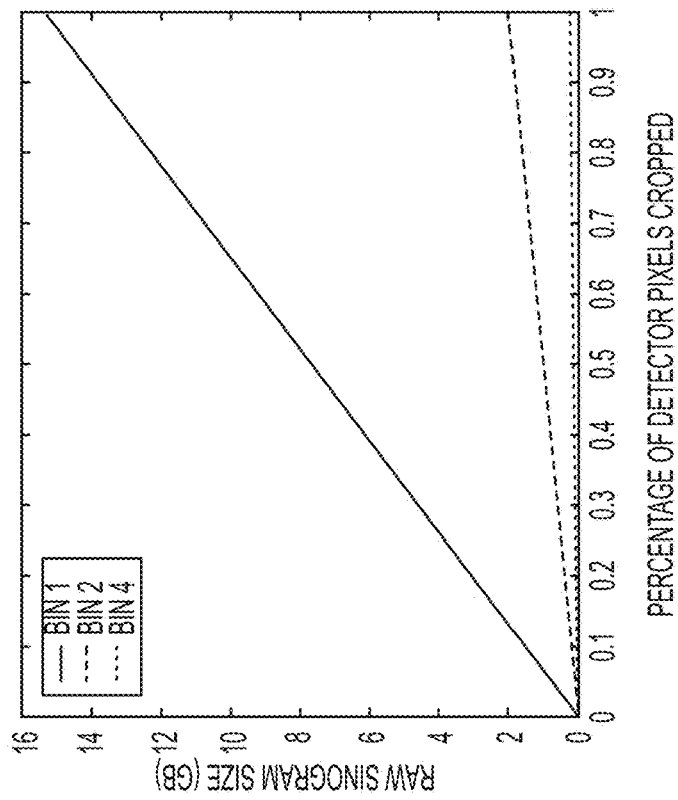
FIG. 18B is a graph showing the size, in GB, of a 32-bit sinogram as a function of percentage of detector pixels cropped and resolution for a 2.65 MP detector, according to an illustrative embodiment.
Figure 18A:
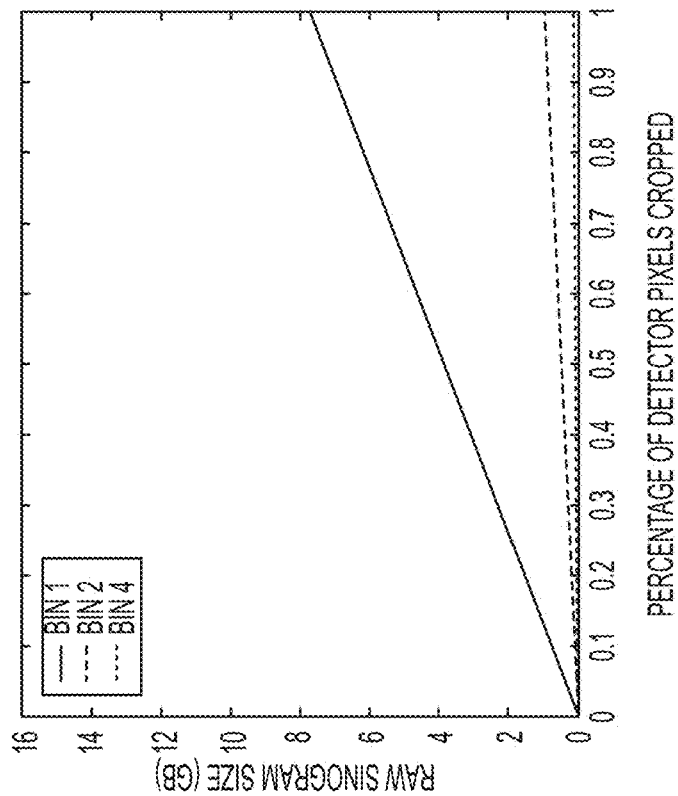
FIG. 18A is a graph showing the size, in gigabytes (GB), of a 16-bit sinogram as a function of percentage of detector pixels cropped and resolution for a 2.65 megapixel (MP) detector, according to an illustrative embodiment.
Figure 19A:
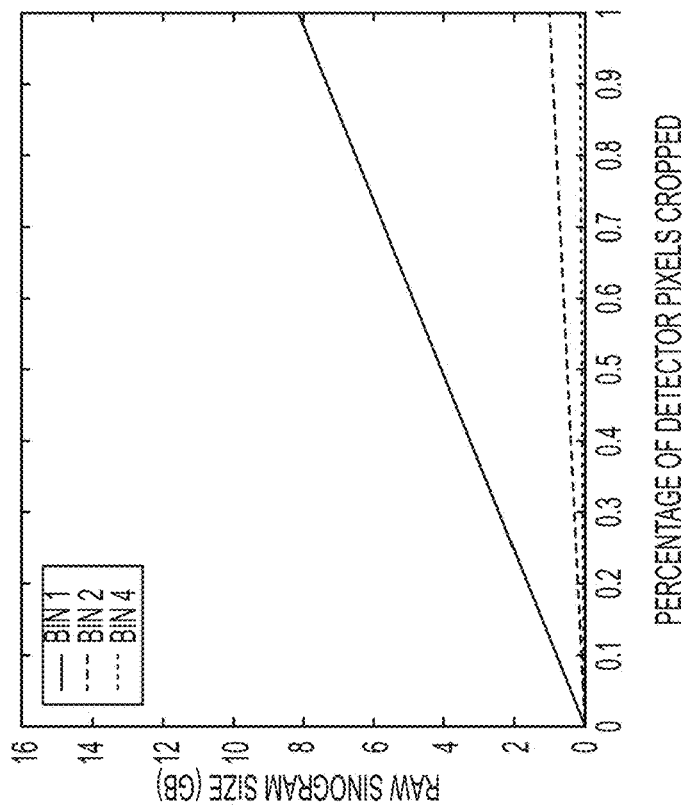
FIG. 19A is a graph showing the size, in GB, of a 16-bit sinogram as a function of percentage of detector pixels cropped and resolution for a region of a detector comprising 1.4 MP, according to an illustrative embodiment.
Figure 19B:
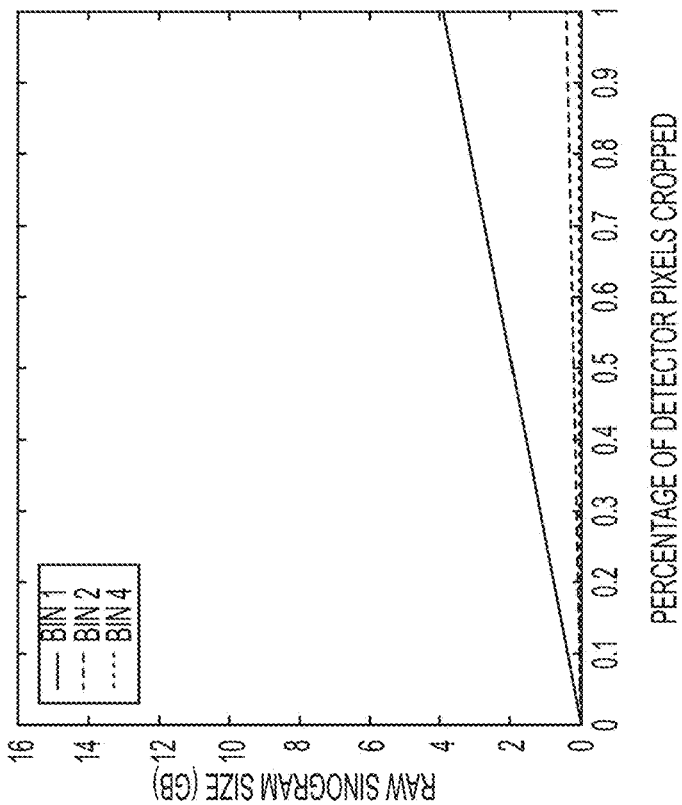
FIG. 19B is a graph showing the size, in GB, of a 32-bit sinogram as a function of percentage of detector pixels cropped and resolution for a region of a detector comprising 1.4 MP, according to an illustrative embodiment.

For example, FIG. 18A and FIG. 18B are graphs showing the size of sinograms storing values representing signals from pixels of a 2.65 megapixel detector. The graphs show sinogram sizes for three different resolutions—bin 1, bin 2, and bin 4. The graphs plot variation in sinogram size depending on a percentage of detector pixels cropped (e.g., percentage of detector pixels for which values are stored in the sinogram), as indicated by the x-axis. FIG. 18A plots sinogram size for the three different resolutions for sinograms storing 16-bit data, and FIG. 18B plots sinogram size for the three different resolutions for sinograms storing 32-bit data. Each projection of a sinogram having bin 1 resolution stores a value for each pixel of the detector, and, accordingly, occupies a large amount of memory. In certain embodiments, reducing the number of detector pixels for which values are stored in projections of the sinogram reduces the size of the sinogram, as shown in FIG. 18A and FIG. 18B by decrease in sinogram size with decreasing percentage of detector pixels cropped. In certain embodiments, reducing resolution of the sinogram also reduces sinogram size. For example, a sinogram having bin 2 resolution stores a single value for every four detector pixels (e.g., a single value represents signal from a two-by-two array of detector pixels). For example, a sinogram having bin 4 resolution stores a single value for every sixteen detector pixels (e.g., a single value represents signal from a four-by-four array of detector pixels). Accordingly, as shown in FIG. 18A and FIG. 18B, bin 2 and bin 4 sinograms have reduced sizes in comparison with a bin 1 sinogram. In another example, FIG. 19A and FIG. 19B are graphs plotting similar data to the results shown in FIG. 18A and FIG. 18B, but for half-panel sinograms that comprise data from a region of a detector comprising 1.4 MP.

The ability to record a full sinogram in practice may also be limited by physical considerations. For example, an object may simply be too large to fit into the physical beam—that is, the size (e.g. extent) of the physical beam that illuminates the object does not span the entire extent of the object, such that portions of the object are not sampled. Another physical consideration relates to the desire to limit the radiation exposure of the subject. In this case, only a particular area of interest is exposed.

Situations where a full sinogram is not obtained (e.g., due to memory management issues or physical considerations) ultimately result in an incomplete, or truncated sinogram being recorded and used for obtaining a reconstruction of an object. The quality of the reconstructions obtained by performing tomographic reconstructions on such truncated sinograms is reduced. In particular, relative to an ideal reconstruction obtained from a full sinogram, relative contrast values within a reconstruction obtained from a truncated sinogram may vary. Reconstructions obtained from truncated sinograms may also include artifacts.

Figure 2:
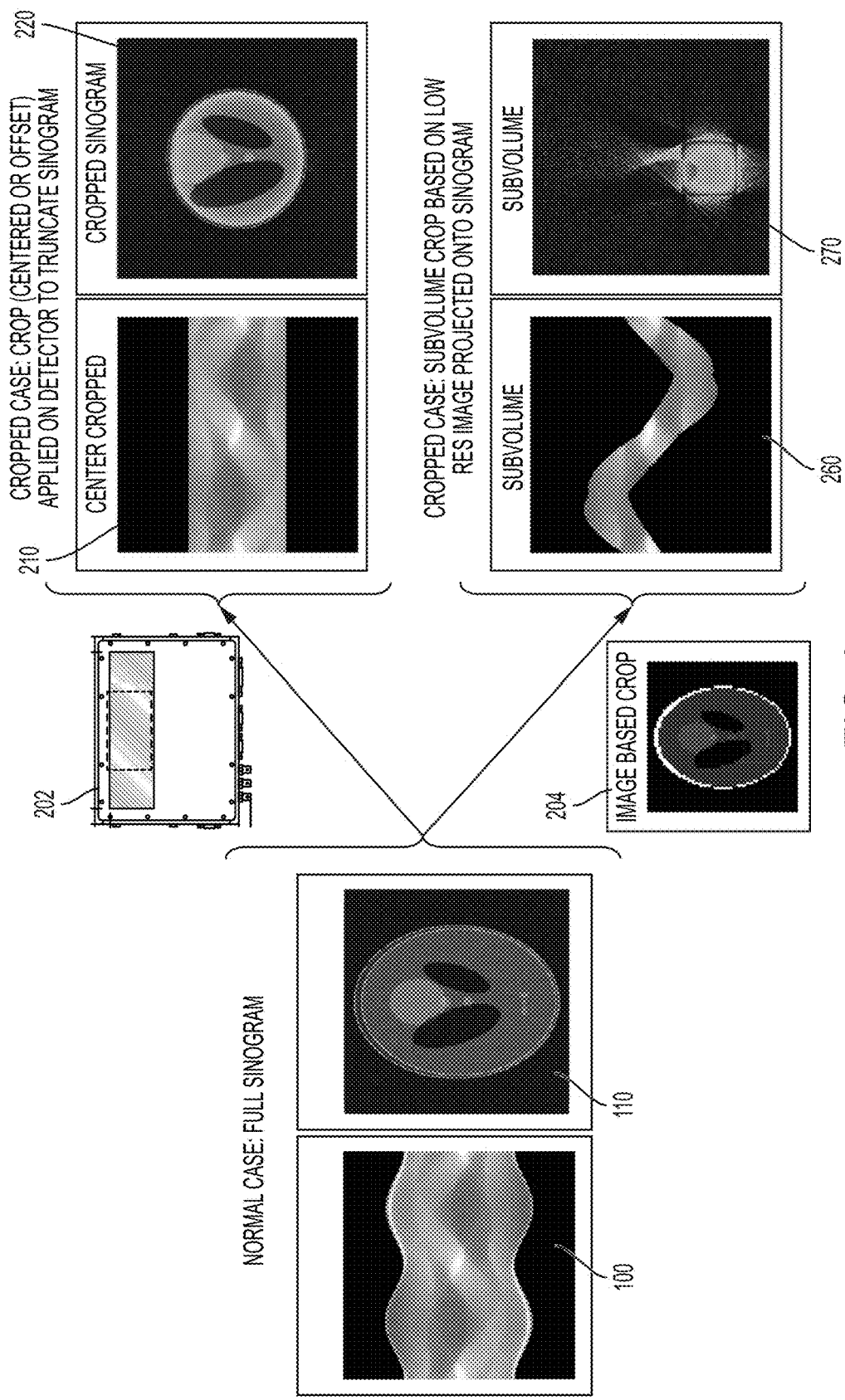
FIG. 2 is a depiction illustrating reasons for sinogram truncation.

Sinogram truncation and its effects are illustrated in FIG. 2. An ideal, full sinogram 100 is shown, along with the resulting tomographic reconstruction 110 obtained from the full sinogram. FIG. 2 also shows two different examples of truncated sinograms.

In the example of FIG. 2, the full sinogram is a sinogram for which the entire object is within the field of view of the detector, and each projection of the full sinogram stores data over the full detector area. Accordingly, each projection of the full sinogram stores data that represents signals acquired across a region of the detector whose field of view encompasses the entire object.

A first example shows a sinogram 210 that is truncated due to detector crop. Due to detector crop, for each projection (e.g., at each angle), data is recorded for only a portion of the detector area. Accordingly, the extent of the recorded sinogram 210 is truncated along the dimension(s) corresponding to the detector coordinates. The grayscale values in the reconstruction 220 obtained from the truncated sinogram 210 differ from the contrast in the reconstruction 110 obtained via the ideal, full sinogram. The difference is most noticeable around the edges of the representation of the object. In certain embodiments, the portion of the detector area to which the truncated sinogram corresponds has a field of view that corresponds (e.g., maps to) a particular region of interest (ROI) within the subject. In certain embodiments, data is stored for only a particular region of the detector based on a specific ROI to which it corresponds (e.g., the region of the detector is defined by projecting the ROI onto the detector area). In certain embodiments, artifacts such as those shown in the reconstruction 110 become more severe as the ROI and, accordingly, the region of the detector to which the truncated projections correspond shrinks.

A second example shows a sinogram 260 that is truncated due to a subvolume crop. In the subvolume crop, projections are recorded only for a subvolume of the object, which corresponds to a specific region of interest (ROI) 250 within the object. In the subvolume cropped sinogram 260, the range of values along the projection direction for which data is recorded varies with the angular parameter. Comparing the reconstruction 270 obtained via the subvolume cropped sinogram 260 with the reconstruction 110 obtained via the idealized, full sinogram 100, the subvolume cropped reconstruction 270 shows a significant shift in intensity values, along with artifacts at the edges and outside of the region of interest.

Described herein are approaches that allow accurate reconstruction to be obtained, even when an ideal, full sinogram is not recorded and used to obtain the reconstruction. In certain embodiments, the approaches described herein address memory management challenges by reducing the size of sinograms and/or projections that need to be stored in memory, while still allowing for accurate reconstructions to be obtained using smaller size sinograms that, for example, have a low resolution or do not include data corresponding to a full area of the detector.

Figure 3:
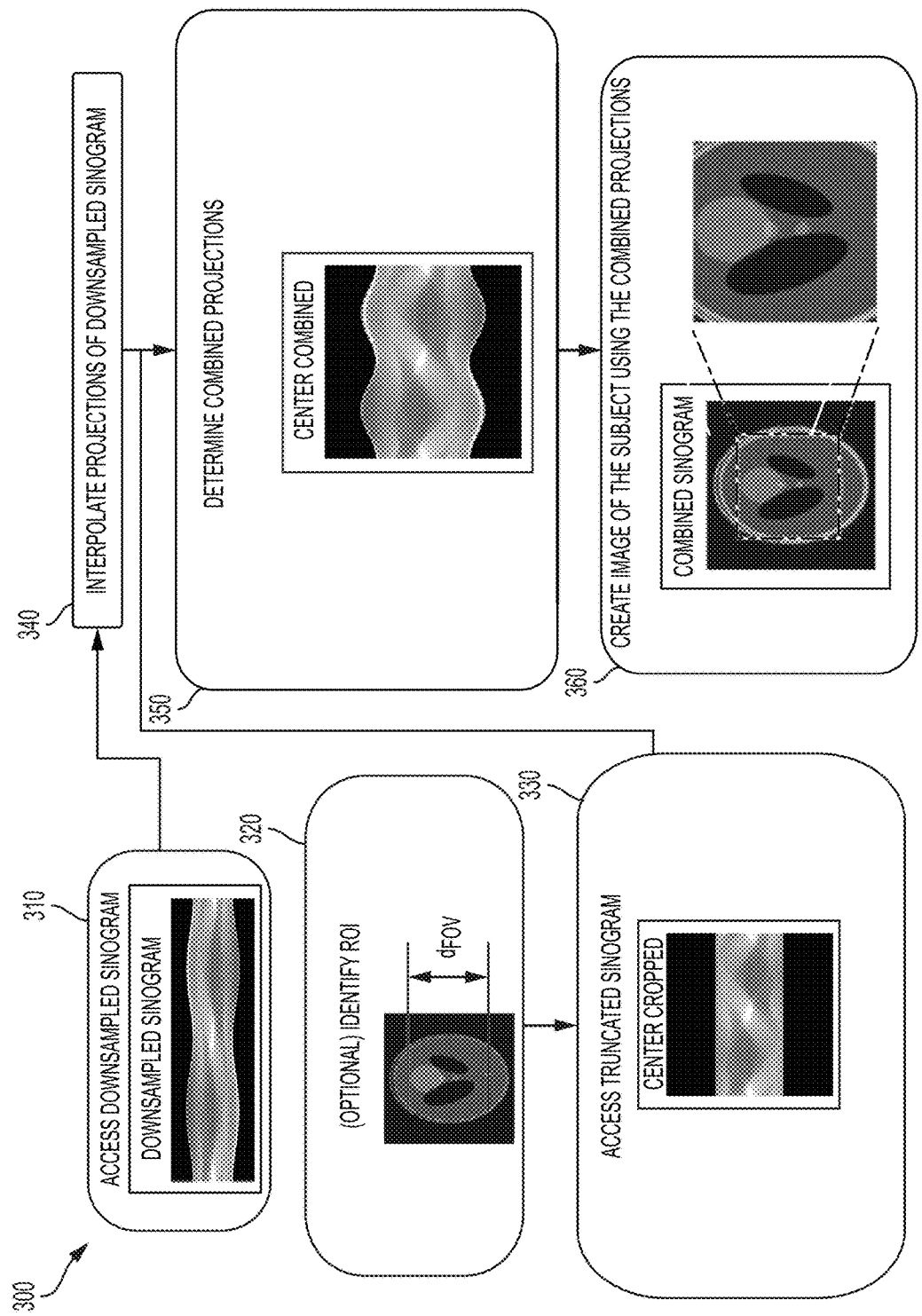
FIG. 3 is a flow diagram depicting a "data combination" method for automated sinogram completion according to an illustrative embodiment, where the sinogram to be completed is truncated due to a detector crop.

Completion of Truncated Sinograms Due to Detector Crop
Completion by Sinogram Combination FIG. 3 shows a block flow diagram of an example process 300 for automated completion of a sinogram that is truncated due to detector crop using a sinogram combination approach. In a first step 310, a downsampled sinogram is accessed. Projections of the downsampled sinogram store data acquired across large, first region of the detector, but at a relatively low, first resolution. For example, in certain embodiments, the first region of the detector is the full detector area (e.g., acquired using the entire are of the detector). Projections that store data recorded using the full detector area are referred to herein as "full panel" projections. In certain embodiments, the first region of the detector has a field of view that encompasses the entire object to be imaged. In certain embodiments, the first resolution is below the bin 1 resolution—that is, each data element of each projection of the downsampled sinogram corresponds to multiple detector pixels. For example, in certain embodiments, the downsampled sinogram comprises a plurality of bin 4 projections (e.g., a bin 4 downsampled sinogram, $S_{4 \times 4}$, is accessed).

In a another step 330, a truncated sinogram is accessed. Projections of the truncated sinogram store data acquired across a second region of the detector that is typically smaller than the first region of the detector. Projections of the truncated sinogram, however, have a relatively high resolution. In particular, in certain embodiments, the resolution of the projections of the truncated sinogram is higher than the resolution of the projections of the downsampled sinogram (e.g., the second resolution is higher than the first resolution). For example, a plurality of truncated bin 1 projection may be acquired in order to obtain a truncated sinogram, $S_{1 \times 1, trunc}$, that is accessed in step 330.

In certain embodiments, the second region of the detector is a sub-region of the first region. Accordingly, the truncated sinogram (e.g., $S_{1 \times 1, trunc}$) is a detector cropped sinogram and, accordingly, does not include data from locations of the detector outside the second region.

In certain embodiments, a field of view of the second region of the detector corresponds to a region of interest (ROI) of the object, as indicated, for example, by $d_{FOV}$ in FIG. 3. In certain embodiments, the ROI is identified in an optional step 320. The ROI may be identified using a photograph of the object, such as an optical image, a fluorescence image, a bioluminescence image, or any other light-based image. The ROI may be identified using a low resolution CT image reconstructed using the downsampled sinogram (e.g., $S_{4 \times 4}$).

In certain embodiments, the ROI is pre-defined in the CT configuration, and identification of the ROI in an additional step (e.g., optional step 320) is not necessary.

In certain embodiments, the process provides for data that is missing from the projections of the truncated sinogram (e.g., $S_{1 \times 1, trunc}$) to be filled in, thereby completing the sinogram. The missing data in the truncated sinogram corresponds to the data for portions of the X-ray detector area that are outside the second region of the detector (e.g., and, accordingly, correspond to regions of the object that are outside the ROI). In particular, in another step 340, each projection of the downsampled sinogram (e.g., $S_{4 \times 4}$) is interpolated based on the resolution of the truncated sinogram [e.g., the second resolution (e.g., bin 1)] to obtain a plurality of interpolated projections (e.g., projections of an interpolated sinogram; e.g., projections of $S_{4 \times 4\_to\_1 \times 1}$). In particular, interpolation of the projections of the downsampled sinogram matches the resolution of the downsampled sinogram to the resolution of the truncated sinogram. In this manner, rather than directly obtaining and storing a large number of values corresponding to a high density of locations across the full detector area (e.g., every detector pixel), values of detector pixels outside the second region are approximated by interpolating the low resolution data of the downsampled projections.

In another step 350, a plurality of combined projections are determined using projections of the truncated sinogram and the interpolated sinogram. The combined projections use data from the truncated projections to represent signal detected from the second region and data from the interpolated projections to represent signal detected from locations of the detector that within the first region, but outside the second region.

For example, in certain embodiments, a combined projection associated with a given angle of a multi-angle scan is determined by combining data from a corresponding interpolated projection (e.g., associated with a same angle) and with data from a corresponding (e.g., associated with a same angle) projection of the truncated sinogram. In particular, values of the corresponding projection of the truncated sinogram that represent signals from the second region are stored in corresponding data elements of the combined sinogram, while values of the corresponding interpolated projection that correspond to signals from the first region are stored in corresponding data elements of the combined sinogram.

In certain embodiments, a combined projection can be determined by replacing empty data elements of a corresponding truncated projection with values from a corresponding interpolated projection (e.g., by replacing empty columns of $S_{1 \times 1, trunc}$ with the interpolated data from $S_{4 \times 4\_to\_1 \times 1}$), and storing the result as a combined projection. In certain embodiments, determining the plurality of combined projections allows one to obtain a combined sinogram, $S_{combined}$.

In certain embodiments, a data weighting approach is used to determine combined projections. In particular, in certain embodiments, data elements of combined projections are determined a weighted sum of data elements of corresponding truncated and interpolated projections. For example, in certain embodiments a given data element, of a combined projection may be determined via a function. such as CombinedProjection(p)=[(1−w(p))*InterpolatedProjection(p)+w(p)*TruncatedProjection(p)]−InterpolatedProjection(p), where p is a variable representing a position on the detector (e.g., a variable along detector rows), and w(p) is a weighting function that varies with position on the detector (e.g., along detector rows. In certain embodiments, the weighting function varies between 0 and 1. In certain embodiments the weighting function has a low value (e.g., 0) near detector crop marks, and gradually increases to a higher value (e.g., 1) away from the detector crop marks.

In certain embodiments, in a next step 360, once the combined projections are determined, they are used to obtain a 3D image of the subject. For example, in certain embodiments, tomographic reconstruction is performed using the combined projections to obtain a 3D image of the subject.

In certain embodiments, depending on the computational cost of storing in memory (e.g., RAM) and processing a given amount of sinogram data and the size of an ideal full sinogram, the process 300 allows 3D image of a subject to be obtained at a reduced computational cost. In particular, in certain embodiments, the two sinograms that are processed—the downsampled sinogram and the truncated sinogram—occupy less space in memory than a single full sinogram (e.g., a high resolution sinogram having a resolution of the truncated sinogram, but comprising data corresponding to the full detector area). Moreover, in certain embodiments, the interpolation, data combination, and tomographic reconstruction steps (steps 340, 650, and 360) are performed in a step-wise fashion, operating on each projection individually, such that it is not necessary to store a full set of interpolated projections (e.g., an interpolated sinogram comprising, for each angle of a multi-angle scan, an interpolated projection) and/or a full set of combined projections (e.g., a combined sinogram comprising, for each angle of a multi-angle scan, a combined projection) in memory all at once.

For example, in certain embodiments, the image of the subject is obtained via a tomographic reconstruction approach (e.g., filtered back-projection) where each projection is processed individually such that it is not necessary to store more than a single combined projection in memory at a given time.

For example, in certain embodiments, the tomographic reconstruction algorithm begins by initializing values (e.g., setting each value to a numeric 0) of a stored dataset (e.g., a 3D dataset) that, once processing is complete, will represent the image of the object. The tomographic reconstruction algorithm operates on each projection of the sinogram via a sub-step that back-projects the projection and updates values of the stored dataset by combining the result of the back-projection operation with the stored dataset. In certain embodiments, the sub-step first applies one or more filters (e.g., a high-pass filter; e.g., a ramp filter) and then back-projects the filtered projection. This sub-step is repeated for each projection and, once all projections have been processed, the stored dataset is the 3D image of the subject. For example, in a filtered back-projection algorithm, the result of the back-projection operation is added to (summed with) the values of the stored dataset, such that the stored dataset represents a running sum over the back-projections of all projections processed up to a given point in time.

Figure 16:
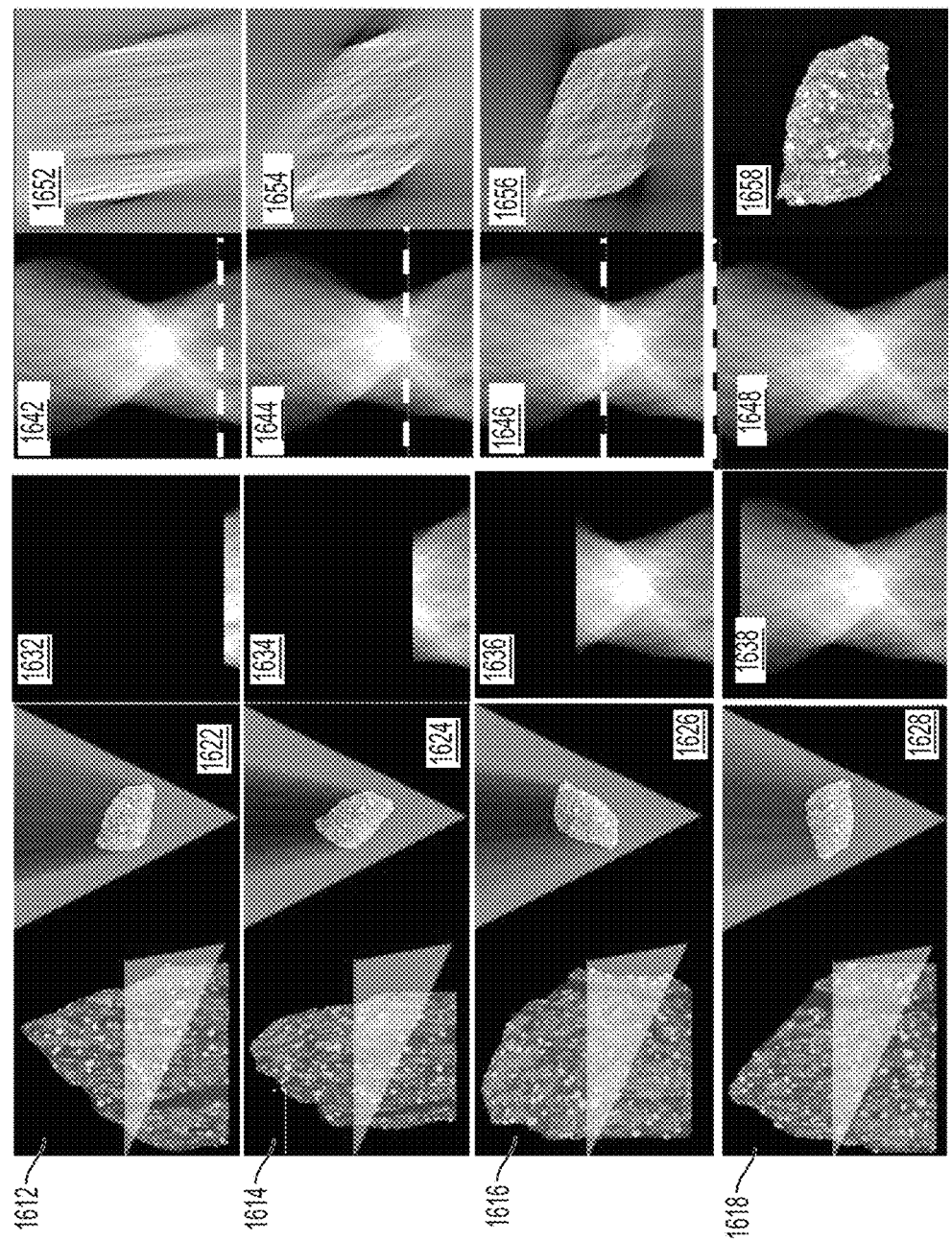
FIG. 16 is a schematic comprising a plurality of images illustrating the steps in acquiring a sinogram via a multi-angle scan of an object and performing tomographic reconstruction to obtain an image of the object, according to an illustrative embodiment.

For example, turning to FIG. 16, representations of the state (e.g., after a given number of projections have been processed via the reconstruction sub-step) of the stored dataset (1652, 1654, 1656, and 1658) as it is updated are shown. The example of FIG. 16 illustrates how the stored dataset is updated as each projection is processed until the image of the object is obtained. The particular projections having been processed at a given state of the stored dataset are indicated in the representations (1642, 1644, 1646, and 1648) of a sinogram. In particular, each projection along the vertical dimension of the sinogram (which corresponds to the angular parameter) up to the white dashed line have been stepped through and processed via repeated application of the reconstruction sub-step. For example, the dataset shown in representation 1652 is obtained by processing a small portion of projections of the sinogram, as shown in 1642. Increasing number of projections are processed to obtain the datasets shown in images 1654 and 1656 (e.g., as indicated by representation 1644, which corresponds to image 1654, and representation 1646, which corresponds to image 1656). Finally, image 1658 is obtained by processing nearly all projections (e.g., as shown in 1648), and provides an accurate representation of the object scanned.

Accordingly, in certain embodiments, it is not necessary for the tomographic reconstruction process to store in memory, and operate on every projection of a sinogram at once. In certain embodiments, it is thus not necessary to store every projection of a complete interpolated sinogram and every projection of a complete combined sinogram in memory. Instead, for a given angle (e.g., value of the angular parameter), a corresponding interpolated projection can be obtained by interpolating a projection of the downsampled sinogram that is associated with that angle. A corresponding combined projection is then determined using the interpolated projection and a projection of the truncated sinogram that is also associated with the given angle. The reconstruction sub-step is then performed on the combined projection (e.g., the combined projection is back-projected and summed with the stored dataset). The steps of, for a given angle, obtaining a corresponding interpolated and a corresponding combined projection, and performing the reconstruction sub-step on the corresponding combined projection are repeated for each of a plurality of angles in order to obtain an image of the object. This approach avoids a need to store a large number of high resolution, large area combined projections in memory at the same time.

In certain embodiments, sinogram completion approaches described herein, such as the approach described above with reference to FIG. 3, are performed by a processor of a computing device. As used herein, the term "processor", refers to one or more devices of one or more different types. In particular, steps and functions described herein as performed by "a processor" may be performed by any number of processing devices. In certain embodiments, certain steps and functions may be performed by a single processor of a single computing device. In certain embodiments, a step or function, such as obtaining a 3D image using a combined sinogram (e.g., via tomographic reconstruction) is partitioned between and performed by multiple processors. The multiple processors may be of a single computing device, for example a multi-core device, and/or of different computing devices, such as in a distributed computing system (e.g., a cluster). The term processor, as used herein, also encompasses different types of processing units, such as central processing units (CPUs) and graphics processing unites (GPUs). In certain embodiments, a portion of steps (including none of the steps and up to all of the steps) in the approaches described herein may be performed by a first type of processing unit (e.g., a CPU) and a remaining portion of steps (including none of the steps and up to all of the steps) performed by a second type of processing unit (e.g., a GPU).

In certain embodiments, any of the sinogram completion approaches described herein (e.g., with reference to any one of FIG. 3, FIG. 4, FIG. 6, FIG. 7, FIG. 9, FIG. 10, and FIG. 12) may be performed as part of the process 1700 described above with reference to FIG. 17. [For example, in certain embodiments, various steps (e.g., steps of interpolating projections of a downsampled sinogram and determining combined projections) are performed using a first type of processing unit (e.g., a CPU), and various steps (e.g., performing tomographic reconstruction using the combined projections) are performed by a second type of processing unit.

Figure 20:
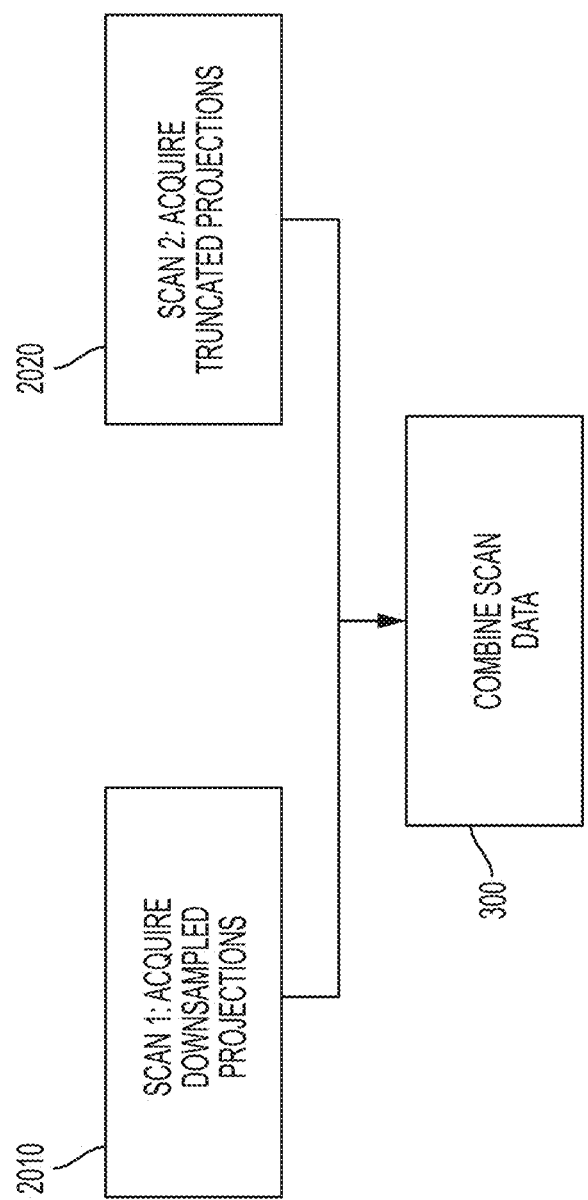
FIG. 20 is a block flow diagram of a process for acquiring and combining a downsampled sinogram and a truncated sinogram, according to an illustrative embodiment.

Turning to FIG. 20, in certain embodiments, the downsampled and truncated sinograms used in the data combination approach described above with respect to FIG. 3 are acquired using two separate multi-angle scans of a subject. FIG. 20 is a block flow diagram showing an example of a process 2000 for acquiring and combining a downsampled sinogram and a truncated sinogram using two separate scans. In certain embodiments, in one step 2010, low resolution, large area (e.g., full panel bin 4 projections) are acquired via a first multi-angle scan of the subject and stored to obtain a downsampled sinogram. In another step, high resolution projections are acquired and only values for data elements corresponding to a smaller sub-region of the detector (e.g., a region of the detector having a field of view corresponding to a ROI) are stored to obtain a truncated projection. The downsampled sinogram and the truncated sinogram acquired in this manner may then be processed via the approach described above with respect to FIG. 3 (e.g., process 300) to obtain a 3D image of the subject.

Figure 21:
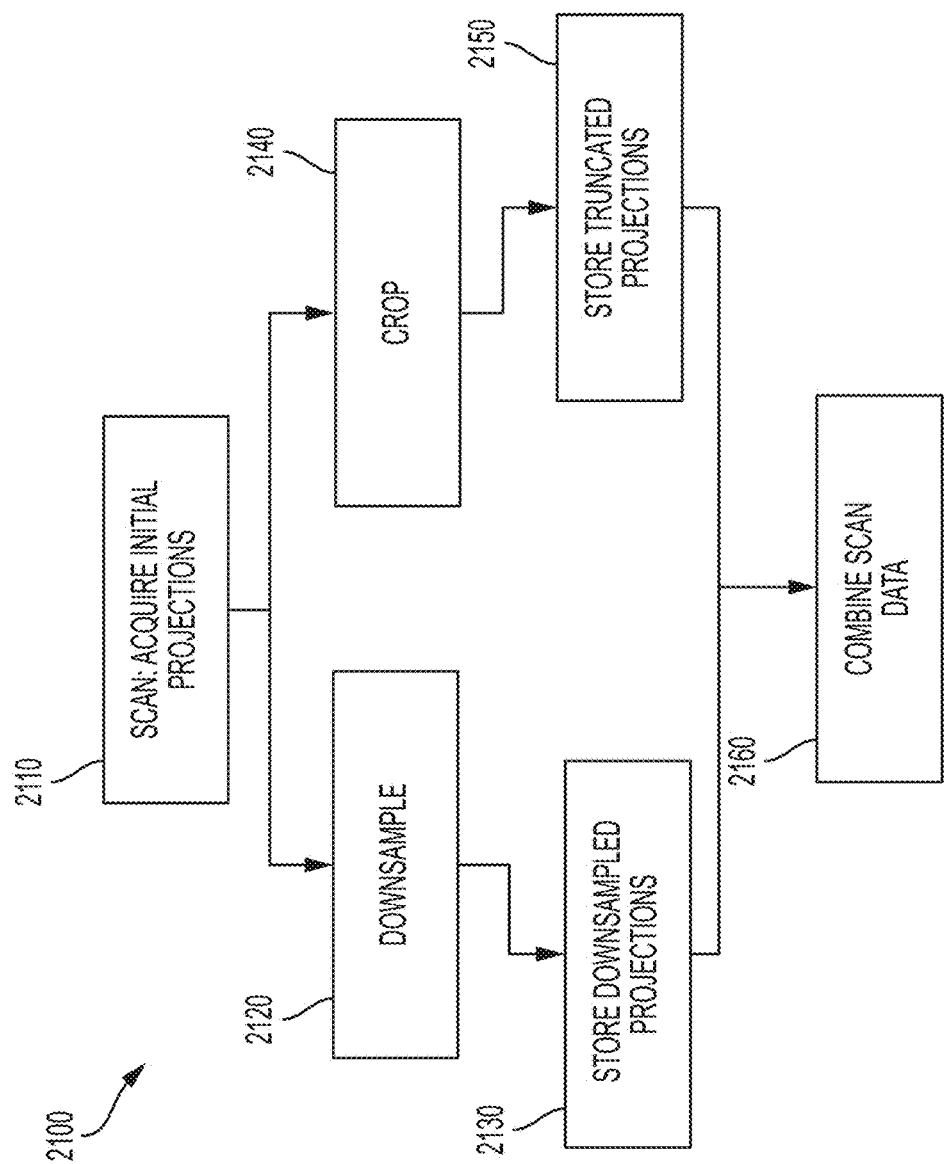
FIG. 21 is a block flow diagram of a process for acquiring and combining a downsampled sinogram and a truncated sinogram, according to an illustrative embodiment.

Turning to FIG. 21, in certain embodiments, the downsampled and truncated sinograms used in the data combination approach described above with respect to FIG. 3 are acquired using a single scan of a subject. FIG. 21 is a block flow diagram showing an example process 2100 for acquiring and combining a downsampled sinogram and a truncated sinogram using a single multi-angle scan of a subject. In certain embodiments, in one step 2110 initial projections are acquired via multi-angle scanning of the subject. The initial projections store data representing signals from a first, large region (e.g., the full detector area) of a detector used to record the projections at a high resolution (e.g., bin 1). In certain embodiments, as the initial projections are acquired, they are downsampled and cropped to obtain downsampled and truncated projections. In particular, in another step 2120, each initial projection is downsampled to a reduced resolution, thereby obtaining a downsampled projection. Each downsampled projection is then stored (2140) as a projection of the downsampled sinogram. In another step, each initial projection is cropped to obtain a truncated projection that stores data from a smaller, sub-region of the first region. In certain embodiments, a truncated projection is obtained by removing data elements that correspond to locations of the detector that are outside of the sub-region. Once obtained, truncated projections are stored (2150) as projections of the truncated sinogram. The downsampled sinogram and the truncated sinogram acquired in this manner may then be processed via the approach described above with respect to FIG. 3 (e.g., process 300) to obtain a 3D image of the subject.

Completion by Padding

Figure 4:
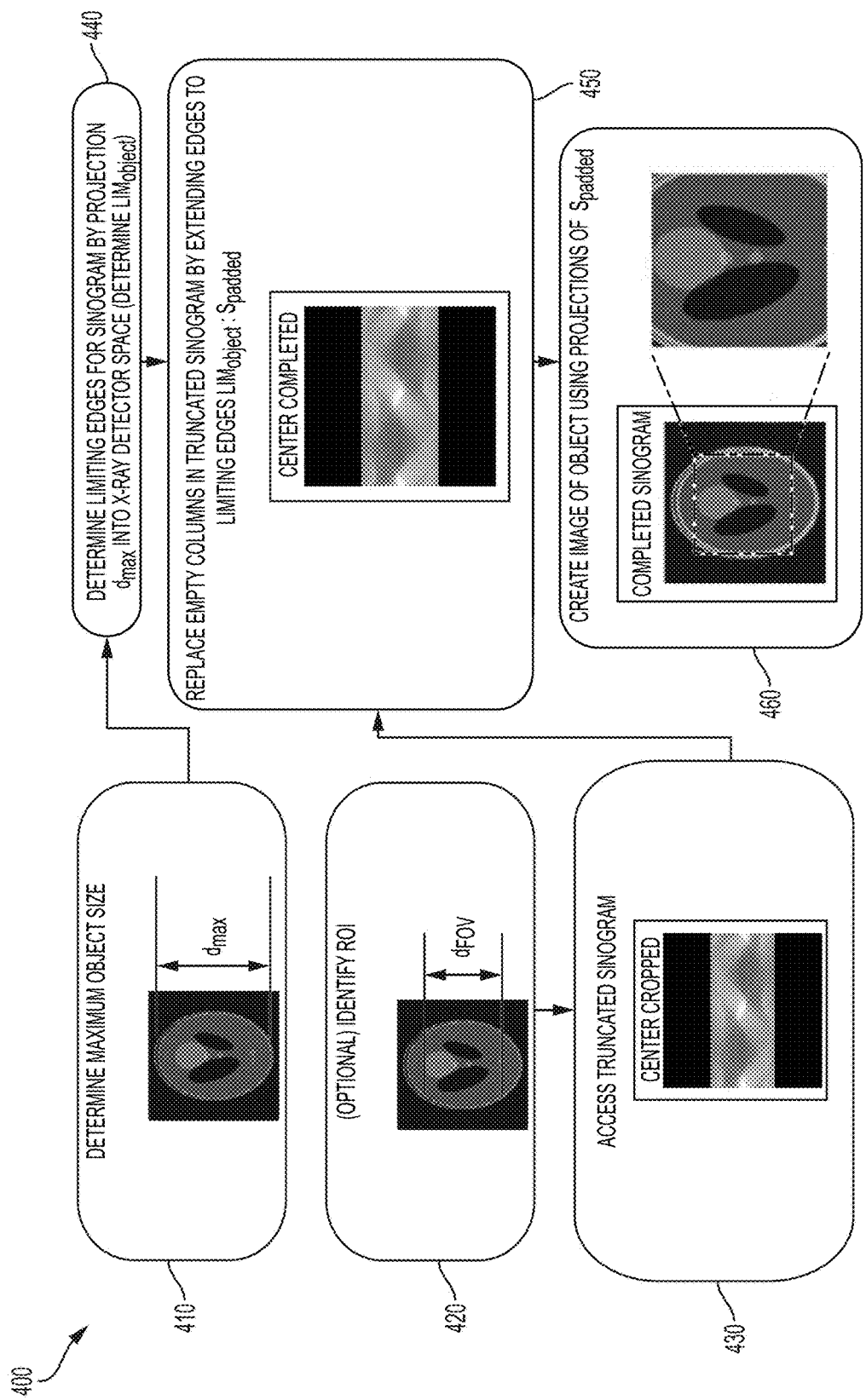
FIG. 4 is a flow diagram depicting a "data completion" method for automated sinogram completion according to an illustrative embodiment, where the sinogram to be completed is truncated due to a detector crop.

FIG. 4 is a block flow diagram of a process 400 for automated completion of a sinogram via a padding approach. In a first step, a first region of interest is identified on a photograph of the object to determine a maximum object size, $d_{max}$.

In a another step 430, truncated projections (e.g., truncated bin 1 projections) are acquired using a second region of interest corresponding to the CT field of view, $d_{FOV}$, in order to obtain a truncated sinogram, $S_{1\times1,trunc}$. The truncated sinogram $S_{1\times1,trunc}$ is a detector cropped sinogram and, accordingly, does not include data representing signals detected by regions of the detector (e.g., detector pixels) that are outside the second region of interest.

In certain embodiments, the second region of interest corresponding to the CT field of view is identified in an optional step 420. The second region of interest may be identified using a photograph of the object, such as an optical image, a fluorescence image, a bioluminescence image, or any other light-based image.

In certain embodiments, the second region of interest is pre-defined in the CT configuration, and identification of the region of interest is not necessary.

In certain embodiments, the process 400 provides for missing data in the truncated sinogram, $S_{1\times1,trunc}$, to be filled in, thereby completing the sinogram. The missing data in the truncated sinogram corresponds to the data for regions of the detector (e.g., detector pixels) that are outside the second region of interest. The process 400 fills in the missing data via a data padding approach. In particular, in another step 440, the limiting columns, $LIM_{object}$ are determined by projecting $d_{max}$ into the X-ray detector space. In another step 450, empty columns in $S_{1\times1,trunc}$ are replaced by extending the edges of $S_{1\times1,trunc}$ to the limiting edges, $LIM_{object}$ (e.g., via extrapolation), in order to obtain a completed sinogram, $S_{padded}$.

In certain embodiments, once the completed sinogram, $S_{padded}$ is obtained, projections of $S_{padded}$ are used to obtain a reconstruction of the object (460).

Comparison of Completion by Combination and Completion by Padding Approaches

Figure 5A:
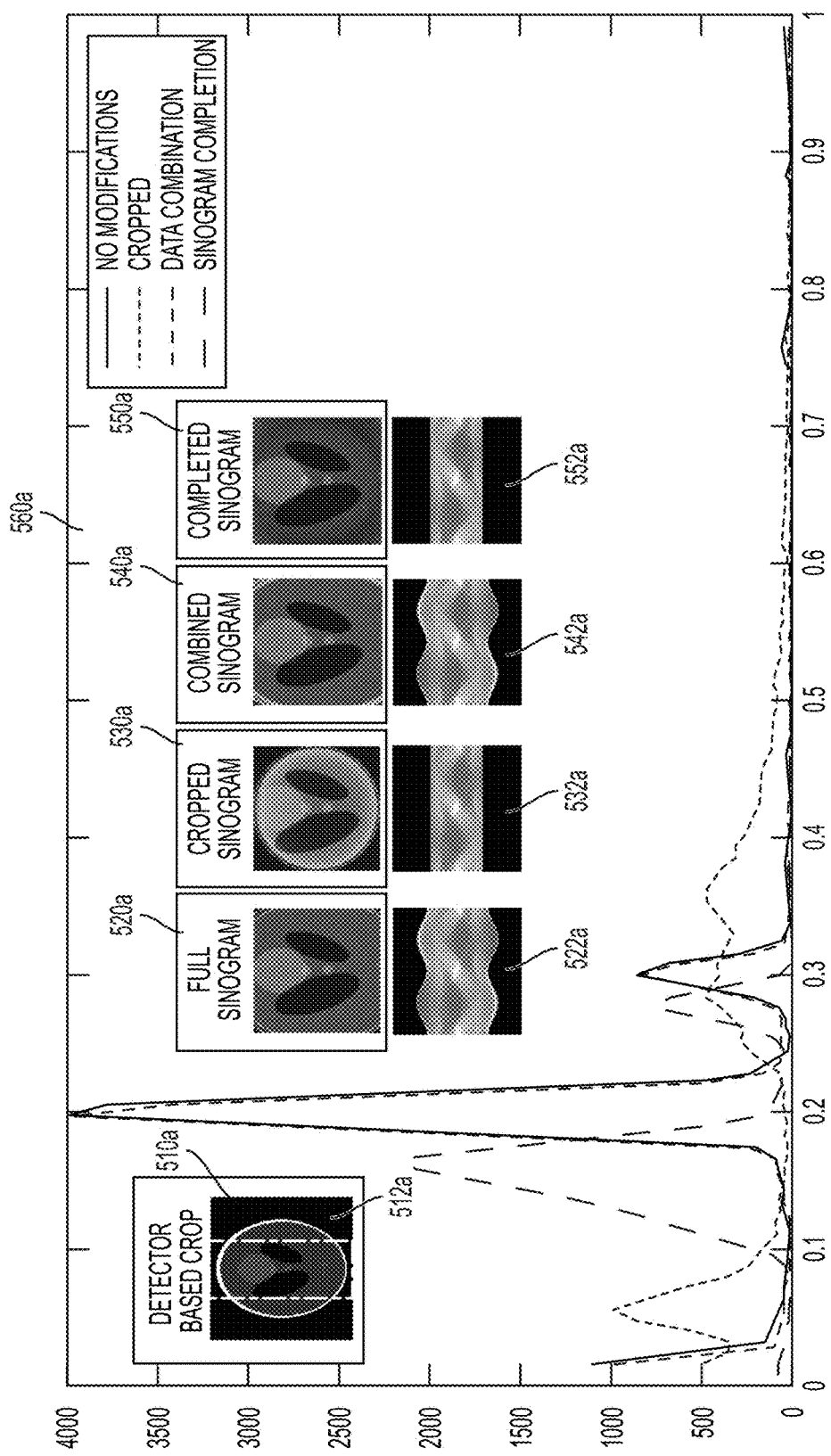
FIG. 5A depicts region of interest (ROI) histograms from results obtained using the data combination and data completion methods of FIGS. 3 and 4 for a center-based crop.
Figure 5B:
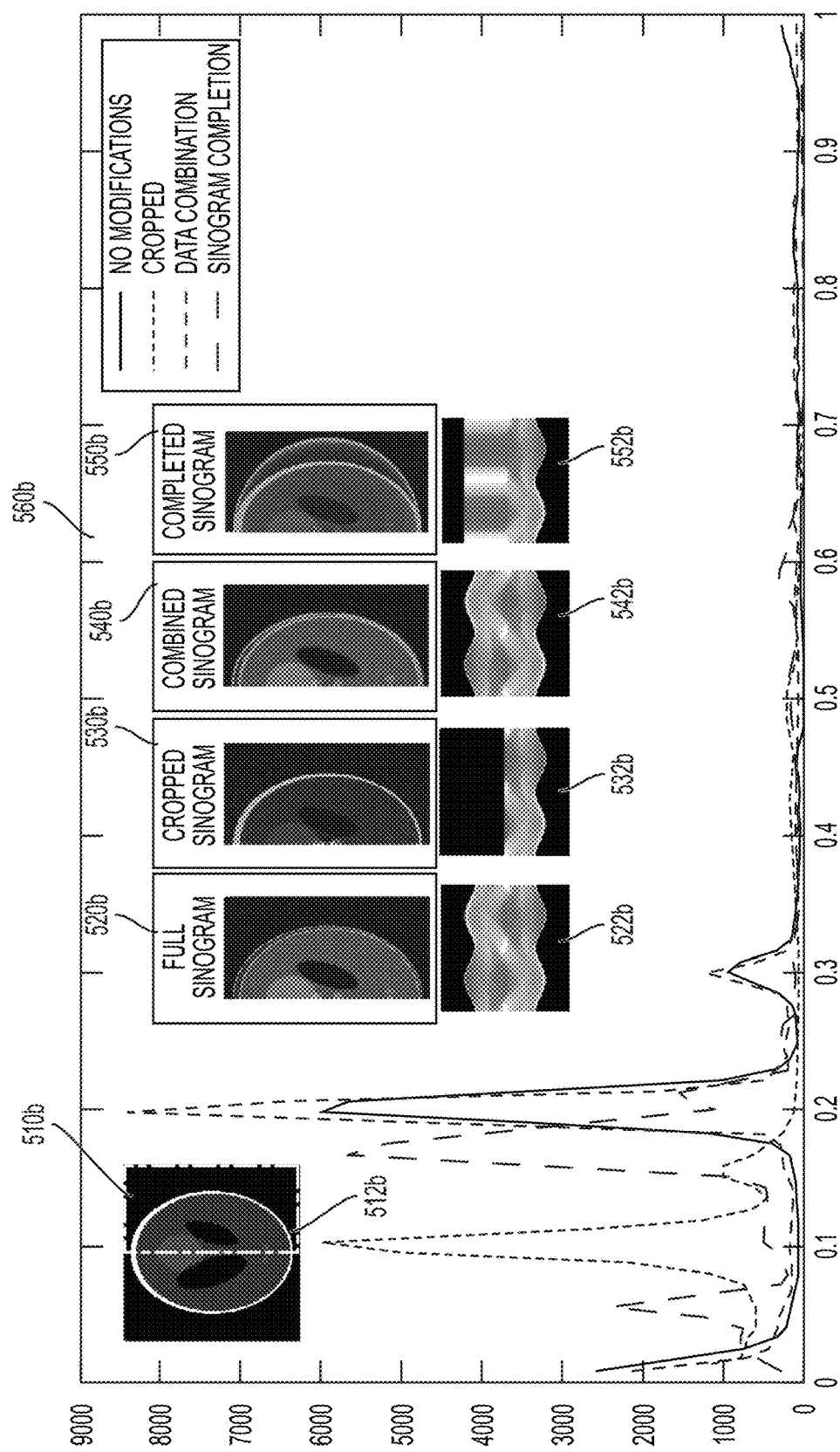
FIG. 5B depicts region of interest (ROI) histograms from results obtained using the data combination and data completion methods of FIGS. 3 and 4 for an offset-based crop.

FIG. 5A and FIG. 5B show data comparing different approaches for completion of sinograms that are truncated due to detector crop. The data in FIG. 5A and FIG. 5B compare the cases of (i) a full sinogram, (ii) a sinogram truncated due to detector crop, (iii) sinogram completion via the sinogram combination approach described above with respect to FIG. 3, and (iv) sinogram completion via the padding approach described above with respect to FIG. 4.

FIG. 5A shows data for a centered detector crop. Image 510a shows the object, along with the region of interest (indicated with white dash-dot lines) corresponding to the detector field of view. A full, sinogram 522a is shown, along with a reconstruction 520a of the object obtained using the full sinogram. Sinogram 532a is an unprocessed truncated sinogram. Image 530a shows a reconstruction of the object obtained using the unprocessed truncated sinogram 532a. Sinogram 542a is a completed sinogram obtained using the sinogram combination approach (e.g. process 300) described above with respect to FIG. 3 for automated completion of the truncated sinogram 532a. A reconstruction obtained using sinogram 542a is shown in image 540a. Sinogram 552a is another completed sinogram, obtained using the sinogram padding approach (e.g. process 400) described above with respect to FIG. 4. A reconstruction obtained using the completed sinogram is shown in image 550a. Graph 560a plots histograms for each of the four different reconstruction obtained using a different sinogram. In graph 560a, the x-axis represents a normalized intensity of points in the reconstructions and the y-axis represents frequency. Accordingly, each of the histograms shows frequencies with which points having different values of a normalized intensity occur in a given reconstruction. The histogram (long dashed lines, "DATA COMBINATION" in the legend) for the reconstruction 540a obtained from the sinogram 542a completed using the data combination approach matches closely with the histogram (solid lines) for the ideal reconstruction 520a obtained from the full sinogram, indicating accurate reconstruction obtained via the combination approach.

FIG. 5B presents data similar to the data shown in FIG. 5A, but for an offset detector crop. Image 510b shows the object, along with the region of interest (indicated with white dash-dot lines) corresponding to the detector field of view. As shown in image 510b, the region of interest corresponding to the detector field of view is offset to the right side of the object. A full, sinogram 522b is shown, along with a reconstruction 520b of the object obtained using the full sinogram. Sinogram 532b is an unprocessed truncated sinogram. Image 530b shows a reconstruction of the object obtained using the unprocessed truncated sinogram 532b. Sinogram 542b is a completed sinogram obtained using the sinogram combination approach (e.g. process 300) described above with respect to FIG. 3 for automated completion of the truncated sinogram 532b. A reconstruction obtained using singoram 542b is shown in image 540b. Sinogram 552b is another completed sinogram, obtained using the sinogram padding approach (e.g. process 400) described above with respect to FIG. 4. A reconstruction obtained using the completed sinogram is shown in image 550b. Graph 560b plots histograms for each of the four different reconstruction obtained using a different sinogram. In graph 560b, the x-axis represents a normalized intensity of points in the reconstructions and they-axis represents frequency. Accordingly, each of the histograms shows frequencies with which points having different values of a normalized intensity occur in a given reconstruction. The histogram (long dashed lines, "DATA COMBINATION" in the legend) for the reconstruction 540b obtained from the sinogram 542b completed using the data combination approach matches closely with the histogram (solid lines) for the ideal reconstruction 520b obtained from the full sinogram, indicating accurate reconstruction obtained via the combination approach.

Sinogram Completion Using Summed Data

Figure 6:
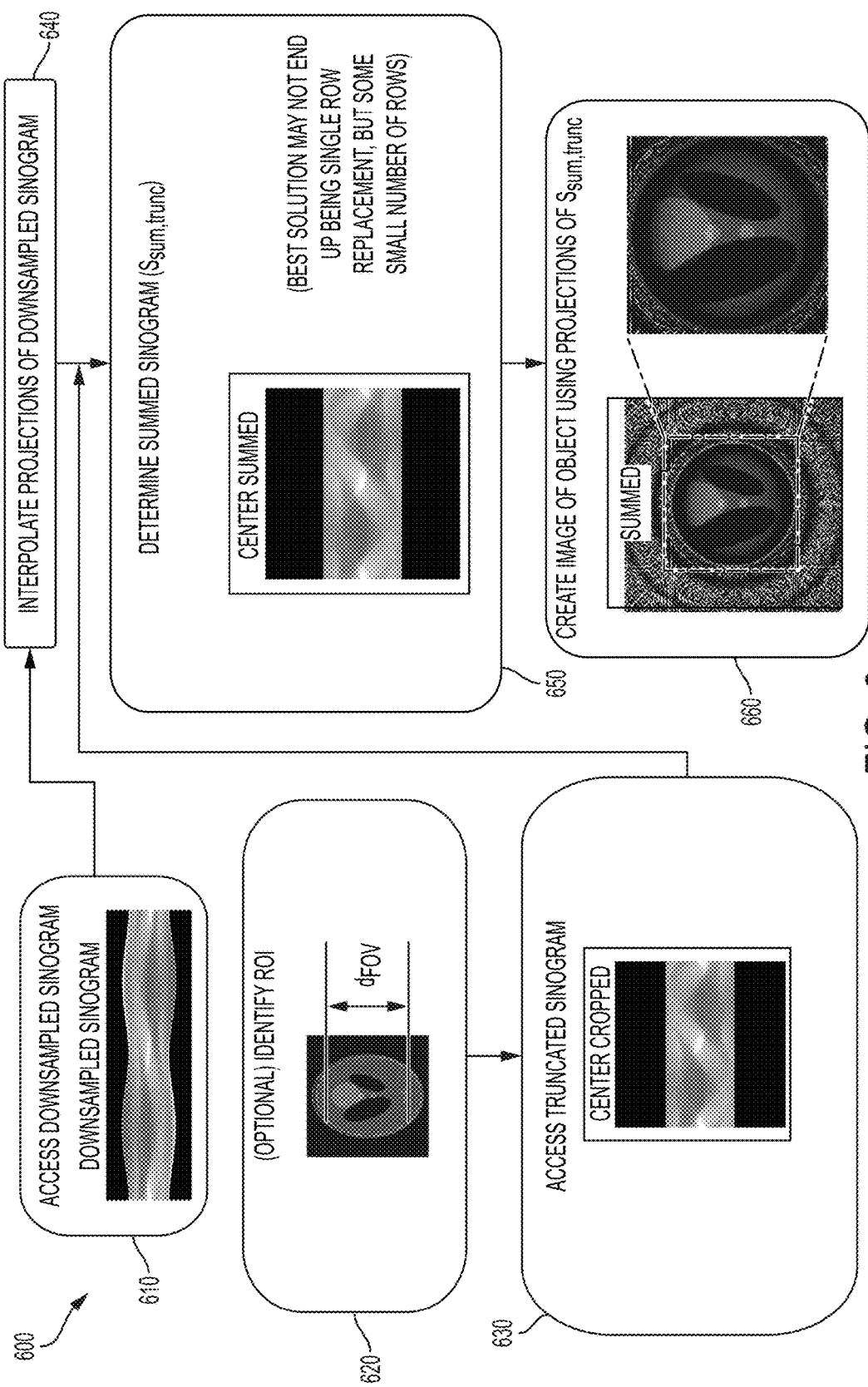
FIG. 6 is a flow diagram depicting a "completion by combination" method for automated sinogram completion according to an illustrative embodiment, where the sinogram to be completed is truncated due to a detector crop.

FIG. 6 shows a block flow diagram of an example of a process 600 for automated completion of a sinogram that is truncated due to detector crop. Process 600 uses a data summation approach for sinogram completion by combination.

In one step 610 in the process, a downsampled sinogram is accessed (e.g., full panel bin 4 projections are acquired to obtain a downsampled sinogram, $S_{4\times4}$).

In another step 630, truncated projections (e.g., bin 1 projections) are acquired using a region of interest for the CT field of view, $d_{FOV}$, in order to obtain a truncated sinogram (e.g., $S_{1\times1,trunc}$). The truncated sinogram (e.g., $S_{1\times1,trunc}$) is a detector cropped sinogram and, accordingly, does not include data representing signal detected by regions of the detector that are outside the region of interest.

In certain embodiments, the region of interest corresponding to the CT field of view is identified in an optional step 620. The region of interest may be identified using a photograph of the object, such as an optical image, a fluorescence image, a bioluminescence image, or any other light-based image. The region of interest may be identified using a low resolution CT image reconstructed using the downsampled sinogram, $S_{4\times4}$.

In certain embodiments, the region of interest is predefined in the CT configuration, and identification of the region of interest is not necessary.

In certain embodiments, the process provides for missing data in the truncated sinogram (e.g., $S_{1\times1,trunc}$) to be filled in, thereby completing the sinogram. The missing data in the truncated sinogram corresponds to the data representing signals detected by regions of the detector (e.g., detector pixels) that are outside the region of interest. In particular, in another step 640, each projection of the downsampled sinogram, (e.g., $S_{4\times4}$), is interpolated (e.g., with bin 1) to obtain an interpolated sinogram, (e.g., $S_{4\times4\_to\_1\times1}$). Data in truncated rows of $S_{1\times1,trunc}$ is replaced with summed data (e.g., summed over rows) outside of the truncation limits from $S_{4\times4\_to\_1\times1}$ to obtain a summed sinogram, $S_{sum,trunc}$.

In certain embodiments, in another step 660, once the summed sinogram, $S_{sum,trunc}$, is obtained, tomographic reconstruction is performed using projections of the summed sinogram, $S_{sum,trunc}$, to obtain a reconstruction of the object.

Post Processing Corrections to Truncated Sinograms

Figure 7:
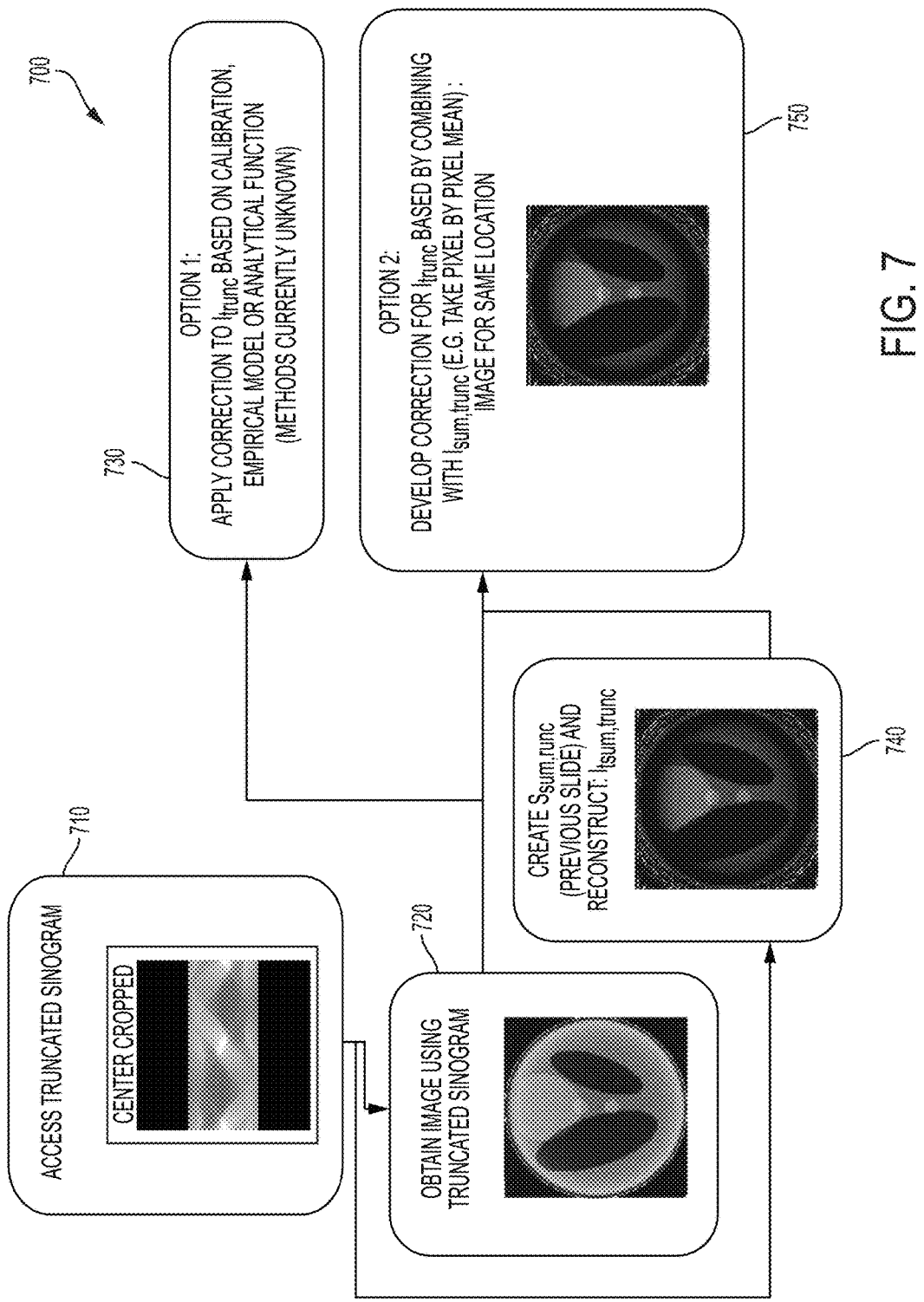
FIG. 7 is a flow diagram depicting a method for performing post-processing corrections for a sinogram truncated due to a detector crop, according to an illustrative embodiment.

FIG. 7 shows a block flow diagram of an example of a process 700 for applying post processing corrections to a sinogram truncated due to a detector crop. In one step 710, a truncated sinogram, $S_{trunc}$, is accessed. In another step, tomographic reconstruction is applied to the truncated sinogram, $S_{trunc}$, to obtain a reconstruction of the object, $I_{trunc}$, from the truncated sinogram, $S_{trunc}$.

In certain embodiments, a post processing step 730 includes applying a correction to the reconstruction obtained from the truncated sinogram ($I_{trunc}$) based on calibration, an empirical model, or an analytical function.

In certain embodiments, the reconstruction, $I_{trunc}$, obtained from the truncated sinogram corresponds to a first reconstruction, and a correction is applied using a second reconstruction obtained using a completed sinogram. The completed sinogram used to obtain the second reconstruction may be obtained via any of the sinogram completion approaches described herein. For example, in step 740 a summed sinogram, $S_{sum,trunc}$, is obtained (e.g. via process 600, described above with respect to FIG. 6) and used to obtain the second reconstruction, $I_{tsum,trunc}$. In certain embodiments, the second reconstruction obtained in step 740 is obtained using a sinogram that has been completed via the sinogram combination approach of process 300, described above with respect to FIG. 3. In certain embodiments, the second reconstruction obtained in step 740 is obtained using a sinogram that has been completed via the sinogram padding approach of process 400, described above with respect to FIG. 4.

A correction is applied to the first reconstruction using the second reconstruction (e.g. $I_{tsum,trunc}$), thereby producing a corrected reconstruction. In certain embodiments, the first reconstruction is combined with the second reconstruction to obtain the corrected reconstruction. For example, the corrected reconstruction can be obtained by taking a pixel by pixel mean between the first and second reconstructions, wherein the value of each pixel in the corrected reconstruction is computed as the average of a first pixel in the first reconstruction and a corresponding second pixel in the second reconstruction.

Figure 8A:
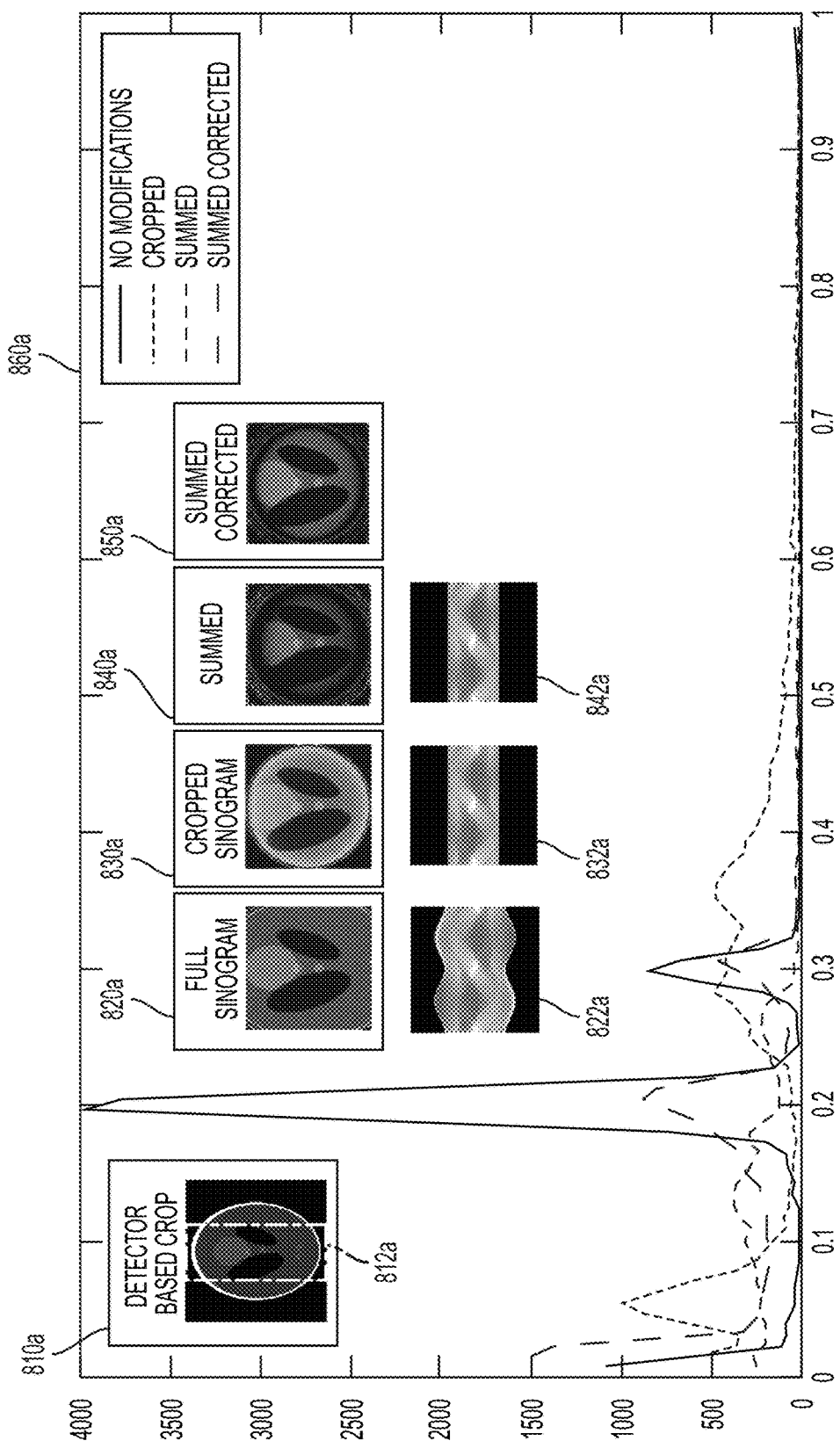
FIG. 8A depicts region of interest (ROI) histograms from results obtained using the completion by combination method of FIG. 6 for a center-based crop.
Figure 8B:
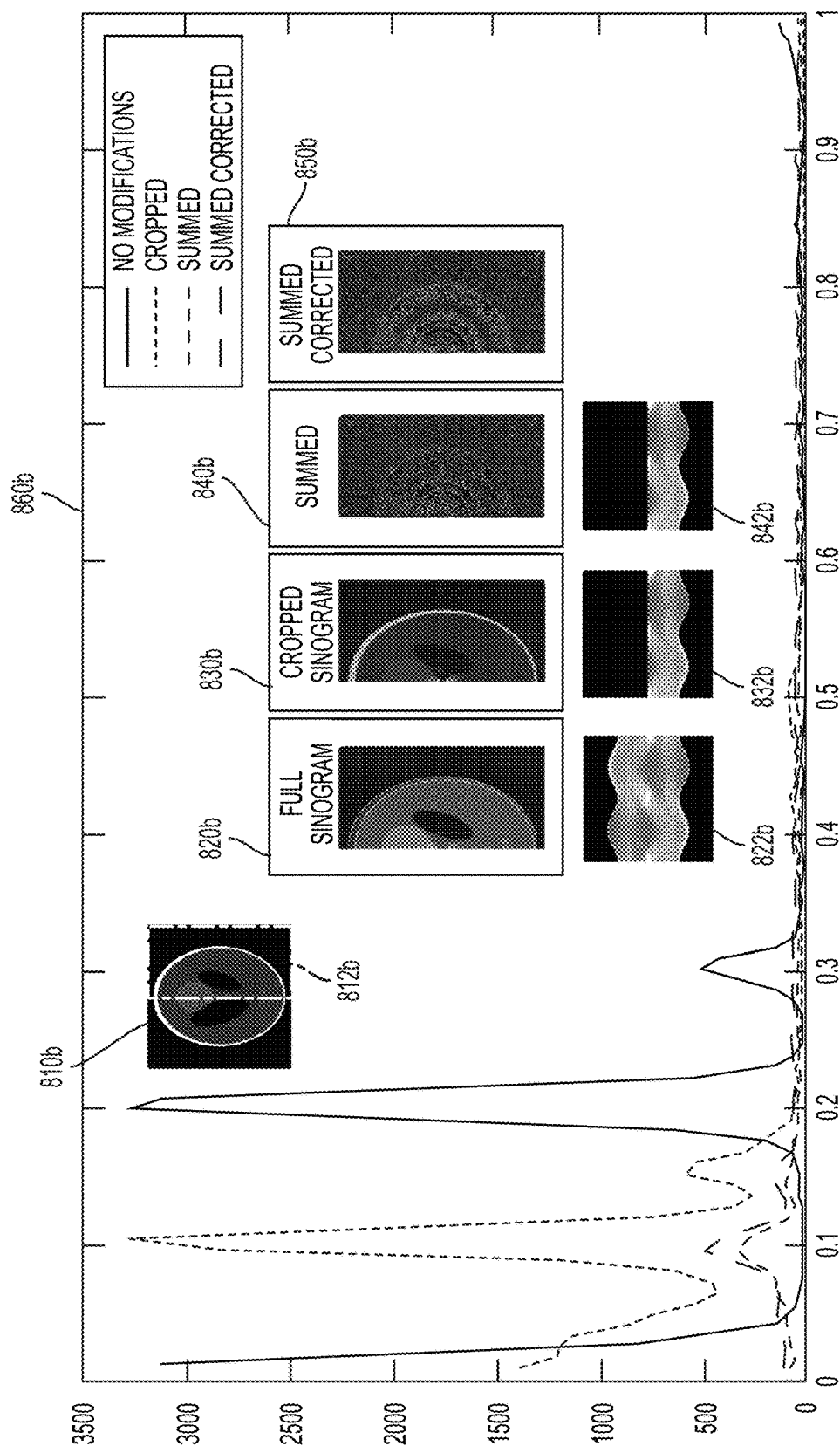
FIG. 8B depicts region of interest (ROI) histograms from results obtained using the completion by combination method of FIG. 6 for an offset-based crop.

FIG. 8A and FIG. 8B show data comparing results obtained using the summation approach of process 600 and results obtained using a post processing correction. Results for a full sinogram and an unprocessed (e.g. not completed) truncated sinogram (due to detector crop) are also shown.

FIG. 8A shows data for a centered detector crop. Image 810a shows the object, along with the region of interest (indicated with white dash-dot lines) corresponding to the detector field of view. A full, sinogram 822a is shown, along with a reconstruction 820a of the object obtained using the full sinogram. Sinogram 832a is an unprocessed truncated sinogram. Image 830a shows a reconstruction of the object obtained using the unprocessed truncated sinogram 832a. Sinogram 842a is a completed sinogram obtained using the data summation approach for sinogram combination (e.g. process 600) described above with respect to FIG. 6 for automated completion of the truncated sinogram 832a. A reconstruction obtained using sinogram 842a is shown in image 840a. Image 850a is a corrected reconstruction obtained by taking a pixel by pixel mean between a reconstruction 830a and reconstruction 840a. Graph 860a plots histograms for each of the four different reconstruction obtained using a different sinogram. In graph 860a, the x-axis represents a normalized intensity of points in the reconstructions and the y-axis represents frequency. Accordingly, each of the histograms shows frequencies with which points having different values of a normalized intensity occur in a given reconstruction. The histogram (long dashed lines, "SUMMED CORRECTED" in the legend) for the corrected reconstruction matches peak locations closely with the histogram (solid lines) for the ideal reconstruction obtained from the full sinogram, indicating the effectiveness of the post processing approach.

FIG. 8B presents data similar to the data shown in FIG. 8A, but for an offset detector crop. Image 810b shows the object, along with the region of interest (indicated with white dash-dot lines) corresponding to the detector field of view. As shown in image 810b, the region of interest corresponding to the detector field of view is offset to the right side of the object. A full, sinogram 822b is shown, along with a reconstruction 820b of the object obtained using the full sinogram. Sinogram 832b is an unprocessed truncated sinogram. Image 830b shows a reconstruction of the object obtained using the unprocessed truncated sinogram 832b. Sinogram 842b is a completed sinogram obtained using the data summation approach for sinogram combination (e.g. process 600) described above with respect to FIG. 6 for automated completion of the truncated sinogram 832a. A reconstruction obtained using sinogram 842a is shown in image 840a. Image 850a is a corrected reconstruction obtained by taking a pixel by pixel mean between a reconstruction 830a and reconstruction 840a. Graph 860a plots histograms for each of the four different reconstruction obtained using a different sinogram. In graph 860b, the x-axis represents a normalized intensity of points in the reconstructions and the y-axis represents frequency. Accordingly, each of the histograms shows frequencies with which points having different values of a normalized intensity occur in a given reconstruction.

In certain embodiments, two reconstructions, each obtained from a sinogram with a different resolution, are combined in post processing. For example, in certain embodiments, a first reconstruction, referred to as a background reconstruction ($I_{Background}$), is obtained using a low-resolution projections of a downsampled sinogram and a second reconstruction, referred to as a detail reconstruction ($I_{Detail}$), is obtained using a high-resolution projections of a truncated sinogram. The two reconstructions can then be combined via a pixel-by-pixel weighted sum, wherein a given pixel of the final, corrected reconstruction is computed as a weighted sum of corresponding background and detail pixels (e.g., $I(x)=I_{Background}(x)+w(x)\times I_{Detail}(x)$, where $w(x)$ is the weighting function, which may vary as a function of position within the reconstruction, and x is a variable represent position (e.g., a given pixel) within the reconstruction).

Completion of Truncated Sinograms Due to Subvolume Crop

Completion by Sinogram Combination

Figure 9:
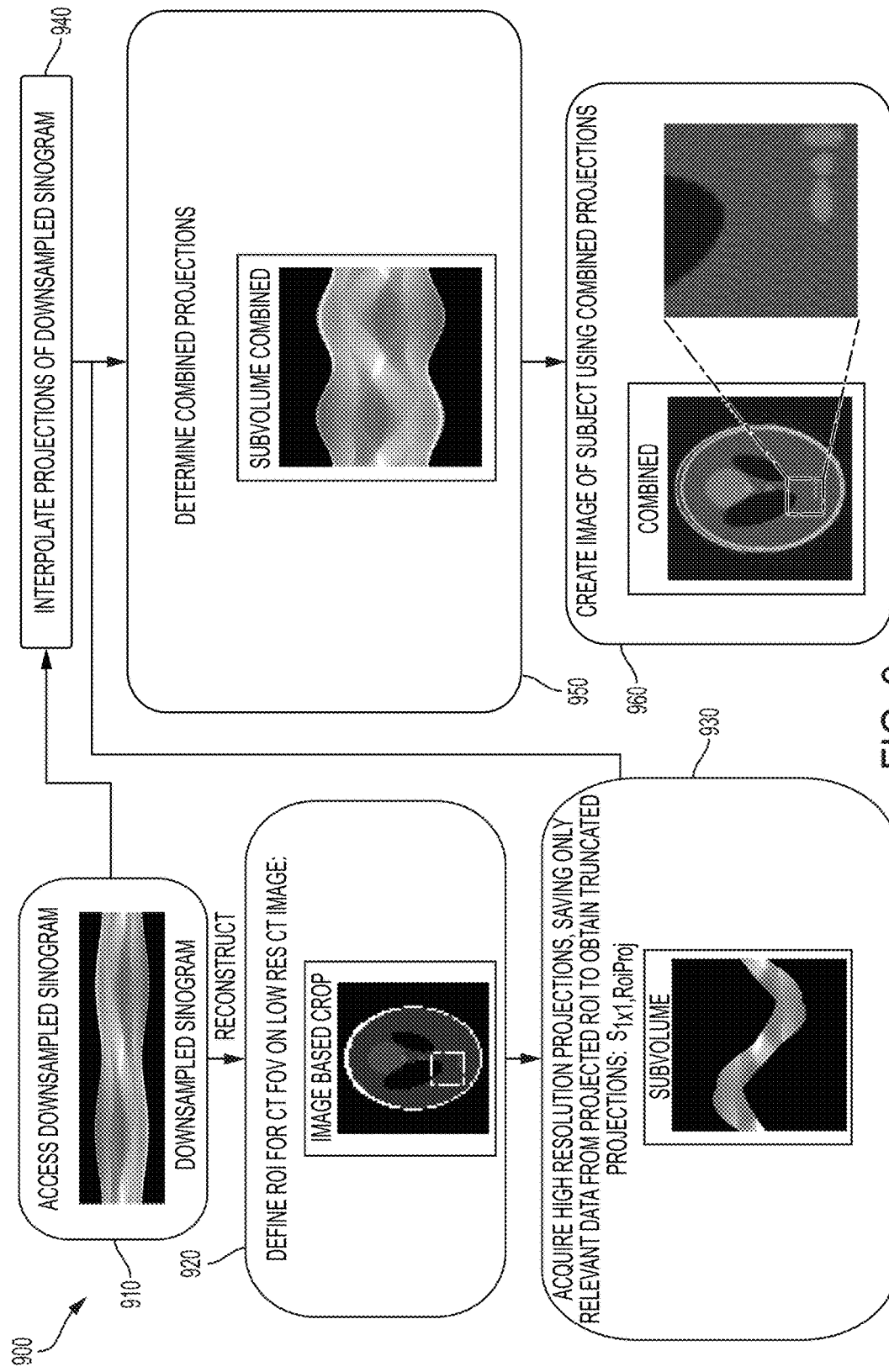
FIG. 9 is a flow diagram depicting a "data combination" method for automated sinogram completion according to an illustrative embodiment, where the sinogram to be completed is truncated due to a subvolume crop.

FIG. 9 shows a block flow diagram of a process 900 for automated completion of a sinogram that is truncated due to a subvolume crop using a sinogram combination approach. In a first step 910, full panel bin 4 projections are acquired to obtain a downsampled sinogram, $S_{4\times 4}$. In another step 920, a region of interest for the CT field of view is identified on a low resolution CT image. In certain embodiments, the low resolution CT image is a reconstruction obtained by performing tomographic reconstruction on the downsampled sinogram.

In another step 930, truncated bin 1 projections are acquired, and only data from the projected region of interest is saved to disk, thereby obtaining a truncated sinogram, $S_{1\times 1,RoiProj}$. The truncated sinogram, $S_{1\times 1,RoiProj}$, is truncated due to a subvolume crop and, accordingly, for a given angle, only includes data from a portion of distances along the projection direction. The specific portion of distances varies with the angle.

Figure 22:
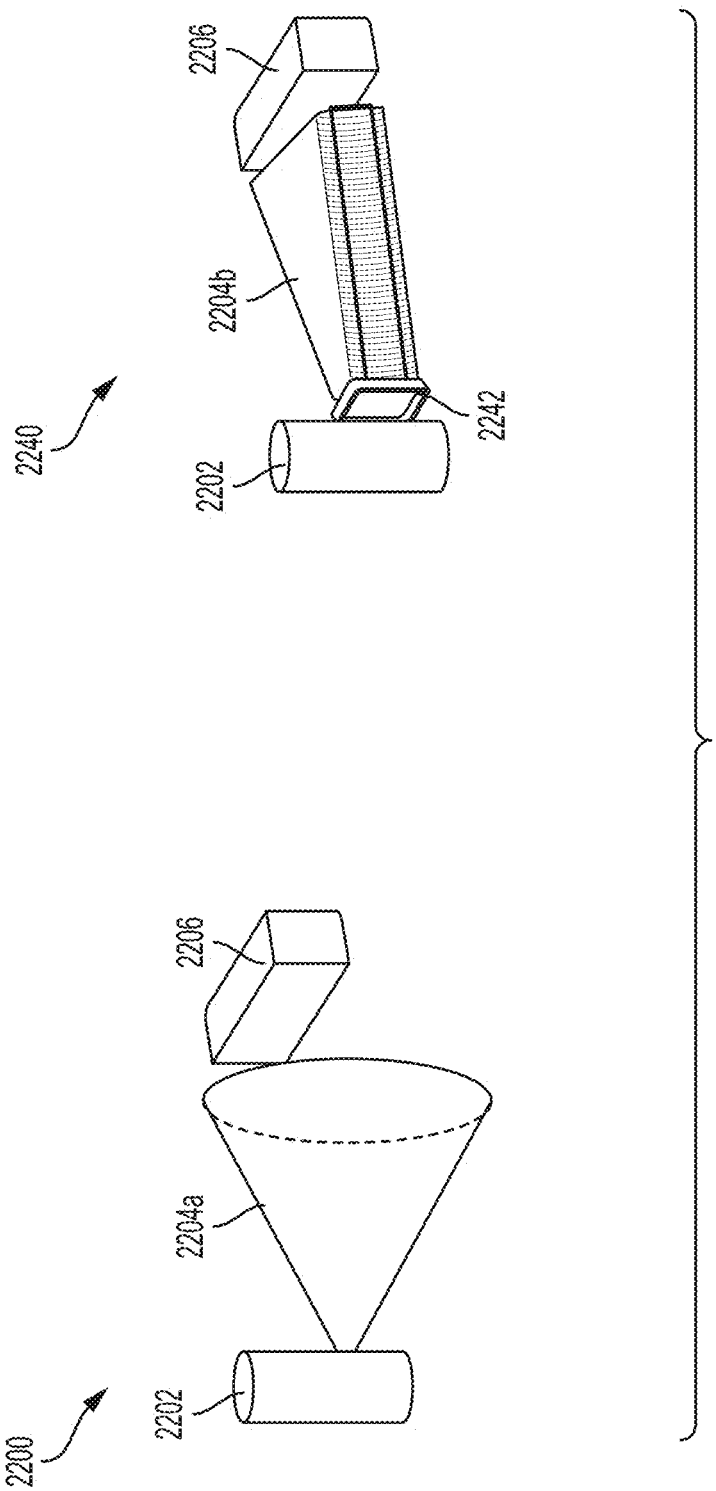
FIG. 22 is a depiction illustrating use of a traditional X-ray collimator, according to an illustrative embodiment.

In certain embodiments, truncated projections are acquired using a multi-angle scan of the subject in which a variable collimator is used to selectively illuminate the ROI of the subject as the illumination angle is varied over the course of the multi-angle scan. FIG. 22 is a depiction illustrating use of a traditional X-ray collimator to shape a beam of X-ray radiation. An example system 2200 comprising an X-ray source 2202 and an X-ray detector 2206 without a collimator results in a large, conical X-ray beam 2204a produced by the X-ray source 2202. In an example system 2240 in which a traditional collimator (e.g., a dumping ring) is used, the collimator is positioned after the X-ray source 2202, in the path of the X-ray beam 2204b. The collimator blocks a portion of the X-ray beam, such that instead of a large conical beam, narrower, fan-like beam 2204b is produced (e.g., which matches the detector area).

Figure 23:
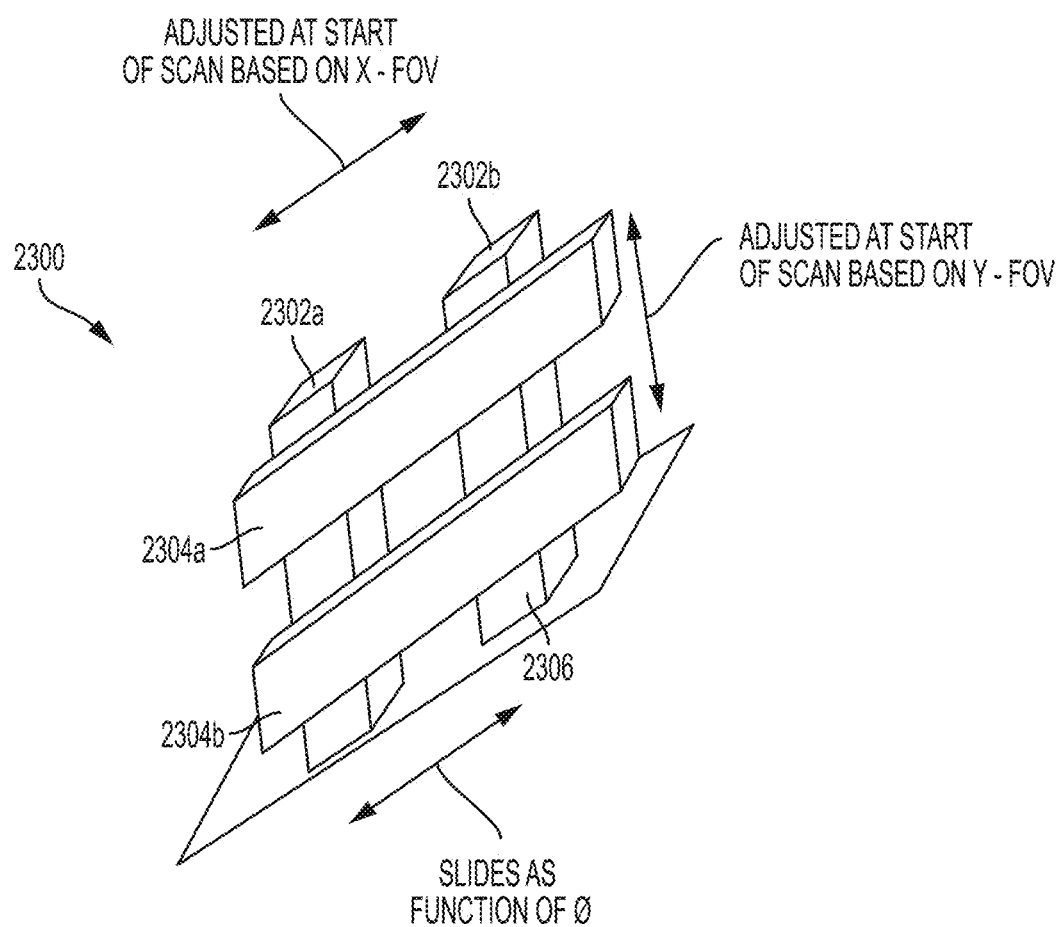
FIG. 23 is a schematic showing an adjustable X-ray collimator for illuminating a region of an object during a multi-angle scan of the object, according to an illustrative embodiment.

Turning to FIG. 23, in certain embodiments, a variable collimator 2300 is used to limit the dimensions of an X-ray beam in an adjustable fashion. As shown in the schematic of FIG. 23, in certain embodiments, variable collimator comprises a first set of adjustable shutters 2302a and 2302b, and a second set of adjustable shutters 2304a and 2304b. The adjustable shutters of the first and second sets of adjustable shutters are substantially opaque to X-ray radiation such that when the variable collimator is placed in the path of the X-ray beam, the adjustable shutters block portions of the X-ray beam, thereby limiting its extent. In certain embodiments, the first set of adjustable shutters are oriented vertically, and are movable along a first axis. Adjustment of the first set of shutters along the first axis allows the extent of the X-ray beam along the first axis to be varied. In certain embodiments, the first axis is aligned with a first axis of the detector, such as an x-axis of the detector. In certain embodiments, the second set of adjustable shutters are oriented horizontally, and are movable along a second axis that is orthogonal to the first axis. Adjustment of the second set of shutters along the second axis allows the extent of the X-ray beam along the second axis to be varied. In certain embodiments, the second axis is aligned with a second axis of the detector, such as any-axis of the detector. Accordingly, adjustment of the first and second sets of adjustable shutters provides for adjustment of a size of the X-ray beam used to illuminate a subject.

In certain embodiments, the adjustable collimator comprises a movable mount that allows a position of the adjustable collimator within the path of the X-ray beam to be varied as a function of angle during multi-angle scanning of a subject. In certain embodiments, variation of the position of the adjustable collimator as a function of angle allows a fixed ROI of the subject to be illuminated even as the position of the ROI relative to the X-ray source varies as the subject is rotated.

In certain embodiments, by virtue of selective illumination of the ROI provided for by the variable collimator, illumination of regions of the subject outside of the ROI with potentially harmful X-ray radiation is avoided. For example, in certain embodiments, a first low-dose scan to determine the desired ROI, and then a second high-dose scan that selectively illuminates the desired ROI is used to obtain a sinogram for the ROI (e.g., a subvolume cropped sinogram). In certain embodiments, a stable and repeatable scan trajectory is used to avoid misalignment between the two scans (e.g., the first, low-dose scan and the second, high-dose scan).

In certain embodiments, the process provides for filling in of missing data in the truncated sinogram, $S_{1 \times 1, RoiProj}$, thereby completing the sinogram. In particular, in another step, 940, in order to complete the truncated sinogram, each projection of the downsampled sinogram, $S_{4 \times 4}$, is interpolated with bin 1 to obtain an interpolated sinogram, $S_{4 \times 4\_to\_1 \times 1}$. In another step 950, empty columns in the truncated sinogram $S_{1 \times 1, RoiProj}$, are replaced with interpolated data from $S_{4 \times 4\_to\_1 \times 1}$ to obtain a combined sinogram, $S_{combined}$. In certain embodiments, in another step 960, once $S_{combined}$ is obtained, projections of $S_{combined}$ are used to obtain a reconstruction of the object.

Completion by Padding

Figure 10:
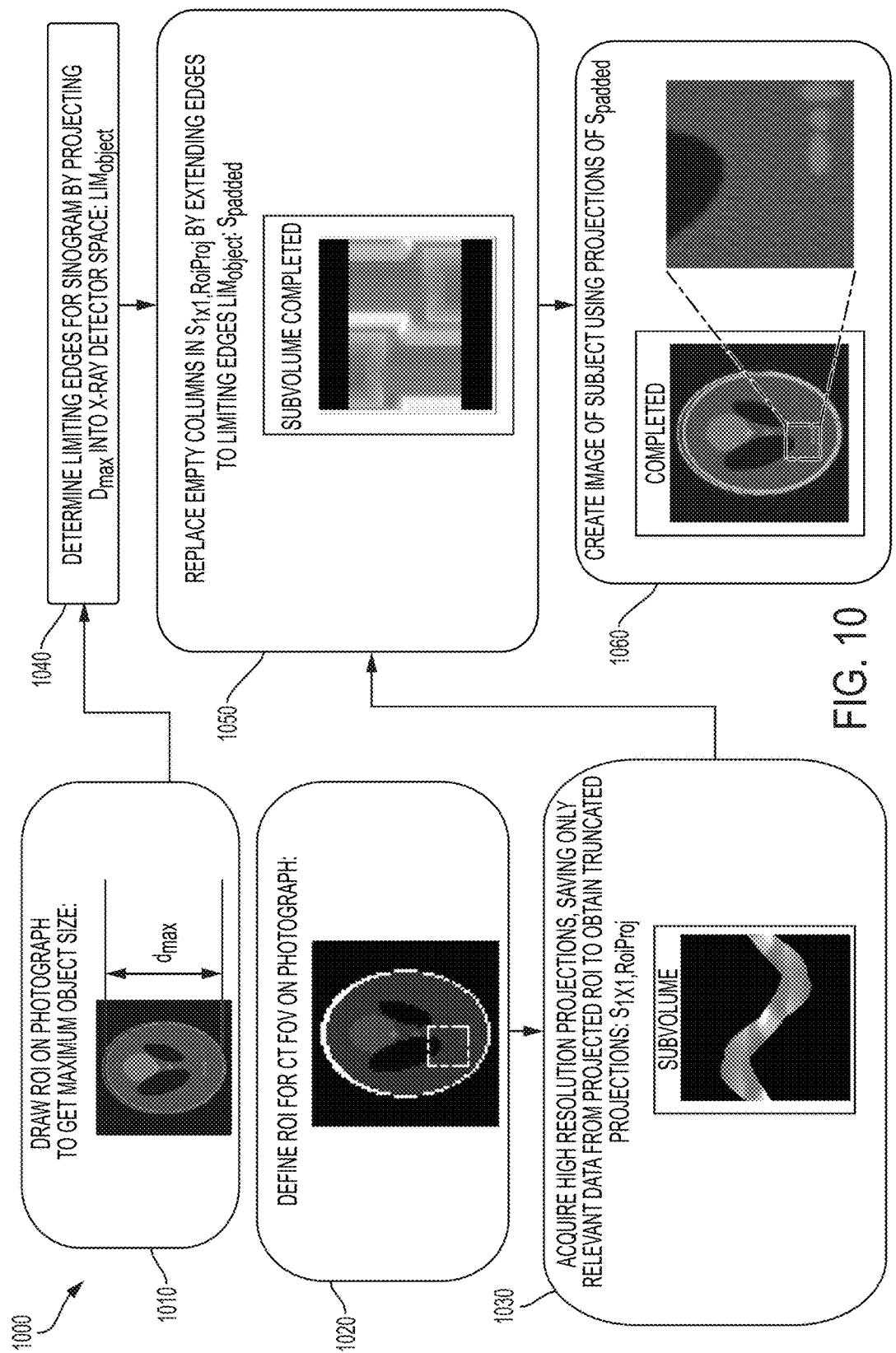
FIG. 10 is a flow diagram depicting a "data completion by padding" method for automated sinogram completion according to an illustrative embodiment, where the sinogram to be completed is truncated due to a subvolume crop.

FIG. 10 is a block flow diagram of a process 1000 for automated completion of a sinogram that is truncated due to a subvolume crop. Process 1000 uses a padding approach for sinogram completion. In a first step in the process, a region of interest is identified on a photograph of the object to determine a maximum object size, $d_{max}$.

In another step 1020, a second region of interest corresponding to the CT field of view is identified in a photograph of the object. In certain embodiments, the photograph of the object used to identify the second region of interest is as an optical image, a fluorescence image, a bioluminescence image, or any other light-based image.

In another step 1030, truncated bin 1 projections are acquired, and only data from the projected second region of interest is saved to disk. The saved data from the projected region of interest corresponds to a sinogram that is truncated due to a subvolume crop, $S_{1 \times 1, RoiProj}$. As described above with respect to FIG. 9, FIG. 22, and FIG. 23, in certain embodiments, an adjustable collimator is used to selectively illuminate the ROI of the subject during a multi-angle scan of the subject in which the projections of the truncated sinogram are acquired.

In certain embodiments, the process 1000 provides for filling in missing data from the truncated sinogram, $S_{1 \times 1, RoiProj}$, thereby completing the sinogram. The process 1000 fills in the missing data via a data padding approach. In particular, in another step 1040, the limiting columns, $LIM_{object}$ are determined by projecting $d_{max}$ into the x-ray detector space. In another step 1050, empty columns in $S_{1 \times 1, trunc}$ are replaced by extending the edges of $S_{1 \times 1, trunc}$ to the limiting edges, $LIM_{object}$ (e.g., via extrapolation), in order to obtain a completed sinogram, $S_{padded}$.

In certain embodiments, once the completed sinogram, $S_{padded}$ is obtained, $S_{padded}$ is used to obtain a reconstruction of the object (460).

Figure 11:
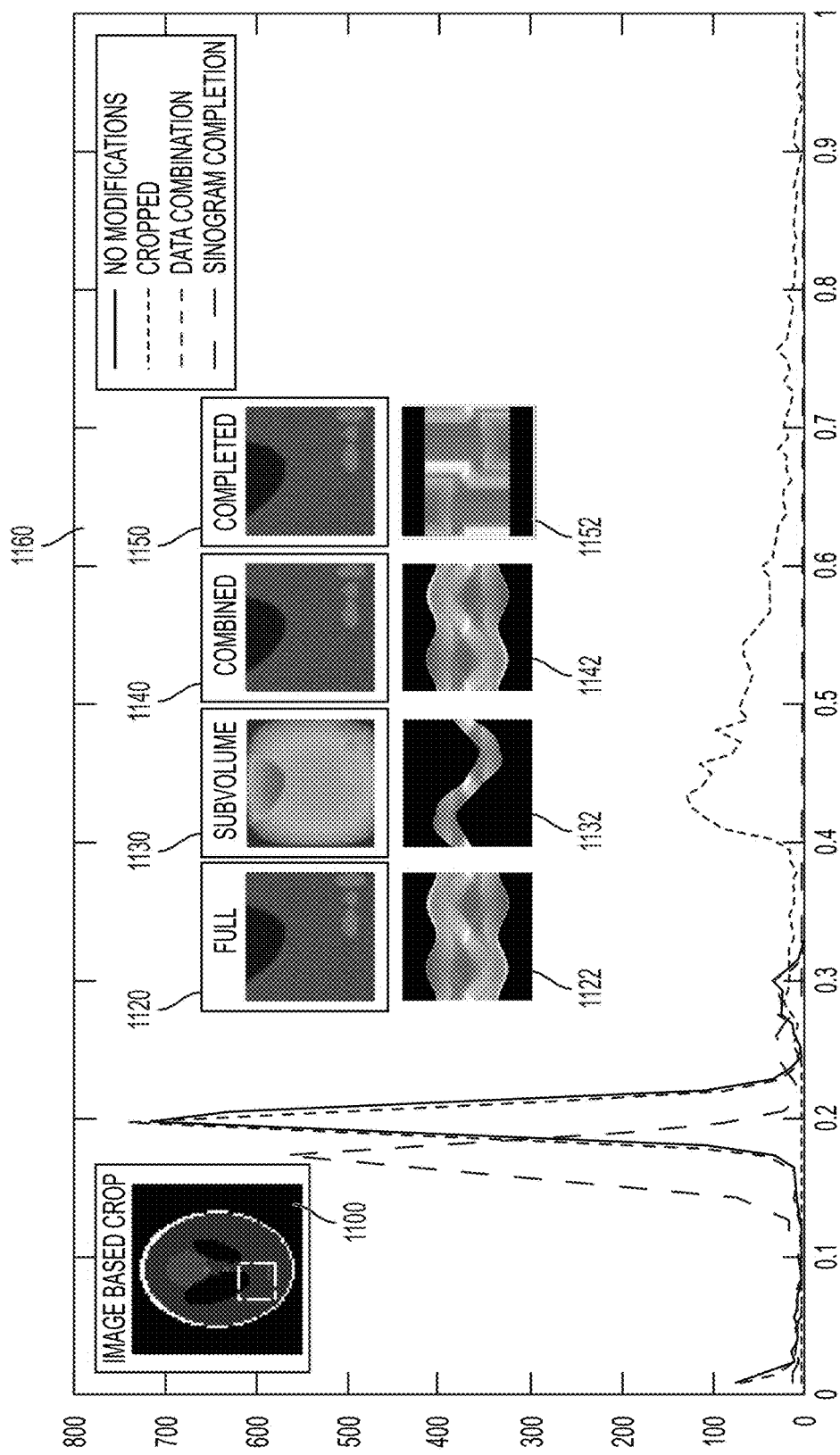
FIG. 11 depicts region of interest (ROI) histograms from results obtained using the methods of FIGS. 9 and 10 for a subvolume crop.

Comparison of Completion by Combination and Completion by Padding Approaches for Sinogram Completion FIG. 11 presents data evaluating the results of different approaches for completion of a truncated sinogram due to a subvolume crop. The data in FIG. 11 compare the cases of (i) a full sinogram, (ii) a sinogram truncated due to a subvolume crop, (iii) sinogram completion via the sinogram combination approach described above with respect to FIG. 9, and (iv) sinogram completion via the padding approach described above with respect to FIG. 10.

Image 1110 shows the object along with the region of interest (indicated with white dash-dot lines). An full sinogram 1122 is shown, along with a reconstruction 1120 of the region of interest obtained using the full sinogram. Sinogram 1132 is an unprocessed (e.g. not completed) truncated sinogram (due to a subvolume crop). Image 1130 is a reconstruction of the region of interest obtained using the unprocessed truncated sinogram 1132. Sinogram 1142 is a completed sinogram, obtained via the data combination approach described above with respect to FIG. 9. Image 1140 shows a reconstruction of the region of interest obtained using the completed sinogram 1142. Sinogram 1152 is an example of a completed sinogram obtained via the data padding approach described above with respect to FIG. 10. Image 1150 shows a reconstruction obtained using the sinogram 1152 completed via the data padding approach. Graph 1160 plots histograms for each of the four different reconstructions obtained using the four different sinograms. The histogram (long dashed lines, "DATA COMBINATION" in the legend) of the reconstruction 1140 obtained using the data completion approach described above with respect to FIG. 9 matches closely with the histogram (solid lines) of the reconstruction 1120 obtained using the full sinogram, indicating accurate reconstruction obtained via the combination approach.

Sinogram Completion Via an Iterative Reconstruction Approach

Figure 12:
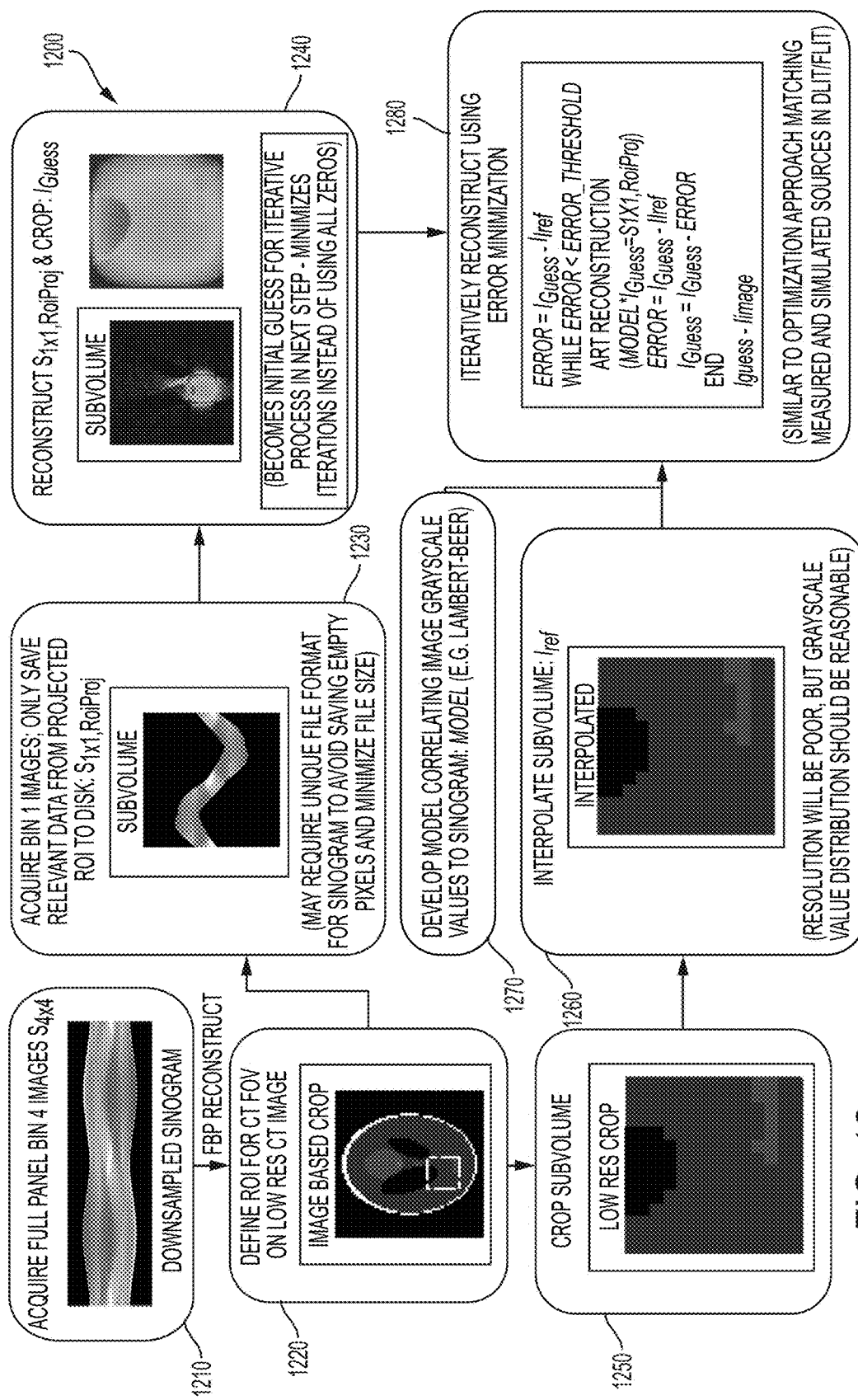
FIG. 12 depicts combined filtered back projection (FBP) reconstruction and iterative reconstruction on a subvolume, according to an illustrative embodiment.

FIG. 12 shows a block flow diagram of an example process 1200 for completion of a sinogram truncated due to a subvolume crop using a combined filtered back projection (FBP) and iterative reconstruction approach. In a first step 1210, a downsampled sinogram, $S_{4 \times 4}$, is obtained from full panel bin 4 projections.

In another step 1220, a region of interest for the CT field of view is identified on a low resolution CT image. In certain embodiments, the low resolution CT image is obtained by reconstructing the downsampled sinogram, for example, via filtered back projection (FBP).

In another step 1230, truncated bin 1 images are acquired, and only data from the projected region of interest is saved to disk, thereby obtaining a truncated sinogram, $S_{1 \times 1, RoiProj}$. The truncated sinogram, $S_{1 \times 1, RoiProj}$, is truncated due to a subvolume crop and, accordingly, for a given angle, only includes data from a portion of distances along the projection direction. The specific portion of distances varies with the angle.

As described above with respect to FIG. 9, FIG. 22, and FIG. 23, in certain embodiments, an adjustable collimator is used to selectively illuminate the ROI of the subject during a multi-angle scan of the subject in which the projections of the truncated sinogram are acquired.

In another step 1240, a reconstruction is obtained using the truncated sinogram obtained in step 1230, and then cropped. The cropped region of the reconstruction corresponds to the region of interest identified in the low resolution CT image. The cropped region of the reconstruction, $I_{Guess}$, can be used as an initial guess in an iterative reconstruction process (e.g. in other steps of process 1200).

In another step 1250, a subvolume corresponding to the identified region of interest of the low resolution CT image is cropped to obtain a low resolution cropped image of the region of interest. In another step, 1260, the cropped image is then interpolated (e.g. spatially) to obtain a reference image of the region of interest, $I_{ref}$.

In another step, iterative image reconstruction is performed using the reference image, $I_{ref}$, and the initial guess, $I_{Guess}$. In certain embodiments, in another step 1270, a model that correlates image grayscale values to sinogram data is established, and then used in the iterative reconstruction process of step 1280. In certain embodiments, the model that correlates image grayscale values to sinogram data is a Lambert-Beer model. For example, in certain embodiments, a tomographic reconstruction algorithm, such as an Algebraic Reconstruction Technique (ART) is used to obtain an temporary image of the ROI based on the initial guess, the truncated sinogram, and the model correlating sinogram data to image grayscale values. A difference image between the temporary image and the reference image is determined (e.g., a pixel by pixel difference), and used to determine an error value (e.g., a maximum difference; e.g., an average difference). The error value is compared to a threshold value. If the error value is greater than the threshold value, the difference image is subtracted from the initial guess to update the initial guess. The tomographic reconstruction algorithm is then repeated using the new initial guess, to determine a new temporary image, and a new difference image is determined. A new error value is determined and compared with the threshold value. This process is repeated until the error value is determined to be below the threshold value.

System Components

Figure 13:
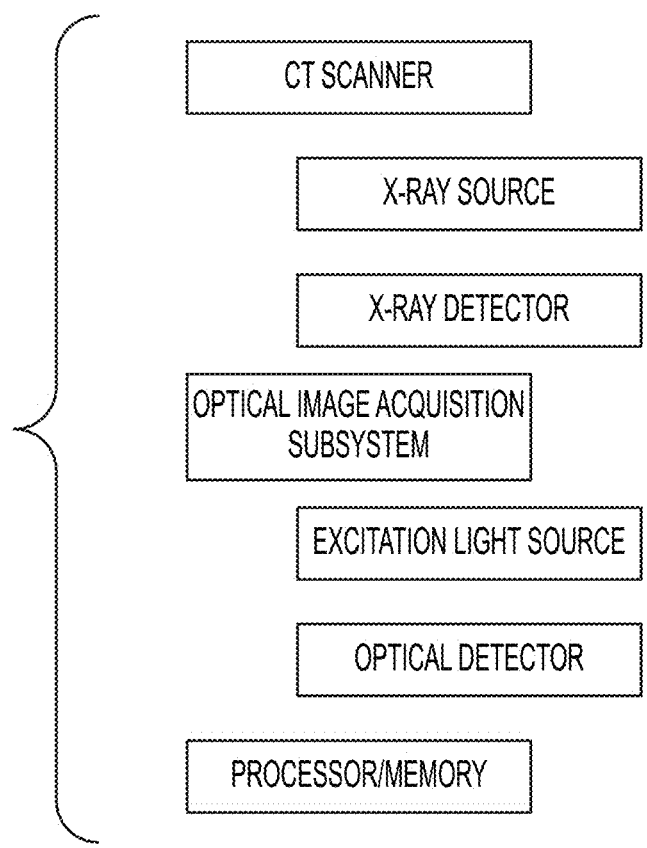
FIG. 13 is a block diagram of a system for performing the methods described herein, according to an illustrative embodiment.

FIG. 13 is a block diagram of a system for performing the methods described herein, according to an illustrative embodiment. In certain embodiments, the system comprises a CT scanner. In certain embodiments, the CT scanner comprises an X-ray source and an X-ray detector. In certain embodiments, the system comprises an Optical image acquisition subsystem. In certain embodiments, the Optical image acquisition subsystem comprises an excitation light source and an optical detector. In certain embodiments, the system comprises a processor and a memory. In certain embodiments, the system comprises an adjustable collimator as described above with respect to FIG. 23.

Computer System and Network Environment

Figure 14:
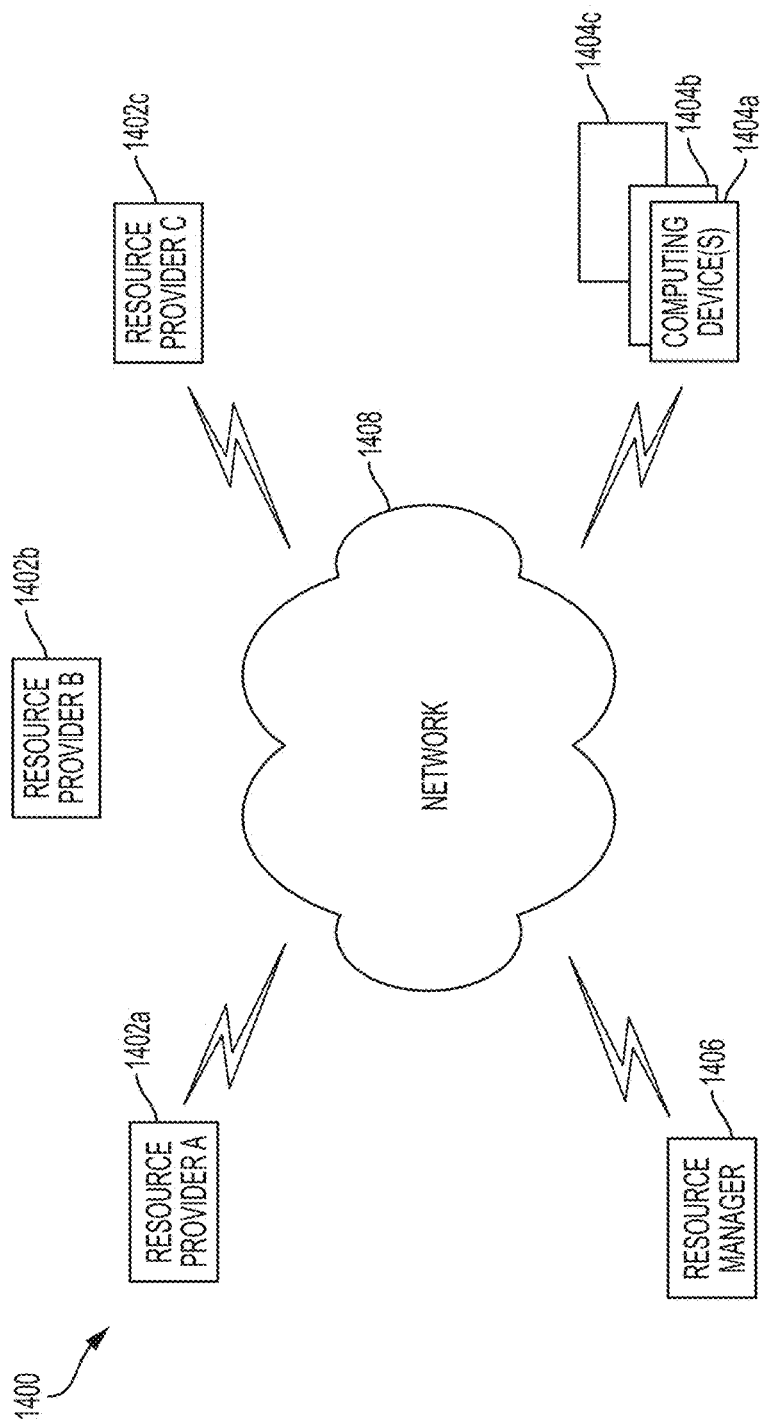
FIG. 14 is a block diagram of an example computing device and an example mobile computing device, for use in illustrative embodiments of the present disclosure.

FIG. 14 shows an illustrative network environment 1400 for use in the methods and systems described herein. In brief overview, referring now to FIG. 14, a block diagram of an exemplary cloud computing environment 1400 is shown and described. The cloud computing environment 1400 may include one or more resource providers 1402a, 1402b, 1402c (collectively, 1402). Each resource provider 1402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1402 may be connected to any other resource provider 1402 in the cloud computing environment 1400. In some implementations, the resource providers 1402 may be connected over a computer network 1408. Each resource provider 1402 may be connected to one or more computing device 1404a, 1404b, 1404c (collectively, 1404), over the computer network 1408.

The cloud computing environment 1400 may include a resource manager 1406. The resource manager 1406 may be connected to the resource providers 1402 and the computing devices 1404 over the computer network 1408. In some implementations, the resource manager 1406 may facilitate the provision of computing resources by one or more resource providers 1402 to one or more computing devices 1404. The resource manager 1406 may receive a request for a computing resource from a particular computing device 1404. The resource manager 1406 may identify one or more resource providers 1402 capable of providing the computing resource requested by the computing device 1404. The resource manager 1406 may select a resource provider 1402 to provide the computing resource. The resource manager 1406 may facilitate a connection between the resource provider 1402 and a particular computing device 1404. In some implementations, the resource manager 1406 may establish a connection between a particular resource provider 1402 and a particular computing device 1404. In some implementations, the resource manager 1406 may redirect a particular computing device 1404 to a particular resource provider 1402 with the requested computing resource.

Figure 15:
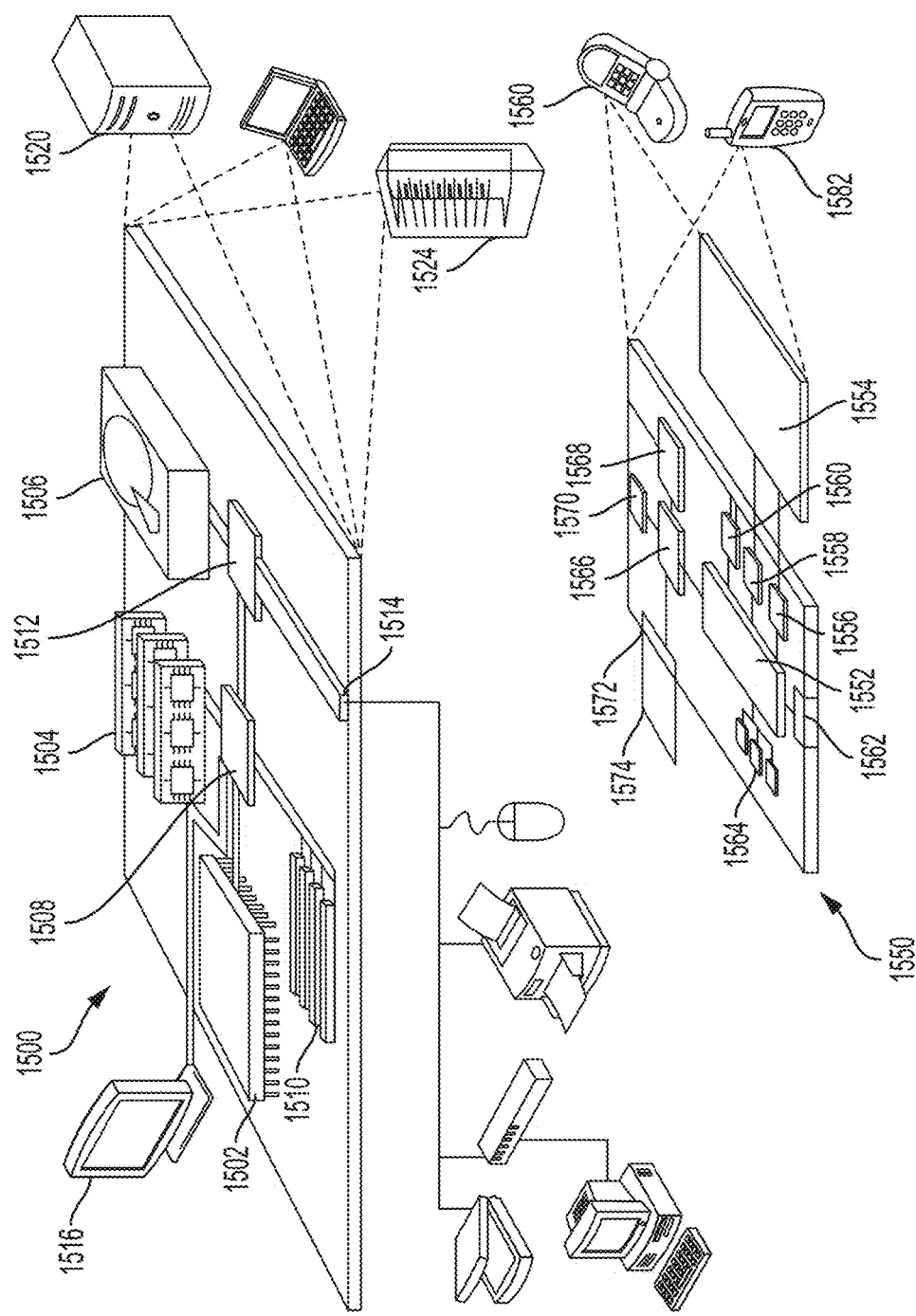
FIG. 15 is a block diagram of an example computing environment, for use in illustrative embodiments of the present disclosure.

FIG. 15 shows an example of a computing device 1500 and a mobile computing device 1550 that can be used in the methods and systems described in this disclosure. The computing device 1500 is intended to represent various forms of digital computers, such as laptops, desktops, workstations, personal digital assistants, servers, blade servers, mainframes, and other appropriate computers. The mobile computing device 1550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and may be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1504 stores information within the computing device 1500. In some implementations, the memory 1504 is a volatile memory unit or units. In some implementations, the memory 1504 is a non-volatile memory unit or units. The memory 1504 may also be another form of computer-readable medium, such as a magnetic or optical disk.

The storage device 1506 is capable of providing mass storage for the computing device 1500. In some implementations, the storage device 1506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1502), perform one or more methods, such as those described above. The instructions can also be stored by one or more storage devices such as computer- or machine-readable mediums (for example, the memory 1504, the storage device 1506, or memory on the processor 1502).

The high-speed interface 1508 manages bandwidth-intensive operations for the computing device 1500, while the low-speed interface 1512 manages lower bandwidth-intensive operations. Such allocation of functions is an example only. In some implementations, the high-speed interface 1508 is coupled to the memory 1504, the display 1516 (e.g., through a graphics processor or accelerator), and to the high-speed expansion ports 1510, which may accept various expansion cards (not shown). In the implementation, the low-speed interface 1512 is coupled to the storage device 1506 and the low-speed expansion port 1514. The low-speed expansion port 1514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1520, or multiple times in a group of such servers. In addition, it may be implemented in a personal computer such as a laptop computer 1522. It may also be implemented as part of a rack server system 1524. Alternatively, components from the computing device 1500 may be combined with other components in a mobile device (not shown), such as a mobile computing device 1550. Each of such devices may contain one or more of the computing device 1500 and the mobile computing device 1550, and an entire system may be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 may also be provided with a storage device, such as a micro-drive or other device, to provide additional storage. Each of the processor 1552, the memory 1564, the display 1554, the communication interface 1566, and the transceiver 1568, are interconnected using various buses, and several of the components may be mounted on a common motherboard or in other manners as appropriate.

The processor 1552 can execute instructions within the mobile computing device 1550, including instructions stored in the memory 1564. The processor 1552 may be implemented as a chipset of chips that include separate and multiple analog and digital processors. The processor 1552 may provide, for example, for coordination of the other components of the mobile computing device 1550, such as control of user interfaces, applications run by the mobile computing device 1550, and wireless communication by the mobile computing device 1550.

The processor 1552 may communicate with a user through a control interface 1558 and a display interface 1556 coupled to the display 1554. The display 1554 may be, for example, a TFT (Thin-Film-Transistor Liquid Crystal Display) display or an OLED (Organic Light Emitting Diode) display, or other appropriate display technology. The display interface 1556 may comprise appropriate circuitry for driving the display 1554 to present graphical and other information to a user. The control interface 1558 may receive commands from a user and convert them for submission to the processor 1552. In addition, an external interface 1562 may provide communication with the processor 1552, so as to enable near area communication of the mobile computing device 1550 with other devices. The external interface 1562 may provide, for example, for wired communication in some implementations, or for wireless communication in other implementations, and multiple interfaces may also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 may also be provided and connected to the mobile computing device 1550 through an expansion interface 1572, which may include, for example, a SIMM (Single In Line Memory Module) card interface. The expansion memory 1574 may provide extra storage space for the mobile computing device 1550, or may also store applications or other information for the mobile computing device 1550. Specifically, the expansion memory 1574 may include instructions to carry out or supplement the processes described above, and may include secure information also. Thus, for example, the expansion memory 1574 may be provided as a security module for the mobile computing device 1550, and may be programmed with instructions that permit secure use of the mobile computing device 1550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1552), perform one or more methods, such as those described above. The instructions can also be stored by one or more storage devices, such as one or more computer- or machine-readable mediums (for example, the memory 1564, the expansion memory 1574, or memory on the processor 1552). In some implementations, the instructions can be received in a propagated signal, for example, over the transceiver 1568 or the external interface 1562.

The mobile computing device 1550 may communicate wirelessly through the communication interface 1566, which may include digital signal processing circuitry where necessary. The communication interface 1566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1568 using a radio-frequency. In addition, short-range communication may occur, such as using a Bluetooth®, Wi-Fi™, or other such transceiver (not shown). In addition, a GPS (Global Positioning System) receiver module 1570 may provide additional navigation- and location-related wireless data to the mobile computing device 1550, which may be used as appropriate by applications running on the mobile computing device 1550.

The mobile computing device 1550 may also communicate audibly using an audio codec 1560, which may receive spoken information from a user and convert it to usable digital information. The audio codec 1560 may likewise generate audible sound for a user, such as through a speaker, e.g., in a handset of the mobile computing device 1550. Such sound may include sound from voice telephone calls, may include recorded sound (e.g., voice messages, music files, etc.) and may also include sound generated by applications operating on the mobile computing device 1550.

The mobile computing device 1550 may be implemented in a number of different forms, as shown in the figure. For example, it may be implemented as a cellular telephone 1580. It may also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automated sinogram completion, the method comprising the steps of:
   (a) accessing, by a processor of a computing device, a downsampled sinogram comprising data recorded by a detector during multi-angle scanning of a subject;
   (b) accessing, by the processor, a truncated sinogram comprising data recorded by the detector during multi-angle scanning of the subject;
   (c) interpolating, by the processor, each projection of the downsampled sinogram based on a resolution of the truncated sinogram, wherein the interpolating converts the resolution of each projection of the downsampled sinogram to the resolution of the truncated sinogram and thereby obtains a plurality of interpolated projections;
   (d) determining, by the processor, a plurality of combined projections using projections of the truncated sinogram and the interpolated projections; and
   (e) creating, by the processor, a 3D image of the subject using the combined projections.

2. The method of claim 1, wherein:
   each projection of the downsampled sinogram represents signals recorded across a first region of a detector and has a first resolution, and
   each projection of the truncated sinogram represents signals recorded across a second region of the detector and has a second resolution, wherein the second region is a sub-region of the first region and the second resolution is higher than the first resolution.

3. The method of claim 1, wherein determining each combined projection of the plurality of combined projections comprises:
   storing, in data elements of the combined projection that are associated with locations of the detector that are within a first region of the detector but outside of a second region of the detector, values from corresponding data elements of a corresponding interpolated projection, wherein each projection of the downsampled sinogram stores data representing signals from a first region and each projection of the truncated sinogram stores data representing signals from the second region; and storing, in data elements of the combined projection that are associated with locations of the detector within the second region, values from corresponding data elements of a corresponding projection of the truncated sinogram.

4. The method of claim 1, wherein the 3D image of the subject is obtained via tomographic reconstruction wherein each projection of a plurality of projections is processed individually such that, for each projection, a reconstruction sub-step is performed that (i) operates on the given projection, and (ii) updates values of a stored 3D dataset by combining the result of (i) with the stored 3D dataset, wherein the 3D dataset is the 3D image of the subject following the processing of the plurality of projections.

5. The method of claim 1, comprising performing steps (c) through (e) such that it is only necessary to store one combined projection in memory at a time.

6. The method of claim 1, wherein the downsampled sinogram comprises a plurality of downsampled projections acquired using a first multi-angle scan of the subject and the truncated sinogram comprises a plurality of truncated projections acquired using a second multi-angle scan of the subject.

7. The method of claim 1 comprising:
acquiring, via a first multi-angle scan of the subject, a plurality of downsampled projections to obtain the downsampled sinogram; and
acquiring, via a second multi-angle scan of the subject, a plurality of truncated projections to obtain the truncated sinogram.

8. The method of claim 1, wherein both the downsampled sinogram and the truncated sinogram are obtained using a single multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

9. The method of claim 1, comprising, for each of a plurality of angles of a multi-angle scan of the subject:
acquiring a corresponding initial projection that stores data representing signals from a first region of the detector;
downsampling, by the processor, the acquired projection to a reduced resolution, thereby obtaining a downsampled projection having a resolution that is lower than that of the initial projection;
storing, by the processor, the downsampled projection as a projection of the downsampled sinogram;
cropping, by the processor, the initial projection to obtain a truncated projection that stores data representing signals from a region of the detector that is a subregion of the first region and smaller than the first region; and
storing the truncated projection as a projection of the truncated sinogram.

10. The method of claim 1, wherein the processor comprises one or more processing units of a first type and one or more processing units of a second type.

11. The method of claim 10, wherein steps (a) and (b) are performed by one or more processing units of the first type and steps (c) through (e) are performed by one or more processing units of the second type.

12. The method of claim 2, wherein the second region of the detector is predefined.

13. The method of claim 2, comprising:
identifying, by the processor, a region of interest (ROI) within an image of the subject; and
determining, by the processor, the second region of the detector based on the identified ROI.

14. A method for automated sinogram completion, the method comprising the steps of:
(a) accessing, by a processor of a computing device, a downsampled sinogram for a subject, wherein the downsampled sinogram comprises a plurality of downsampled projections, wherein:
each downsampled projection is associated with a specific angle of a multi-angle scan of the subject,
each downsampled projection stores data representing signals from a first region of a detector recorded for the specific angle with which the downsampled projection is associated, and
each downsampled projection has a first resolution;
(b) accessing, by the processor, a truncated sinogram for the subject, wherein the truncated sinogram comprises a plurality of truncated projections, wherein:
each truncated projection is associated with a specific angle of a multi-angle scan of the subject,
each truncated projection stores data representing signals from a second region of a detector recorded for the specific angle with which the truncated projection is associated, wherein the second region is a sub-region of the first region, and
each truncated projection has a second resolution, wherein the second resolution is higher than the first resolution;
(c) initializing a 3D dataset, and, for each angle with which a downsampled projection is associated:
(i) interpolating, by the processor, the downsampled projection to convert its resolution from the first resolution to the second resolution, thereby obtaining an interpolated projection;
(ii) obtaining, by the processor, a combined projection using data from the interpolated projection and data from a corresponding truncated projection that is associated with the respective angle by:
storing, in data elements associated with locations of the detector within the second region, values from corresponding data elements of the corresponding truncated projection of the truncated sinogram; and
storing, in data elements associated with locations of the detector outside of the second region but within the first region, values from corresponding data elements of the interpolated projection;
(iii) determining, by the processor, a back-projection of the combined projection; and
(iv) updating, by the processor, the 3D dataset by combining the back-projection of the combined projection with the 3D dataset, such that once all angles are processed, the 3D dataset represents a 3D image of the subject.

15. The method of claim 14, comprising performing step (c) such that it is only necessary to store one combined projection in memory at a time.

16. The method of claim 14, wherein the downsampled sinogram comprises a plurality of downsampled projections acquired using a first multi-angle scan of the subject and the truncated sinogram comprises a plurality of truncated projections acquired using a second multi-angle scan of the subject.

17. The method of claim 14 comprising:
acquiring, via a first multi-angle scan of the subject, a plurality of downsampled projections to obtain the downsampled sinogram; and
acquiring, via a second multi-angle scan of the subject, a plurality of truncated projections to obtain the truncated sinogram.

18. The method of claim 14, wherein both the downsampled sinogram and the truncated sinogram are obtained using a single multi-angle scan of the subject, each projection of the downsampled sinogram corresponding to a downsampled version of a projection of the multi-angle scan and each projection of the truncated sinogram corresponding to a cropped version of a projection acquired in the multi-angle scan.

19. The method of claim 14, comprising, for each of a plurality of angles of a multi-angle scan of the subject:
acquiring a corresponding initial projection that stores data representing signals from a first region of the detector;
downsampling, by the processor, the acquired projection to a reduced resolution, thereby obtaining a downsampled projection having a resolution that is lower than that of the initial projection;
storing, by the processor, the downsampled projection as a projection of the downsampled sinogram;
cropping, by the processor, the initial projection to obtain a truncated projection that stores data representing signals from a region of the detector that is a subregion of the first region and smaller than the first region; and
storing the truncated projection as a projection of the truncated sinogram.

20. The method of claim 14, wherein the processor comprises one or more processing units of a first type and one or more processing units of a second type.

21. The method of claim 20, wherein steps (a) and (b) are performed by one or more processing units of the first type and step (c) is performed by one or more processing units of the second type.

22. The method of claim 14, wherein the second region of the detector is predefined.

23. The method of claim 14, comprising:
identifying, by the processor, a region of interest (ROI) within an image of the subject; and
determining, by the processor, the second region of the detector based on the identified ROI.

24. A system for automated sinogram completion, the system comprising:
a processor; and
a memory having instructions stored thereon, wherein the instructions, when executed by the processor, cause the processor to:
(a) access a downsampled sinogram comprising data recorded by a detector during multi-angle scanning of a subject;
(b) access a truncated sinogram comprising data recorded by the detector during multi-angle scanning of the subject;
(c) interpolate each projection of the downsampled sinogram based on a resolution of the truncated sinogram, wherein the interpolating converts the resolution of each projection of the downsampled sinogram to the resolution of the truncated sinogram and thereby obtains a plurality of interpolated projections;
(d) determine a plurality of combined projections using projections of the truncated sinogram and the interpolated projections; and
(e) create a 3D image of the subject using the combined projections.

25. The system of claim 24, further comprising a CT scanner for acquiring the projections of a subject.

26. A system for automated sinogram completion, the system comprising:
a processor; and
a memory having instructions stored thereon, wherein the instructions, when executed by the processor, cause the processor to:
(a) access a downsampled sinogram for a subject, wherein the downsampled sinogram comprises a plurality of downsampled projections, wherein:
each downsampled projection is associated with a specific angle of a multi-angle scan of the subject,
each downsampled projection stores data representing signals from a first region of a detector recorded for the specific angle with which the downsampled projection is associated, and
each downsampled projection has a first resolution;
(b) access a truncated sinogram for the subject, wherein the truncated sinogram comprises a plurality of truncated projections, wherein:
each truncated projection is associated with a specific angle of a multi-angle scan of the subject,
each truncated projection stores data representing signals from a second region of a detector recorded for the specific angle with which the truncated projection is associated, wherein the second region is a sub-region of the first region, and
each truncated projection has a second resolution, wherein the second resolution is higher than the first resolution;
(c) initialize a 3D dataset, and, for each angle with which a downsampled projection is associated:
(i) interpolate the downsampled projection to convert its resolution from the first resolution to the second resolution, thereby obtaining an interpolated projection;
(ii) obtain a combined projection using data from the interpolated projection and data from a corresponding truncated projection that is associated with the respective angle by:
storing, in data elements associated with locations of the detector within the second region, values from corresponding data elements of the corresponding truncated projection of the truncated sinogram; and
storing, in data elements associated with locations of the detector outside of the second region but within the first region, values from corresponding data elements of the interpolated projection;
(iii) determine a back-projection of the combined projection; and
(iv) update the 3D dataset by combining the back-projection of the combined projection with the 3D dataset, such that once all angles are processed, the 3D dataset represents a 3D image of the subject.

27. The system of claim 26, further comprising a CT scanner for acquiring the projections of a subject.

* * * * *